United States Patent
Zhang et al.

(10) Patent No.: US 10,927,100 B2
(45) Date of Patent: Feb. 23, 2021

(54) DEGRADABLE IMIDAZOLIUM OLIGOMER AND POLYMER FOR ANTIMICROBIAL APPLICATIONS

(71) Applicant: AGENCY FOR SCIENCE, TECHNOLOGY AND RESEARCH, Singapore (SG)

(72) Inventors: Yugen Zhang, Singapore (SG); Yuan Yuan, Singapore (SG); Shu Wen Diane Lim, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/617,562

(22) PCT Filed: Jun. 28, 2018

(86) PCT No.: PCT/SG2018/050315
§ 371 (c)(1),
(2) Date: Nov. 27, 2019

(87) PCT Pub. No.: WO2019/004940
PCT Pub. Date: Jan. 3, 2019

(65) Prior Publication Data
US 2020/0181122 A1 Jun. 11, 2020

(30) Foreign Application Priority Data
Jun. 30, 2017 (SG) .......................... 10201705438U

(51) Int. Cl.
C07D 403/12 (2006.01)
A61P 31/04 (2006.01)
A01N 43/50 (2006.01)
C08G 73/06 (2006.01)

(52) U.S. Cl.
CPC ........... *C07D 403/12* (2013.01); *A01N 43/50* (2013.01); *A61P 31/04* (2018.01); *C08G 73/0616* (2013.01)

(58) Field of Classification Search
None
See application file for complete search history.

(56) References Cited

U.S. PATENT DOCUMENTS

| 6,416,770 B1 | 7/2002 | Leduc et al. |
| 2010/0004389 A1 | 1/2010 | Paley et al. |

FOREIGN PATENT DOCUMENTS

| KR | 2016-0066424 A | 6/2016 |
| WO | WO-2012/050531 A1 | 4/2012 |
| WO | WO-2014/025314 A1 | 2/2014 |
| WO | WO-2016/043660 A1 | 3/2016 |

OTHER PUBLICATIONS

McNulty et al., "A Scalable Process for the Synthesis of (E)-pterostilbene Involving Aqueous Wittig Olefination Chemistry", Tetrahedron Letters 54, 2013, pp. 6303-6306.
Riduan et al., "Ultrafast Killing and Self-gelling Antimicrobial Imidazolium Oligomers", Small, vol. 12, No. 14, 2016, pp. 1928-1934.
Fukushima et al., "Supramolecular High-aspect Ratio Assemblies With Strong Antifungal Activity", Nature Communications, 4:2861, 2013, 9 pages.
DeBerardinis et al., "Facile Synthesis of a Family of $H_8$BINOL-Amine Compounds and Catalytic Asymmetric Arylzinc Addition to Aldehydes", J. Org. Chem., 75, 2010, pp. 2836-2850.
Anderson et al., "Imidazole- and Imidazolium-containing Polymers for Biology and Material Science Applications", Polymer, vol. 51, No. 12, Feb. 8, 2010, pp. 2447-2454.
Search Report and Written Opinion in International Application No. PCT/SG2018/050315 dated Sep. 20, 2018, 15 pages.
Extended European Search Report in EP Application No. 18824729.0 dated Apr. 20, 2020, 8 pages.
Yuan et al., "pH-Degradable Imidazolium Oligomers as Antimicrobial Materials With Tuneable Loss of Activity", Biomaterials Science, vol. 7, No. 6, May 28, 2019, pp. 2317-2325.

*Primary Examiner* — Brian J Davis
(74) *Attorney, Agent, or Firm* — Marshall, Gerstein & Borun LLP

(57) ABSTRACT

The present invention relates to an oligomer of formula (I)

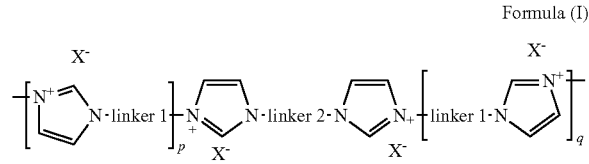

Formula (I)

where the various groups are as defined in the specification. The present invention also relates to an oligomer or a polymer of formula (II)

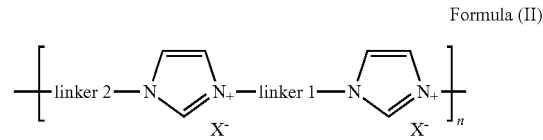

Formula (II)

where the various groups are as defined in the specification. The present invention also relates to the methods for their preparation, antimicrobial composition, antimicrobial gel containing these oligomers and/or polymers of Formula (I) and (II), and uses of these oligomers and/or polymers in the treatment of a microbial infection or disease.

27 Claims, 22 Drawing Sheets

[Fig. 1A]
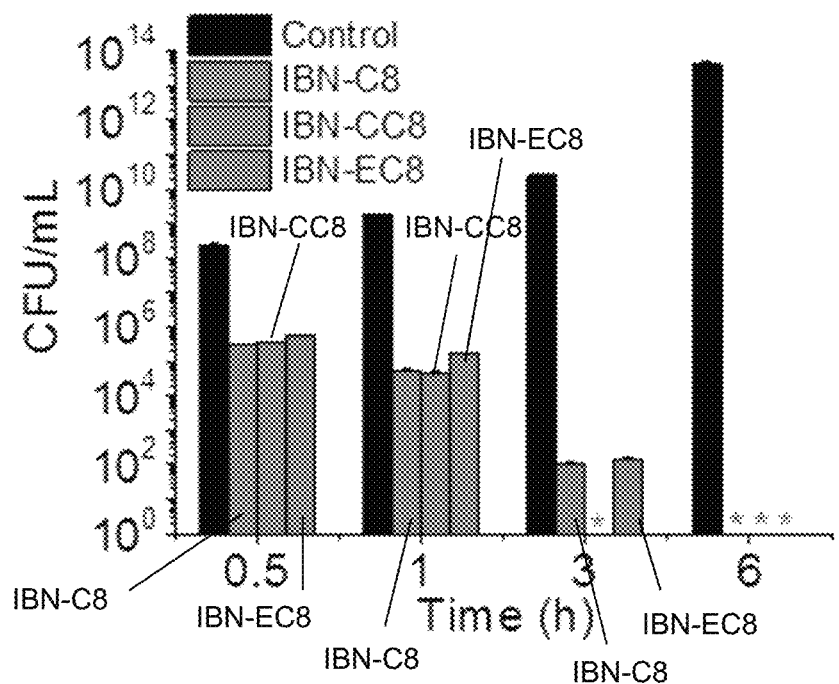
[Fig. 1B]
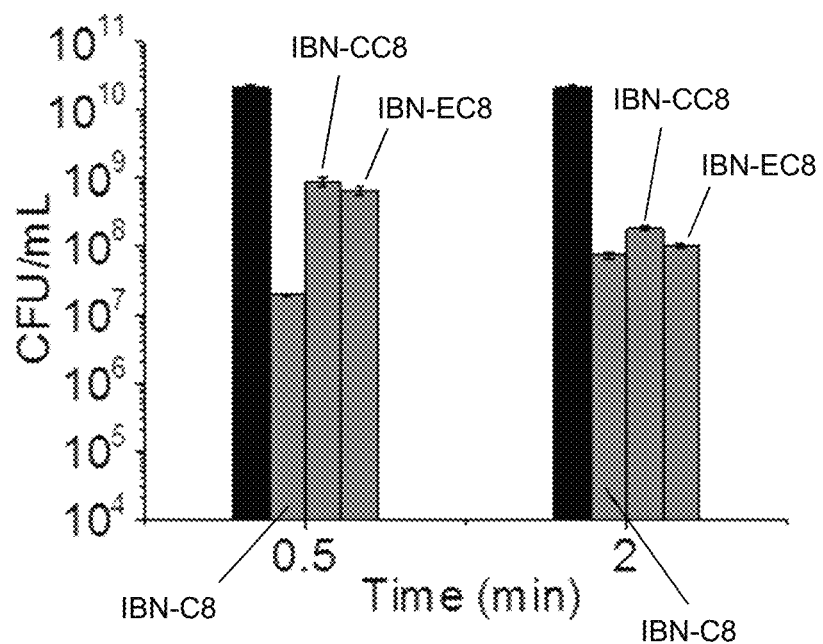

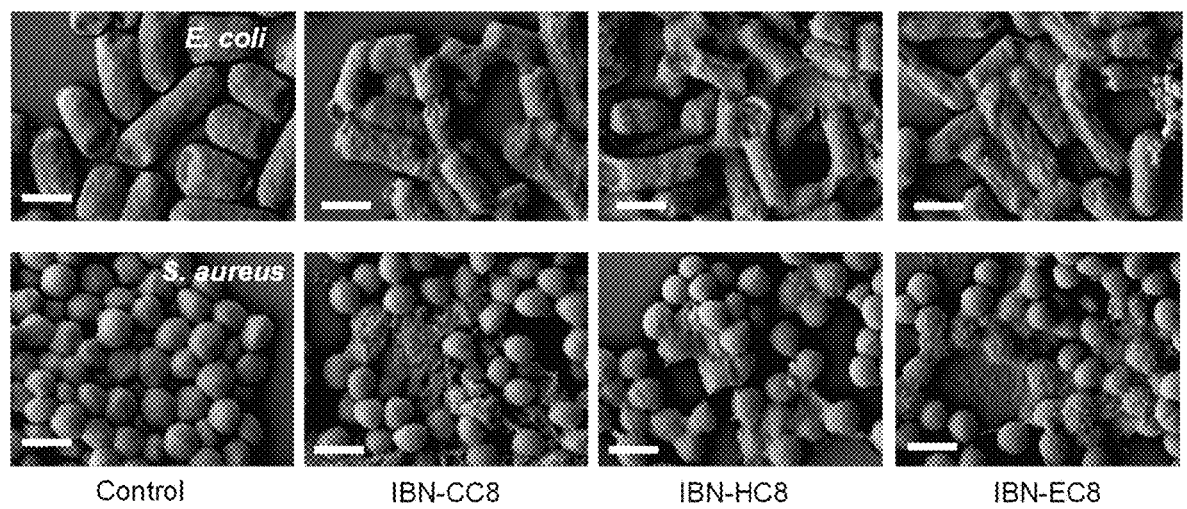
[Fig. 2]

[Fig. 3A]
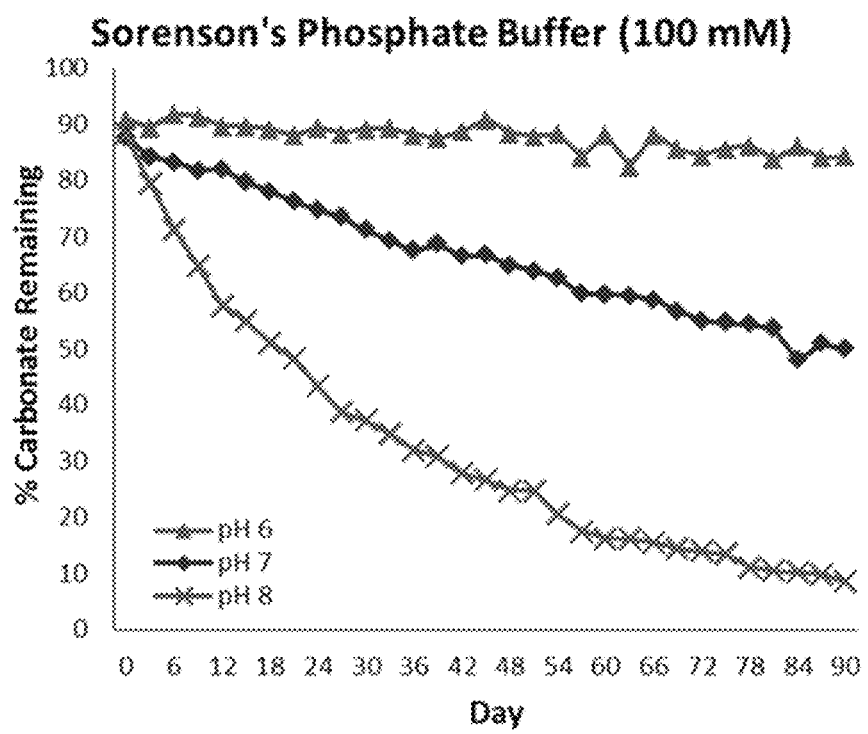
[Fig. 3B]
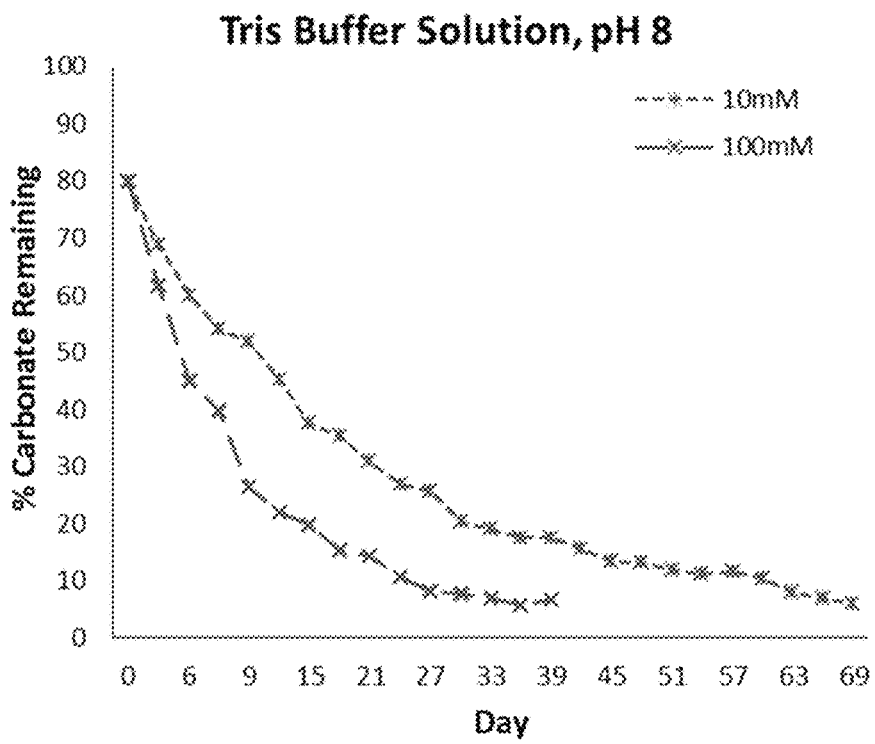

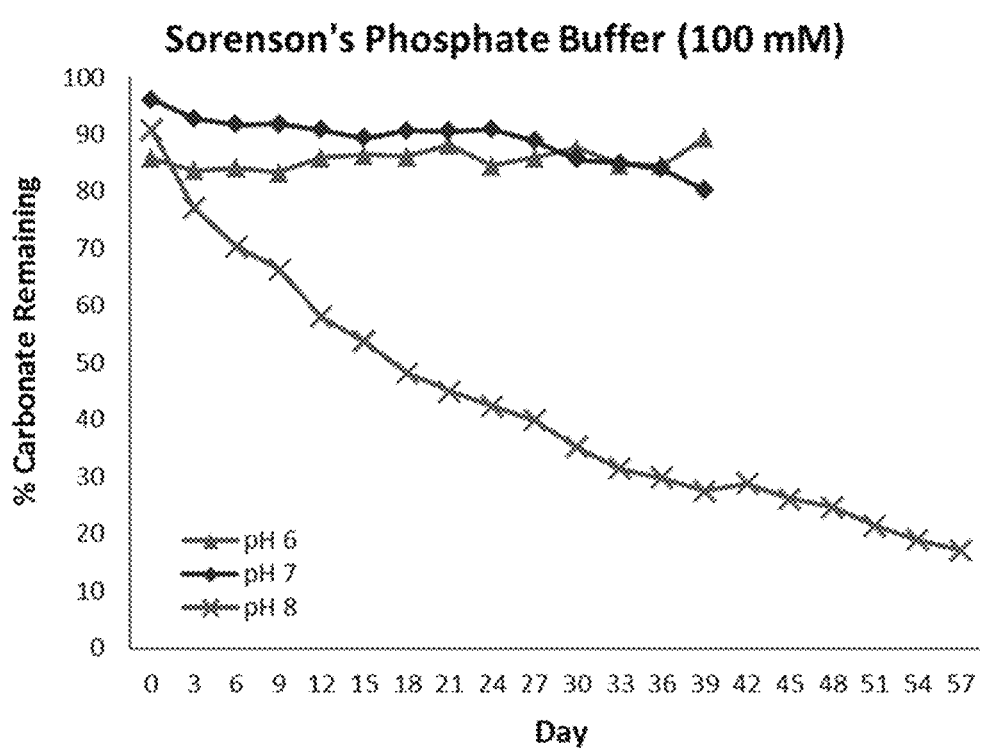
[Fig. 4]

[Fig. 5A]
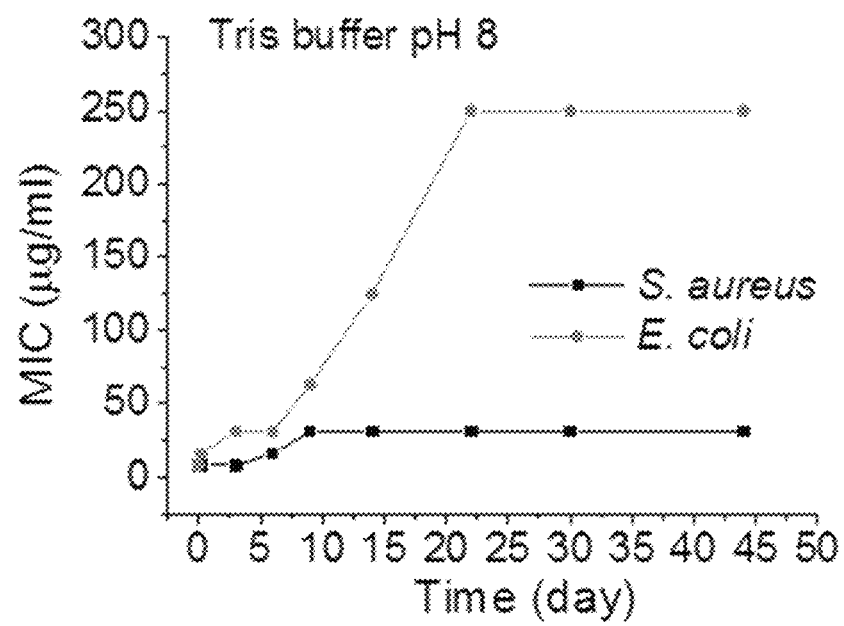
[Fig. 5B]
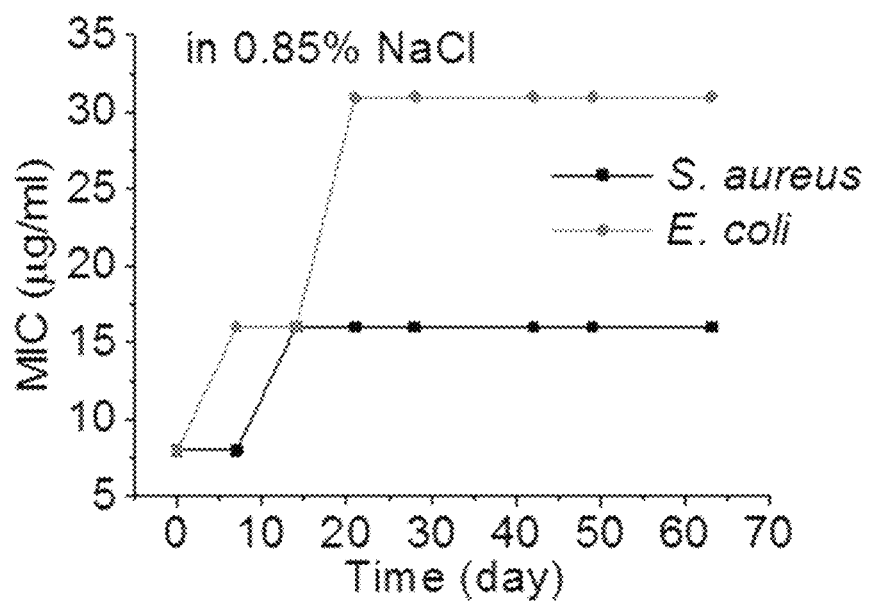

[Fig. 5C]
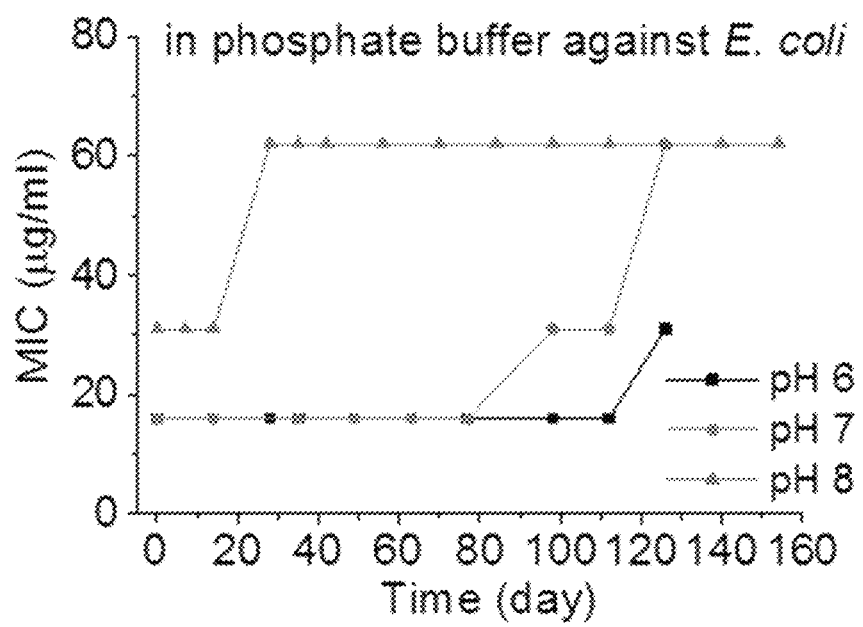
[Fig. 5D]
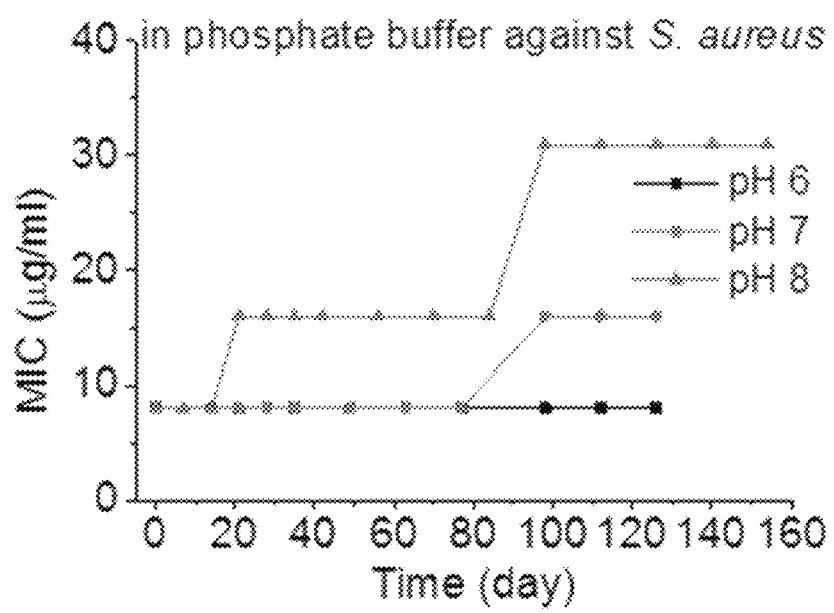

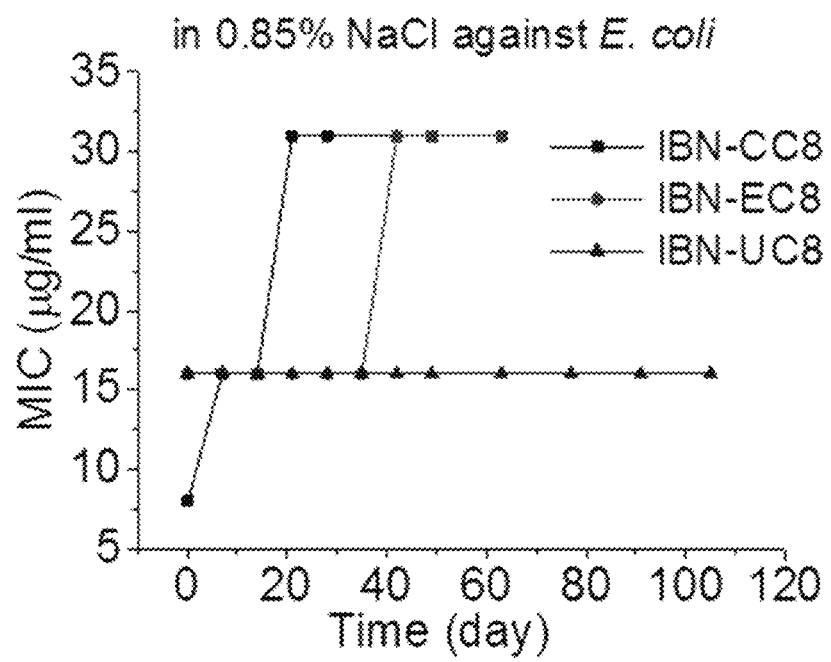
[Fig. 6A]
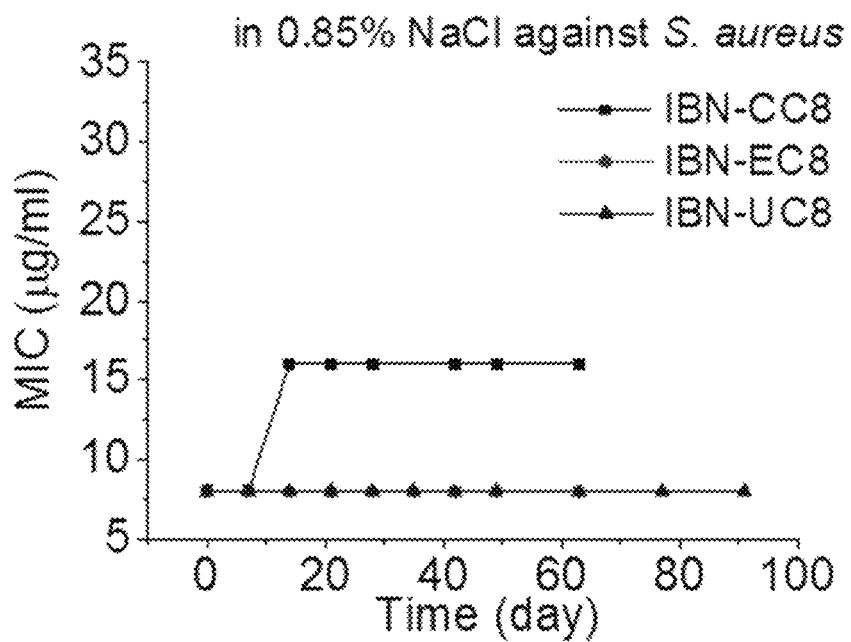
[Fig. 6B]

[Fig. 7A]
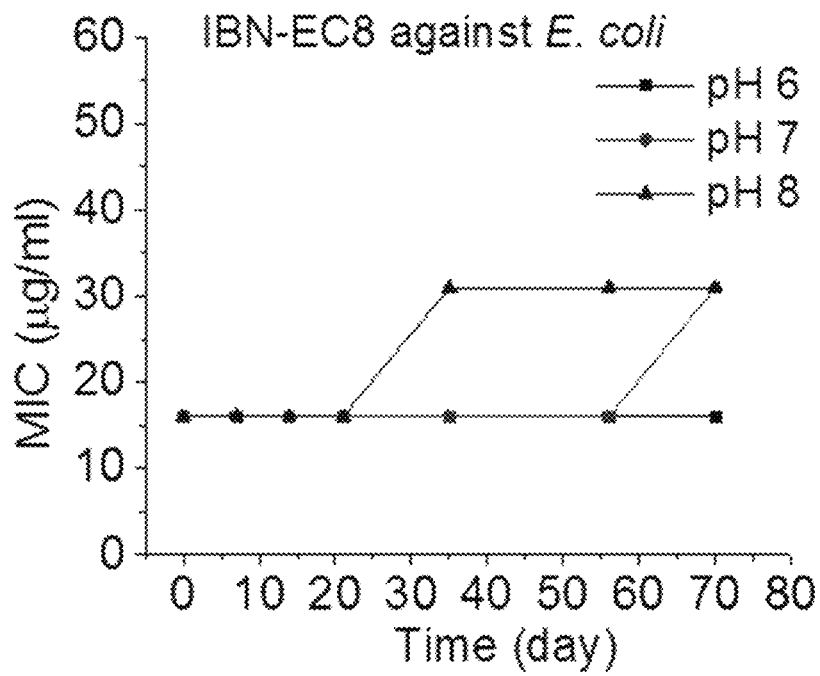
[Fig. 7B]
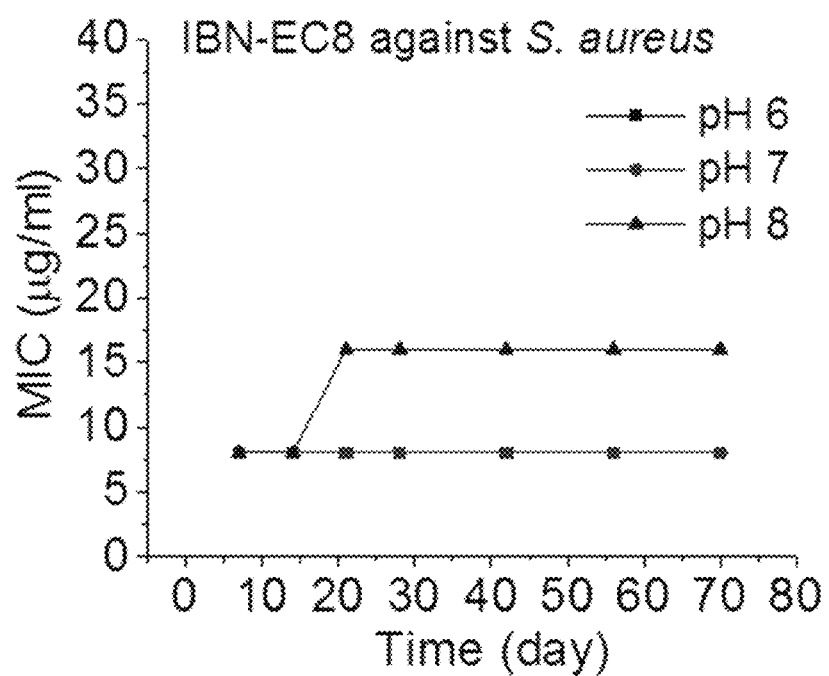

[Fig. 7C]
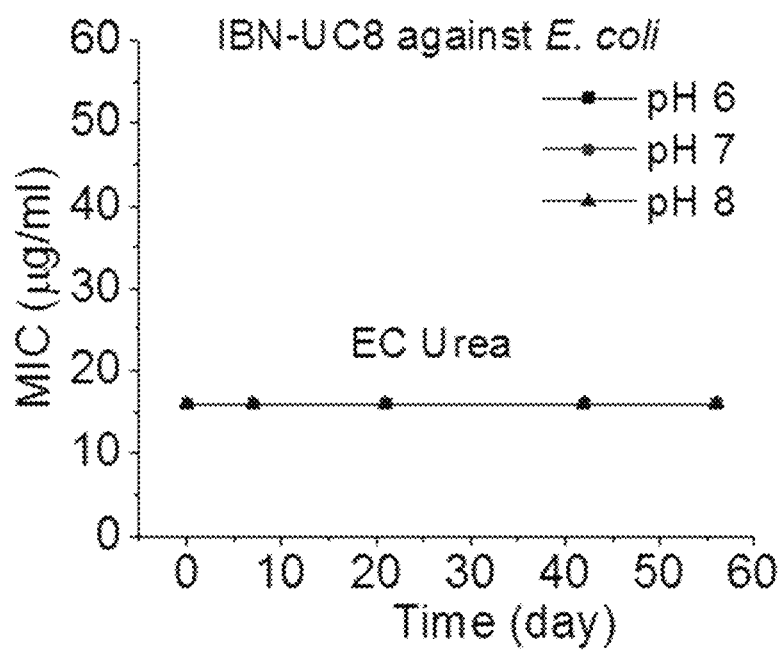
[Fig. 7D]
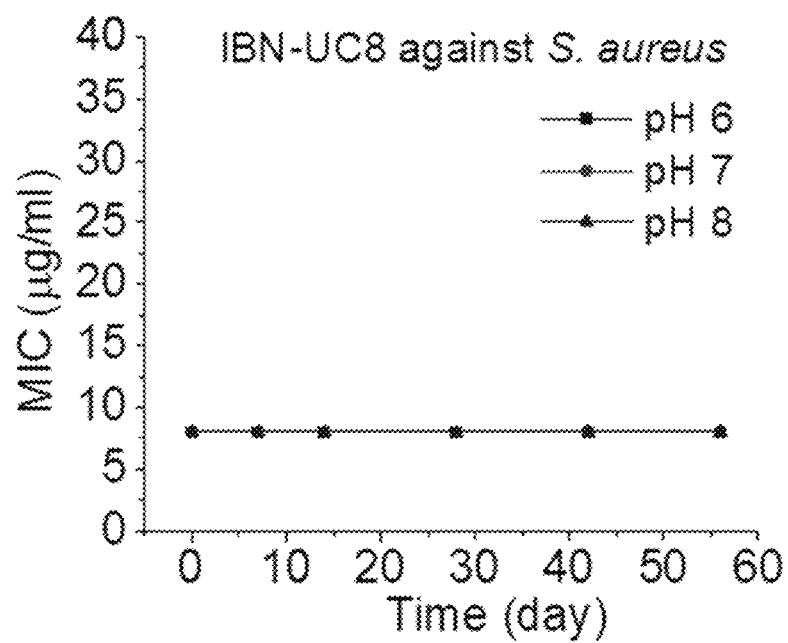

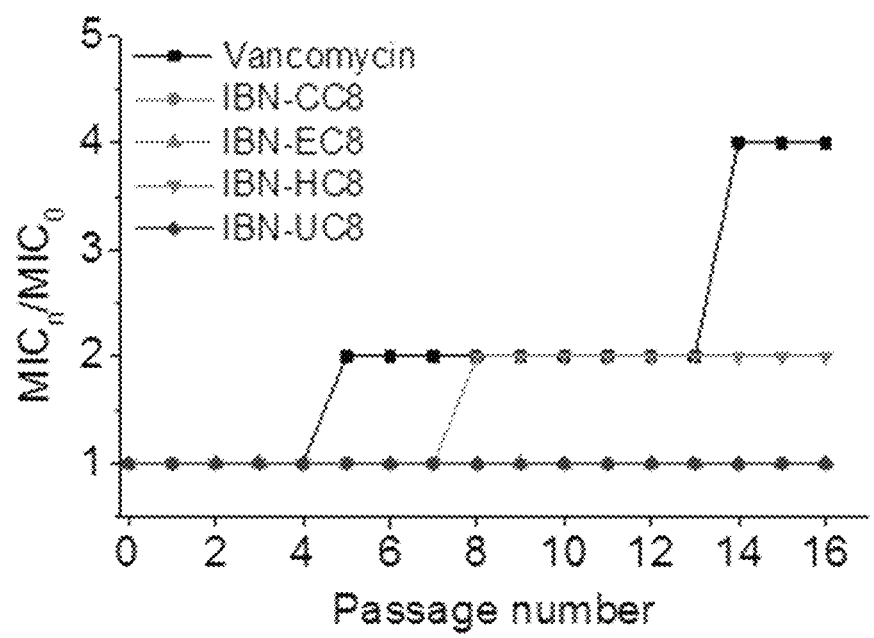
[Fig. 8]

[Fig. 9A]
[Fig. 9B]
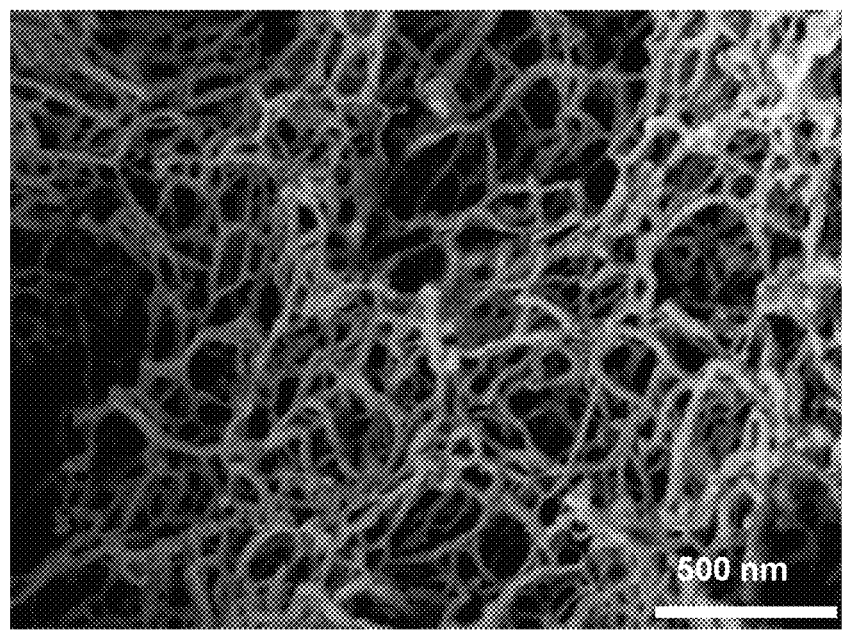

[Fig. 10A]
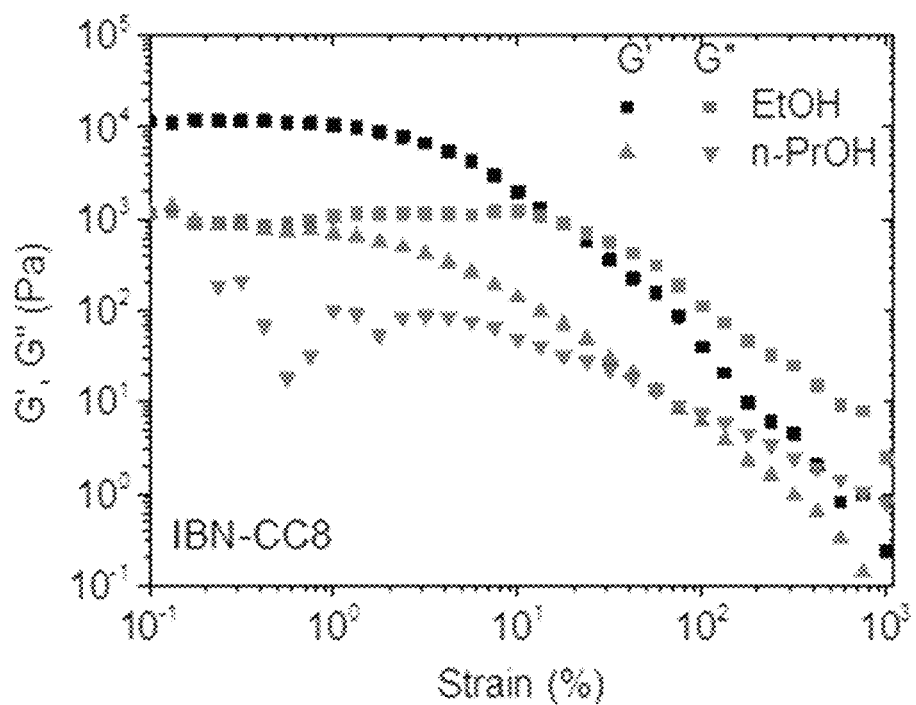
[Fig. 10B]
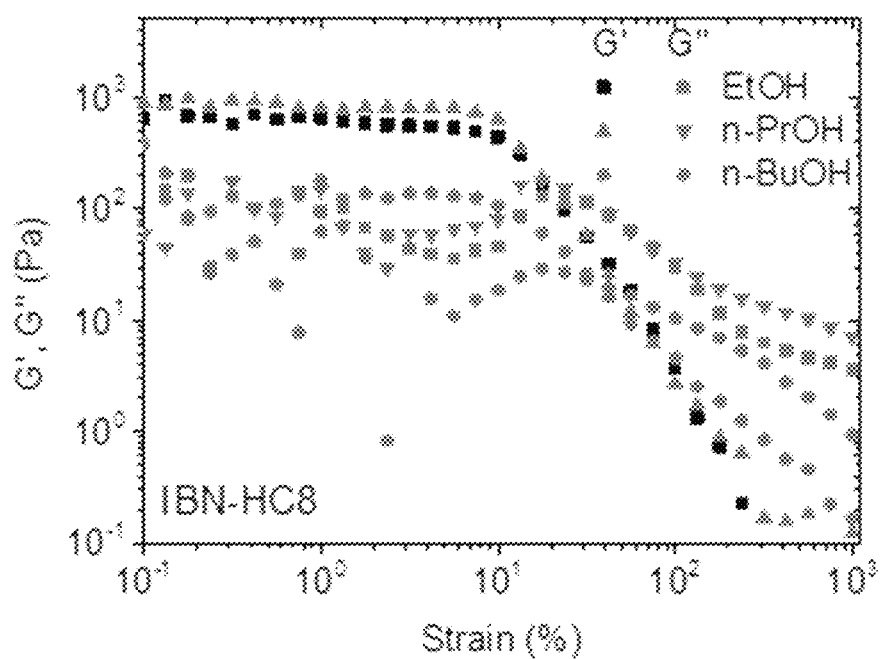

[Fig. 11A]
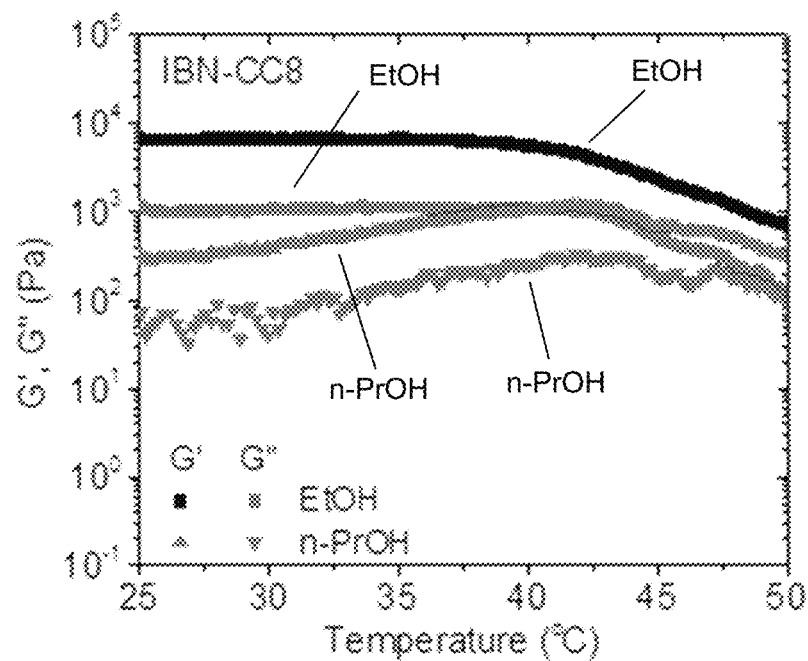
[Fig. 11B]
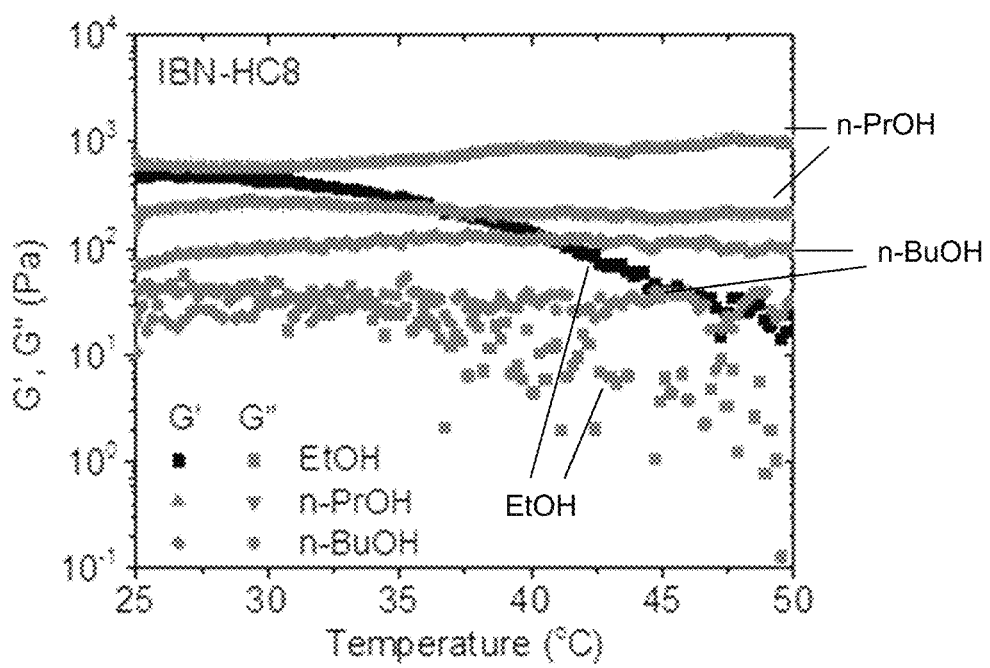

[Fig. 12A]
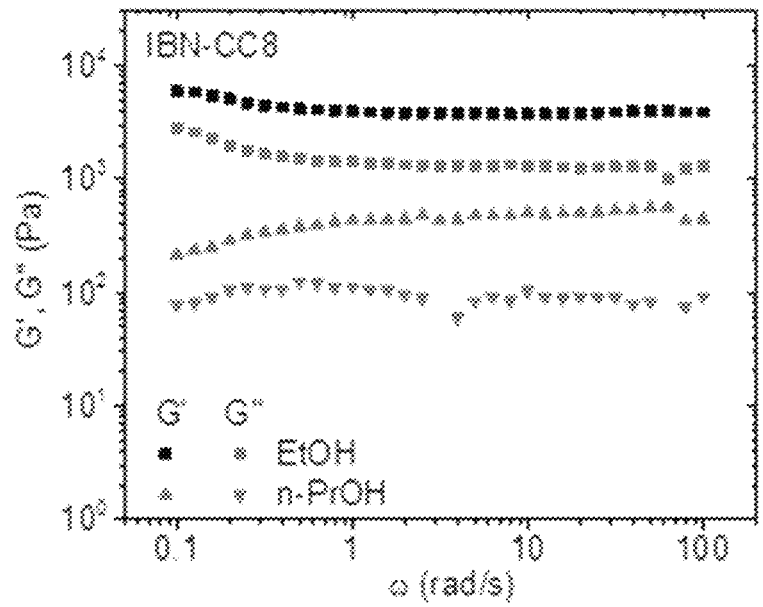
[Fig. 12B]
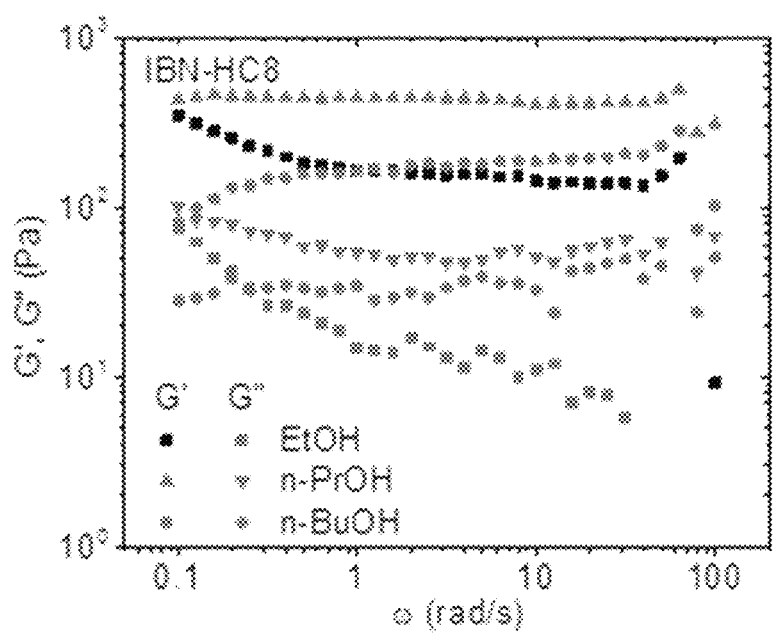

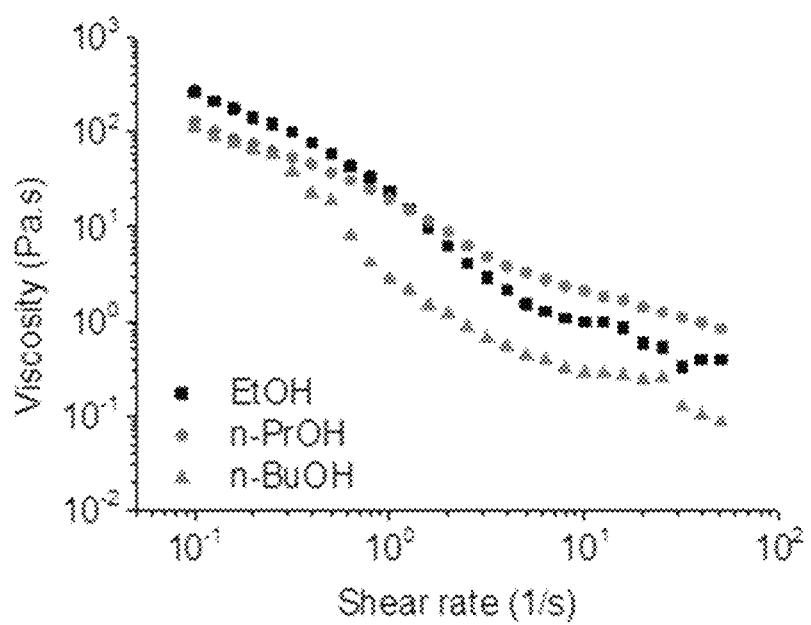
[Fig. 13]

[Fig. 14A]
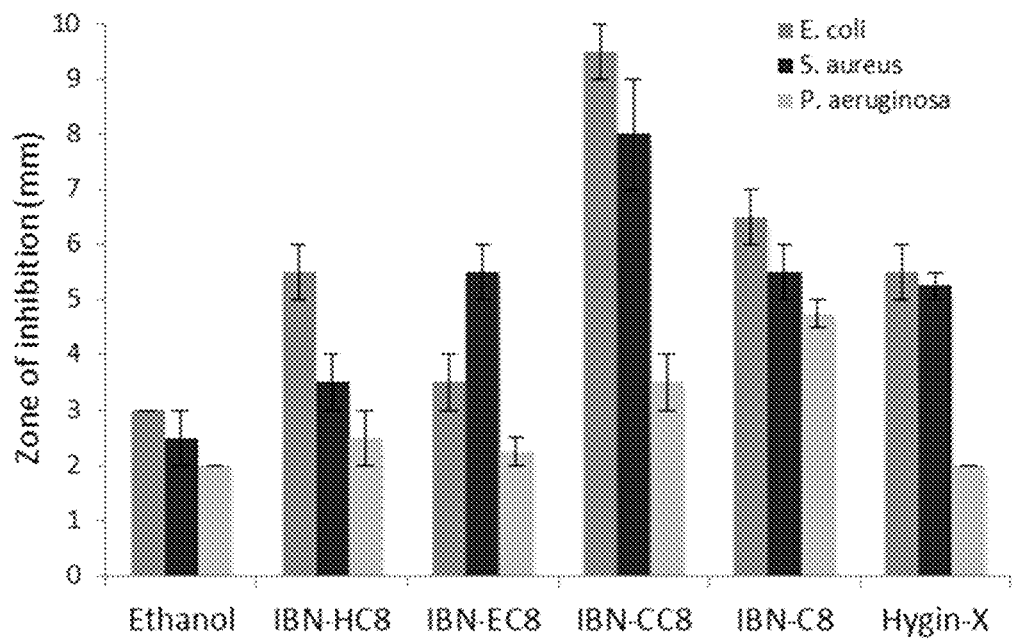
[Fig. 14B]
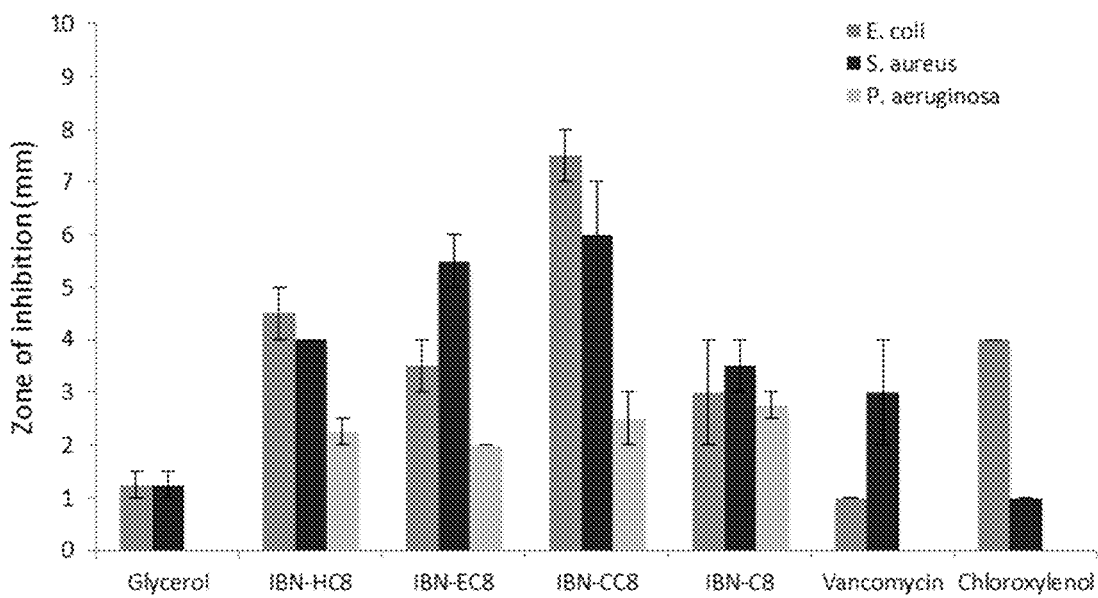

[Fig. 15]
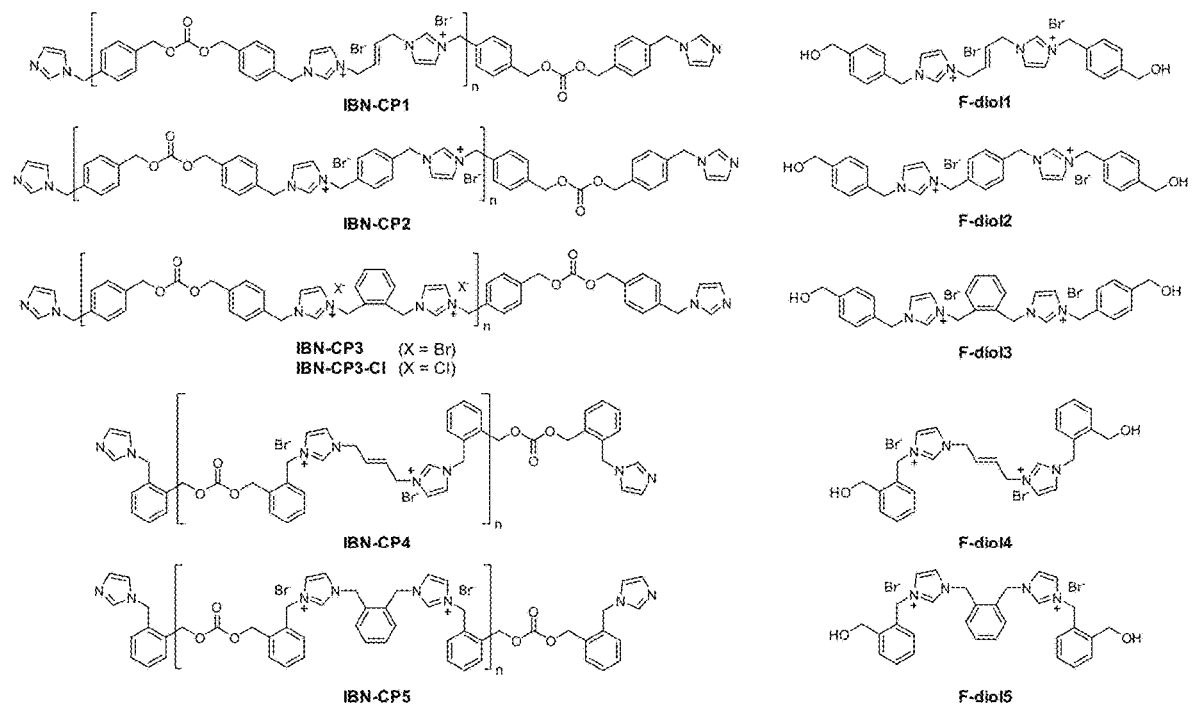
[Fig. 16]
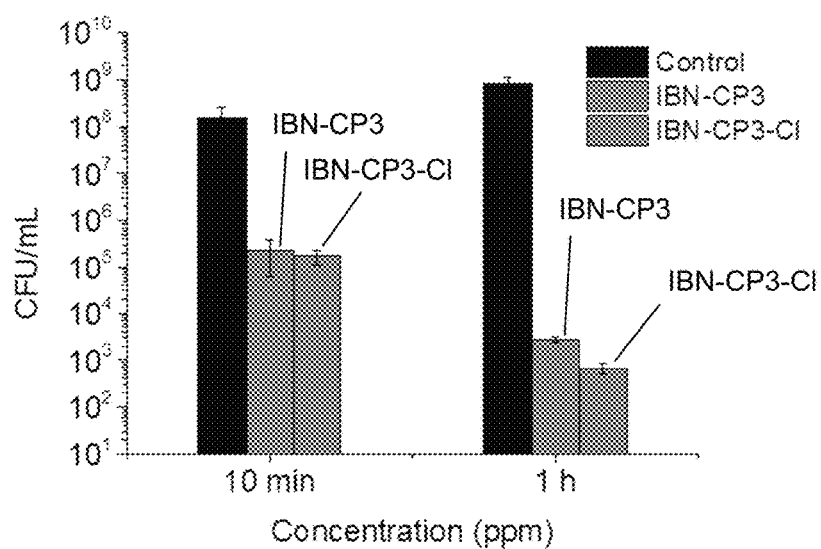

[Fig. 17A]
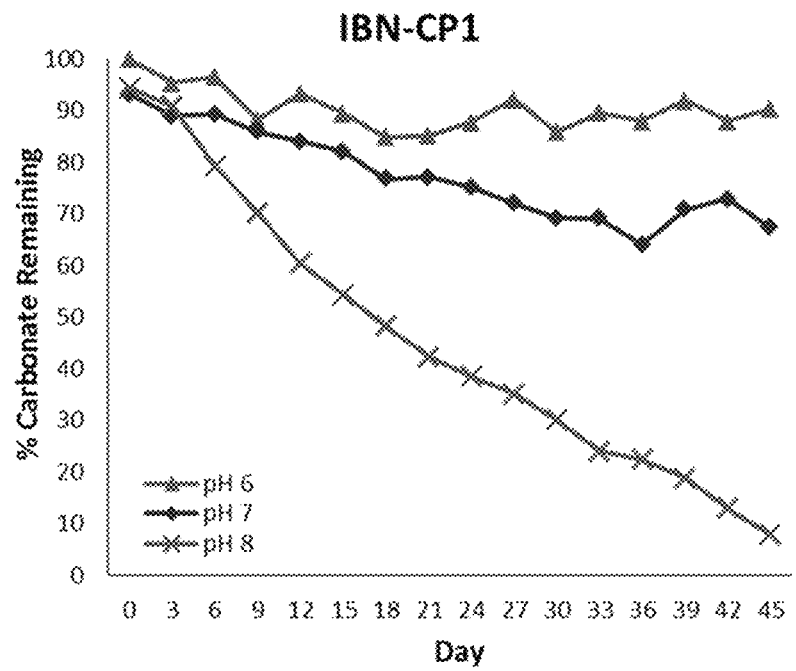
[Fig. 17B]
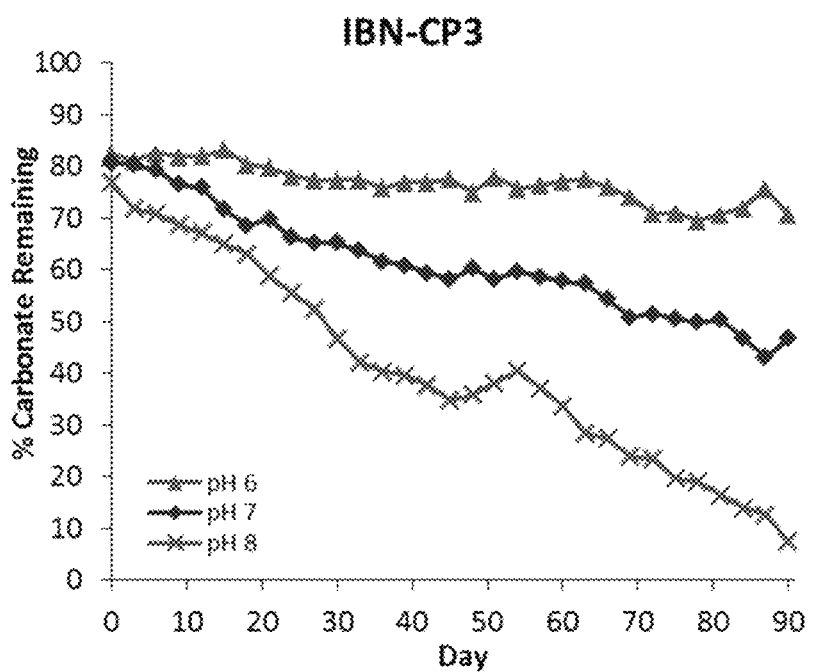

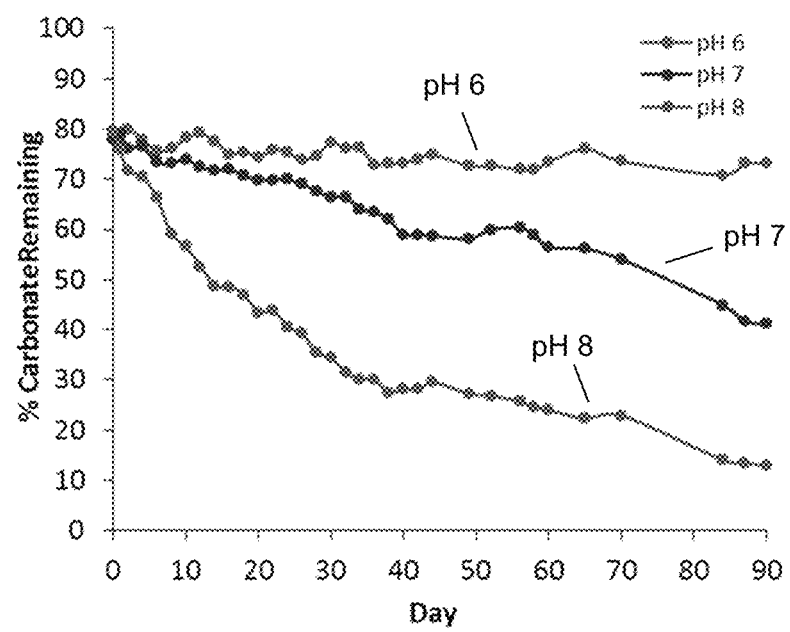
[Fig. 18]

[Fig. 19A]
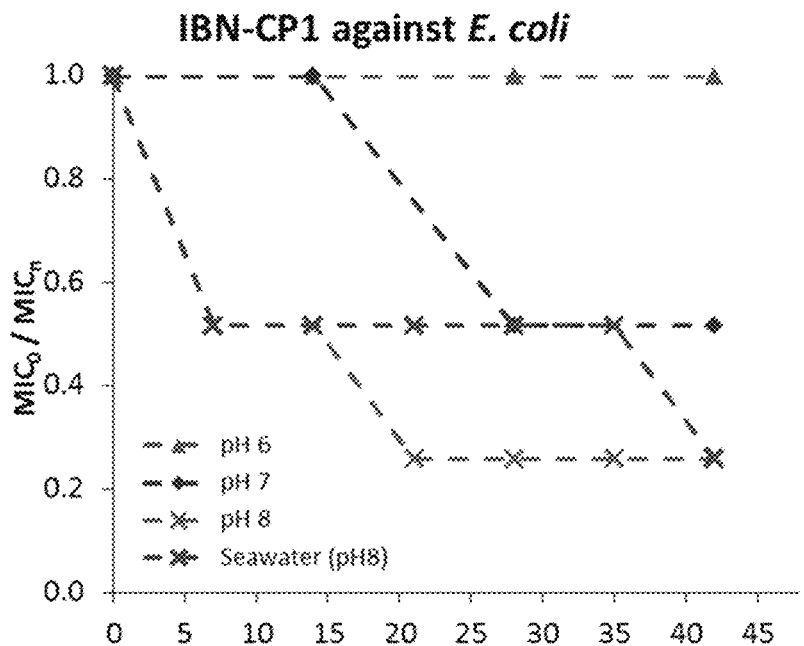
[Fig. 19B]
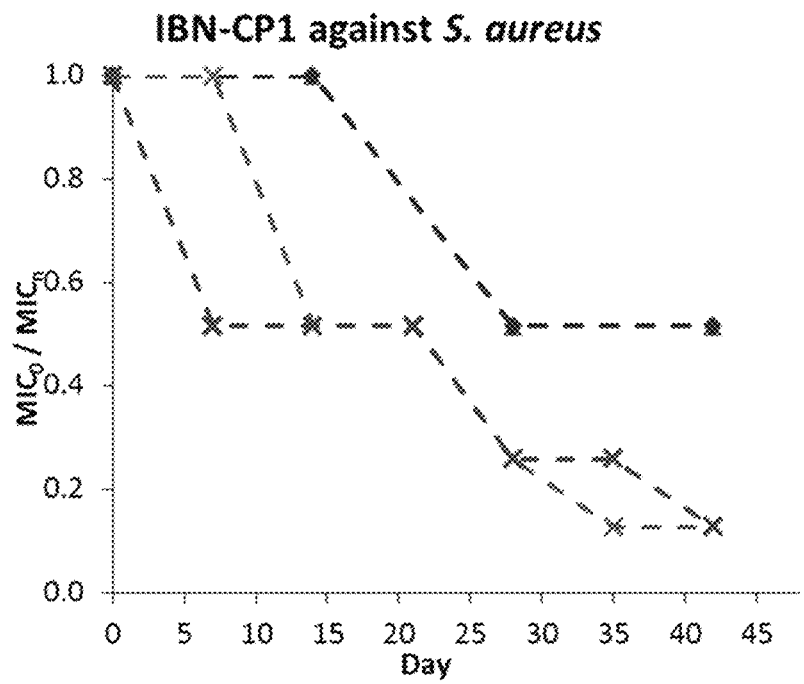

[Fig. 19C]
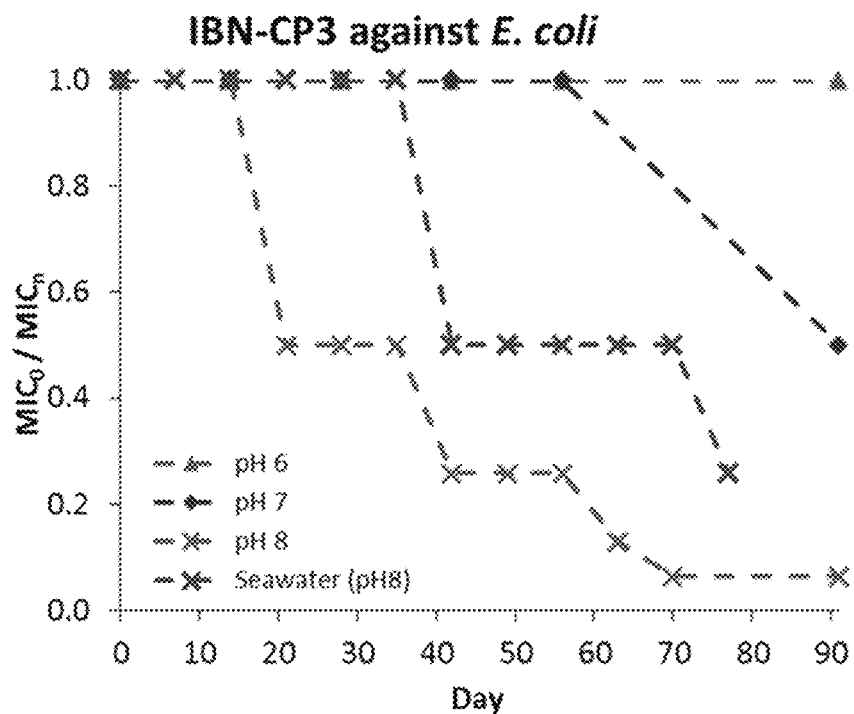
[Fig. 19D]
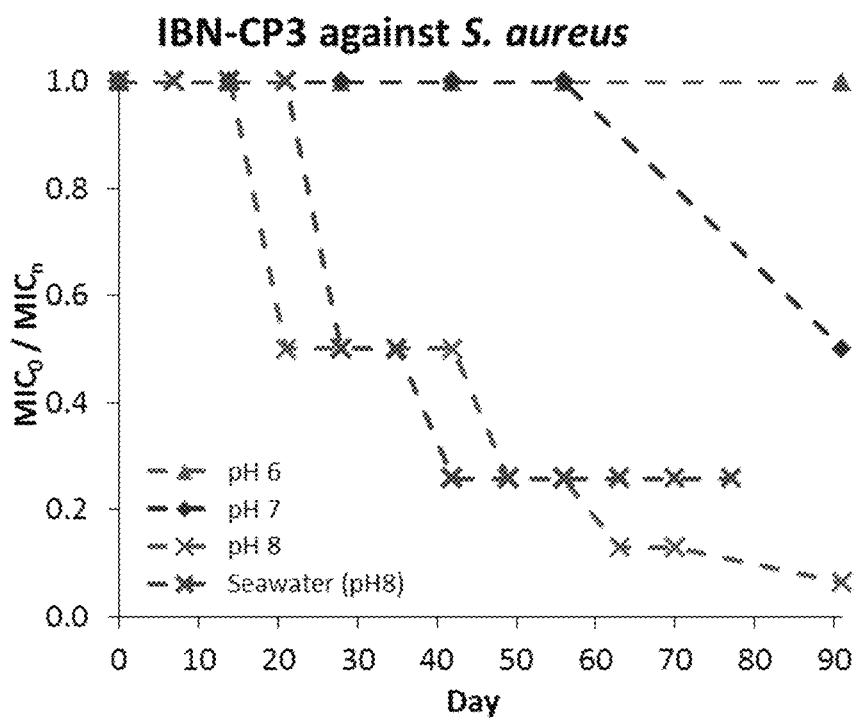

[Fig. 20]
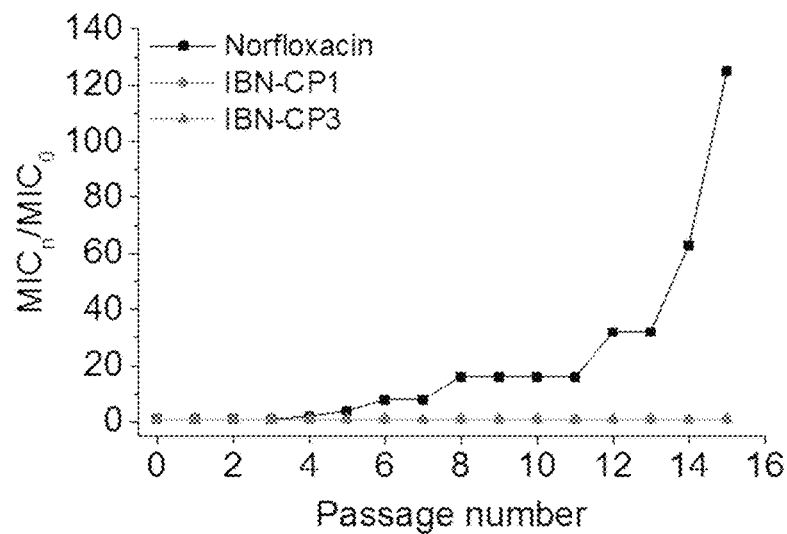
[Fig. 21]
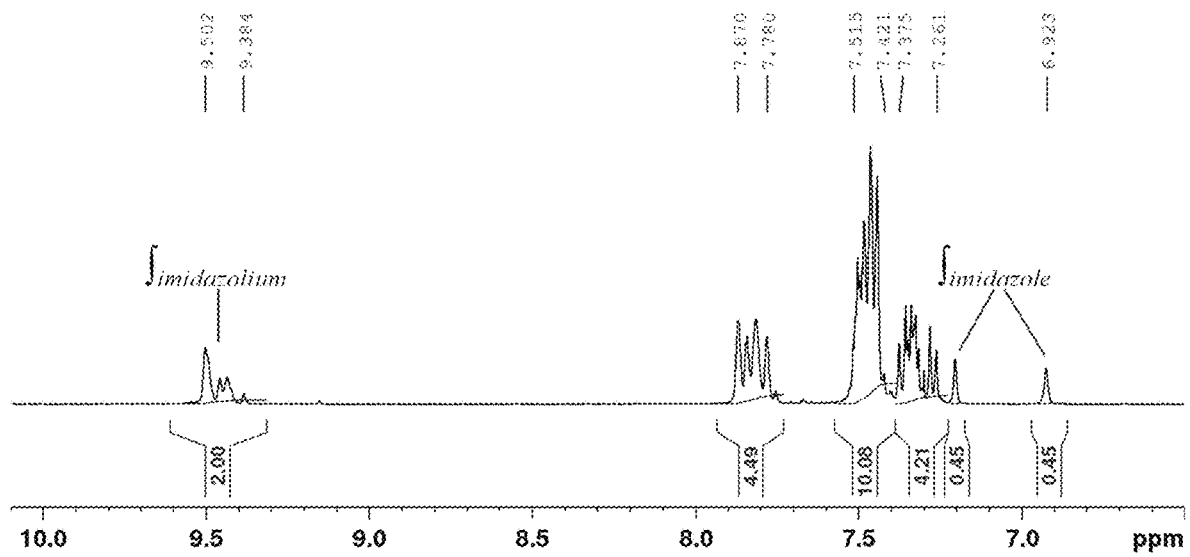

DEGRADABLE IMIDAZOLIUM OLIGOMER AND POLYMER FOR ANTIMICROBIAL APPLICATIONS

CROSS-REFERENCE TO RELATED APPLICATION

This application claims priority to Singapore application number 10201705438U filed on 30 Jun. 2017, the disclosure of which is hereby incorporated by reference.

TECHNICAL FIELD

The present invention generally relates to an oligomer of formula (I) or an oligomer or a polymer of formula (II). The present invention also relates to an antimicrobial composition, an antimicrobial gel, methods of producing the oligomer of formula (I) or the oligomer or the polymer of formula (II) and the uses thereof.

BACKGROUND ART

One of the most critical challenges facing modern society today is the antimicrobial resistance (AMR) of microorganisms to develop resistance against antimicrobial drugs such that the antimicrobial drugs are not able to work on such microoganisms or higher dosages of the antimicrobial drugs is required to have an effective therapeutic effect or outcome. This has led to a prediction of about 10 million deaths that are estimated to be caused by AMR annually in 2050. As a result of longer hospital stays and higher morbidity, the cost of treating antibiotic-resistant infections has been pegged between US$150 million to $30 billion a year. Most worryingly, emerging reports of bacterial infections by strains resistant to all existing drugs underscore the pressing need to tackle the issue of antibiotic resistance in bacteria.

Bacteria may acquire resistance during misuse or prolonged use of antibiotics in clinical treatment. Resistant strains can also be contracted directly from animals, water and air, or the community. Furthermore, overuse of antibiotics for non-therapeutic applications, such as agricultural and environmental disinfection, enhances resistance selection and result in accumulation of low levels of antibiotics in the ecosystem over long period of time. These antibiotic residues eventually enter the food chain, where they stand to contaminate downstream agriculture products. To combat resistance, it is essential to develop new antimicrobial technologies that circumvent or reduce selection for resistant microbial strains. One such technology would be antimicrobial materials that self-destruct after treatment, leaving no active residue with the potential for secondary environmental contamination. This is especially important in the context of agricultural and environmental disinfection.

Previously, we have developed a series of main-chain imidazolium polymers and oligomers for antimicrobial applications. These poly-imidazolium materials demonstrated high efficacy, high selectivity and fast killing kinetics against a broad range of bacteria and fungi. In this invention, a new series of imidazolium polymers and oligomers with various degradable linkers has been developed. The new imidazolium materials retain the excellent antimicrobial property of the previously reported materials against broad range of microbes, yet possess essential degradability and non-resistance properties. The new imidazolium materials have tuneable degradation profiles under different conditions which would have wide applications in agricultural and environmental disinfection.

Accordingly, there is a need for a new imidazolium compound that addresses or alleviates one or more disadvantages mentioned above. There is a need to provide an antimicrobial compound having desirable properties.

SUMMARY

According to a first aspect, there is provided an oligomer of formula (I)

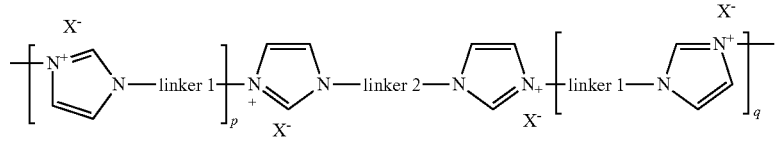

Formula (I)

wherein linker 1 is an alkyl-aryl-alkyl group or ($C_2$-$C_8$) alkene;

p and q are independently an integer from 2 to 6, that is, 2, 3, 4, 5, or 6;

linker 2 is

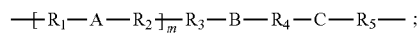

m is 0 or 1;

A is independently aryl or heteroaryl;

B is independently O, N or S;

C is independently aryl or heteroaryl;

$R_1$ is a bond or alkyl;

$R_2$ is a bond, alkoxy or amine;

$R_3$ is carbonyl, bond or alkyl;

$R_4$ is bond or alkyl; $R_5$ is alkyl; and

X is a halide selected from fluoride, chloride and bromide.

According to a another aspect, there is provided an oligomer or a polymer of formula (II)

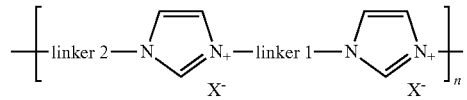

Formula (II)

wherein linker 1 is an alkyl-aryl-alkyl group or ($C_2$-$C_8$) alkene;

n is an integer from 3 to 30, that is, 3, 4, 5, 6, 7, 8, 9, 10, 11, 12, 13, 14, 15, 16, 17, 18, 19, 20, 21, 22, 23, 24, 25, 26, 27, 28, 29 or 30;

linker 2 is $$-\!\!+\!\!R_1-A-R_2\!\!+_{\!\!m}\!\!R_3-B-R_4-C-R_5-\ ;$$

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is a halide selected from fluoride, chloride and bromide.

Advantageously, the antimicrobial composition as defined herein may display an excellent antimicrobial activity against a broad range of microbes. More advantageously, the oligomer may be degradable and may have non-resistance property. The oligomer described herein may have a degradation profile that can be tuned under different conditions.

According to another aspect, there is provided an antimicrobial composition comprising the oligomer or the polymer as defined herein.

Advantageously, this means that the antimicrobial composition may not suffer from antimicrobial resistance. More advantageously, it may not be necessary to increase the dosage or concentration of the oligomer or polymer when used against the same microbe on the same surface or subject for a long period of time. Hence, the antimicrobial composition may be used against microbes that have developed a resistance to conventional antimicrobial drugs According to another aspect, there is provided an antimicrobial composition as defined herein for use in inhibiting microbial activity or for use in treating a microbial infection or disease.

According to another aspect, there is provided use of the antimicrobial composition as defined herein in the manufacture of a medicament for treating a microbial infection or disease.

According to another aspect, there is provided a method of inhibiting a microbial activity or treating a microbial infection or disease comprising administering the antimicrobial composition as defined herein to a subject or applying the antimicrobial composition as defined herein on a surface.

According to another aspect, there is provided a method preparing an oligomer of formula (I)

wherein linker 1 is an alkyl-aryl-alkyl group or ($C_2$-$C_8$) alkene;
p and q are independently an integer from 2 to 6, that is 2, 3, 4, 5 or 6;
linker 2 is $$-\!\!+\!\!R_1-A-R_2\!\!+_{\!\!m}\!\!R_3-B-R_4-C-R_5-\ ;$$

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl;
X is halide selected from fluoride, chloride and bromide,
said method comprising the steps of:

a) providing a di-imidazole unit bearing linker 2 of Formula (III)

Formula (III)

b) mixing the di-imidazole of Formula (III) with an imidazolium salt that is dissolved in a suitable solvent to form a mixture; and c) stirring the mixture obtained in step (b) under conditions to obtain said oligomer.

According to another aspect, there is provided a method of preparing the oligomer or the polymer of Formula (II)

Formula (II)

wherein linker 1 is an alkyl-aryl-alkyl group or ($C_2$-$C_8$) alkene;
n is an integer from 3 to 30, that is 3, 4, 5, 6, 7, 8, 9, 10, 11, 12, 13, 14, 15, 16, 17, 18, 19, 20, 21, 22, 23, 24, 25, 26, 27, 28, 29 or 30;
linker 2 is $$-\!\!+\!\!R_1-A-R_2\!\!+_{\!\!m}\!\!R_3-B-R_4-C-R_5-\ ;$$

Formula (I)

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is halide selected from fluoride, chloride and bromide, said method comprising the steps of:
a) mixing a di-imidazole unit bearing linker 2 of Formula (III):

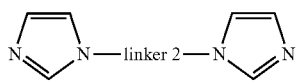

Formula III with a precursor bearing linker 1 of Formula (IV):

x—linker 1—x    Formula IV b) in a suitable solvent to form a mixture; and
stirring the mixture obtained in step (a) under conditions to obtain said polymer.

According to another aspect, there is provided an antimicrobial gel comprising an oligomer of formula (I)

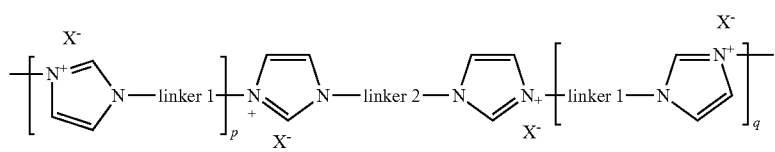

Formula (I)

wherein linker 1 is an alkyl-aryl-alkyl group or ($C_2$-$C_8$) alkene;
p and q are independently an integer from 2 to 6, that is 2, 3, 4, 5, or 6;
linker 2 is

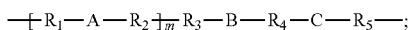

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is halide selected from fluoride, chloride and bromide.

DEFINITIONS

The following words and terms used herein shall have the meaning indicated:

The term 'oligomer' as used herein refers to an oligomer whose molecules consist of relatively few repeating units, up to five in total of the same repeating units i.e. a repeating unit may be imidazolium, linker 1 or linker 2 of Formula (I), linker 1 or linker 2 of Formula (II), Formula (I), Formula (II) or any combinations thereof.

The term 'polymer' as used herein refers to a large molecule, or macromolecule, composed of many repeated units, up 30 in total of the same repeating units i.e. a repeating unit may be imidazolium, linker 1 or linker 2 of Formula (II), Formula (II) or any combinations thereof.

The term "degradation" as used herein refers to the ability of a compound to decompose under certain conditions, especially complex substances such as polymers and proteins, by stages, exhibiting well-defined intermediate products. During the degradation process, it is the conversion of the active oligomers to less active degradation product(s) that is indicative of the changes to the MIC values. Upon the degradation process, these intermediate products derived from the degradation process will be labelled as degradation products. These certain conditions can be neutral and/or basic conditions.

"Alkyl" as a group or part of a group refers to a straight or branched aliphatic hydrocarbon group to be interpreted broadly, having from 1 to 16 carbon atoms, eg, 1, 2, 3, 4, 5, 6, 7, 8, 9, 10, 11, 12, 13, 14, 15 or 16 carbon atoms, preferably a C1-01$_6$ alkyl, C1-012 alkyl, more preferably a $C_1$-$C_{10}$ alkyl, most preferably $C_1$-$C_6$ alkyl unless otherwise noted. Examples of suitable straight and branched alkyl substituents include but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 5-methylheptyl, 1-methylheptyl, octyl, nonyl, decyl, undecyl, 2,2,3-trimethyl-undecyl, dodecyl, 2,2-dimethyl-dodecyl, tridecyl, 2-methyl-tridecyl, 2-methyl-tridecyl, tetradecyl, 2-methyl-tetradecyl, pentadecyl, 2-methyl-pentadecyl, hexadecyl, 2-methyl-hexadecyl and the like. The alkyl may be optionally substituted with one or more groups as defined under the term "optionally substituted" below.

"Aryl" as a group or part of a group to be interpreted broadly denotes (i) an optionally substituted monocyclic, or fused polycyclic, aromatic carbocycle (ring structure having ring atoms that are all carbon) preferably having from 5 to 12 atoms per ring, wherein the optionally substitution can be di-substitution, or tri-substitution. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group. The aryl may be optionally substituted with one or more groups as defined under the term "optionally substituted" below.

"Alkyloxy" or "alkoxy" refers to an alkyl-O-group to be interpreted broadly in which alkyl is as defined herein. The alkyloxy is a $C_1$-$C_{16}$ alkyloxy, $C_1$-$C_{12}$ alkyloxy, more preferably a $C_1$-$C_{10}$ alkyloxy, most preferably $C_1$-$C_6$ alkyloxy. Examples include, but are not limited to, methoxy and ethoxy. The group may be a terminal group or a bridging group. The term alkyloxy may be used interchangeably with the term "alkoxy". The alkyloxy or alkoxy may be optionally substituted with one or more groups as defined under the term "optionally substituted" below.

"Amine" refers to groups to be interpreted broadly of the form —$NR_aR_bR_c$ wherein $R_a$, $R_b$ and $R_c$ are individually selected from the group including but not limited to hydrogen, optionally substituted alkyl, optionally substituted carbonyl, optionally substituted alkenyl, and optionally substituted aryl groups. Wherein "amine" is a terminal group, the bridging group as used herein will be assumed as "amino" group that refers to groups of the form —$NR_aR_b$ wherein $R_a$ and $R_b$ are individually selected from the group including but not limited to hydrogen, optionally substituted alkyl, optionally substituted carbonyl, optionally substituted alkenyl, and optionally substituted aryl groups.

A "bond" is a linkage between atoms in a compound or molecule. The bond may be a single bond, a double bond, or a triple bond.

"Halide" or "halogen" represents chlorine, fluorine, bromine or iodine.

"Heteroalkyl" refers to a straight- or branched-chain alkyl group to be interpreted broadly, having from 1 to 16 carbon atoms, eg, 1, 2, 3, 4, 5, 6, 7, 8, 9, 10, 11, 12, 13, 14, 15 or 16 carbon atoms, preferably a $C_1$-$C_{16}$ alkyl, $C_1$-$C_{12}$ alkyl, more preferably a $C_1$-$C_{10}$ alkyl, most preferably $C_1$-$C_6$ alkyl unless otherwise noted, wherein one or more of carbon atoms has been replaced by a heteroatom selected from S, O, P and N. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group. The heteroalkyl may be optionally substituted with one or more groups as defined under the term "optionally substituted" below.

"Heteroaryl" either alone or part of a group refers to groups to be interpreted broadly containing an aromatic ring (preferably a 5 or 6 membered aromatic ring) having one or more heteroatoms as ring atoms in the aromatic ring with the remainder of the ring atoms being carbon atoms. The aromatic rings may be monocyclic, fused or bridged or spiro polycyclic ring fused with another aromatic ring (preferably a 5 or 6 membered aromatic ring). Suitable heteroatoms include nitrogen, oxygen and sulphur. Examples of heteroaryl include tetrazolyl, triazolyl, pyrimidinyl, pyrazinyl, thiophenyl, furanyl, indazolyl, benzoxazolyl, benzofuranyl, benzothiophenyl, indolyl, pyrrolyl, oxazolyl, pyrazolyl, thiazolyl, quinolinyl, imidazolyl, purinyl, oxadiazolonyl. A heteroaryl group is typically a $C_1$-$C_{18}$ heteroaryl group. A heteroaryl group may comprise 3 to 8 ring atoms. A heteroaryl group may comprise 1 to 3 heteroatoms independently selected from the group consisting of N, O and S. The group may be a terminal group or a bridging group. The heteroaryl may be optionally substituted with one or more groups as defined under the term "optionally substituted" below.

The term "optionally substituted" as used herein means the group to which this term refers may be unsubstituted, or may be substituted with one or more groups independently selected from alkyl, alkenyl, alkynyl, thioalkyl, cycloalkyl, cycloalkylalkyl, cycloalkenyl, cycloalkylalkenyl, heterocycloalkyl, cycloalkylheteroalkyl, cycloalkyloxy, cycloalkenyloxy, cycloamino, halo, carboxyl, haloalkyl, haloalkynyl, alkynyloxy, heteroalkyl, heteroalkyloxy, hydroxyl, hydroxyalkyl, alkoxy, thioalkoxy, alkenyloxy, haloalkoxy, haloalkenyl, haloalkynyl, haloalkenyloxy, nitro, amino, nitroalkyl, nitroalkenyl, nitroalkynyl, nitroheterocyclyl, alkylamino, dialkylamino, alkenylamine, aminoalkyl, alkynylamino, acyl, alkyloxy, alkyloxyalkyl, alkyloxyaryl, alkyloxycarbonyl, alkyloxycycloalkyl, alkyloxyheteroaryl, alkyloxyheterocycloalkyl, alkenoyl, alkynoyl, acylamino, diacylamino, acyloxy, alkylsulfonyloxy, heterocyclic, heterocycloalkenyl, heterocycloalkyl, heterocycloalkylalkyl, heterocycloalkylalkenyl, heterocycloalkylheteroalkyl, heterocycloalkyloxy, heterocycloalkenyloxy, heterocycloxy, heterocycloamino, haloheterocycloalkyl, alkylsulfinyl, alkylsulfonyl, alkylsulfenyl, alkylcarbonyloxy, alkylthio, acylthio, aminosulfonyl, phosphorus-containing groups such as phosphono and phosphinyl, sulfinyl, sulfinylamino, sulfonyl, sulfonylamino, aryl, heteroaryl, heteroarylalkyl, heteroarylalkenyl, heteroarylheteroalkyl, heteroarylamino, heteroaryloxy, arylalkenyl, arylalkyl, alkylaryl, alkylheteroaryl, aryloxy, arylsulfonyl, cyano, cyanate, isocyanate, —C(O)NH(alkyl), and —C(O)N(alkyl)$_2$. Where the term "substituted" is used, the group to which this term refers to may be substituted with one or more of the same groups mentioned above.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Detailed Disclosure of Optional Embodiments

Exemplary, non-limiting embodiments of an oligomer of formula (I) will now be disclosed.

The oligomer may be of formula (I)

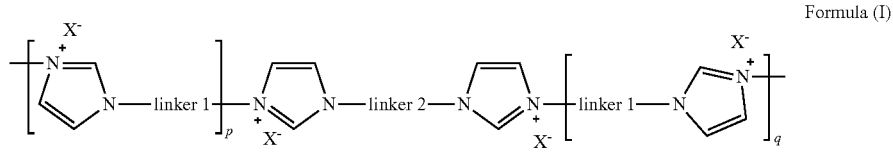

Formula (I)

wherein linker 1 is an alkyl-aryl-alkyl group or $(C_2-C_8)$ alkene;

p and q is independently an integer from 2 to 6, that is 2, 3, 4, 5, or 6;

linker 2 is

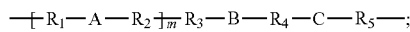

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is a halide selected from fluoride, chloride and bromide.

In the oligomer of formula (I), linker 1 may be an alkyl-aryl-alkyl group. The alkyl-aryl-alkyl group may be $C_{1-6}$alkyl-phenyl-$C_{1-6}$alkyl. The $C_{1-6}$alkyl group may be methyl, ethyl, propyl, butyl, pentyl or hexyl. The $C_{1-6}$alkyl-phenyl-$C_{1-6}$alkyl may be selected from the group consisting of o-xylene, m-xylene, p-xylene. In the oligomer of formula (I), linker 1 may be an alkene group. Linker 1 may be $(C_2-C_8)$alkene group. The aryl group may also be in general optionally substituted.

In the oligomer of formula (I), p and q may be independently an integer from 2 to 6, that is 2, 3, 4, 5, or 6.

In the oligomer of formula (I), linker 2 may be

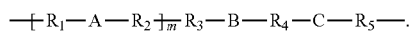

The m integer may be 0 or 1. A of linker 2 may be independently aryl or heteroaryl. The aryl may be selected from the group consisting of o-xylene, m-xylene, p-xylene. B of linker 2 may be independently O, N or S. C of linker 2 may be independently aryl or heteroaryl. The aryl may be selected from the group consisting of o-xylene, m-xylene, p-xylene. $R_1$ of linker 2 may be a bond or alkyl. $R_2$ of linker 2 may be a bond, alkoxy or amine. The amine may be an amino group when it is a terminal group. $R_3$ of linker 2 may be carbonyl, bond or alkyl. $R_4$ of linker 2 may be bond or alkyl; $R_5$ may be alkyl. Linker 2 may preferably be selected from the group consisting of

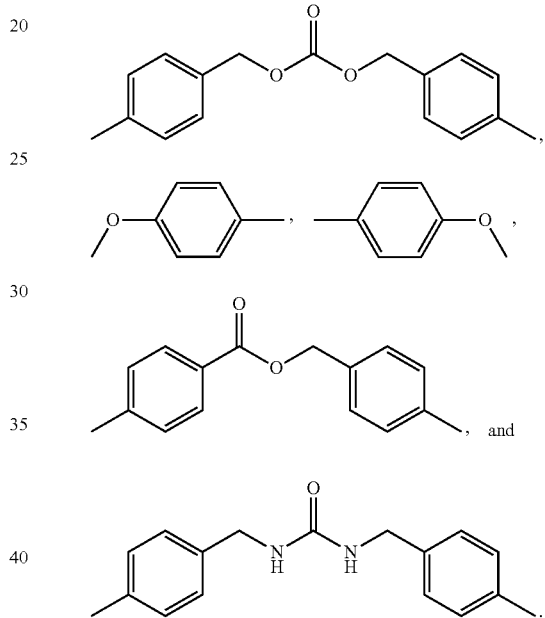

The aryl group may also be in general optionally substituted.

In the oligomer of formula (I), X may be a halogen from Group VII of the periodic table. X may be a halide selected from fluoride, chloride and bromide.

In the oligomer of formula (I), the oligomer may comprise of a terminal group. The terminal group may be an alkyl. The alkyl group may be $C_{1-14}$-alkyl. The alkyl group may be methyl, ethyl, propyl, butyl, pentyl, hexyl, heptyl, octyl, nonyl, decyl, undecyl or dodecyl. The alkyl group may preferably be $—C_8H_{17}$.

The oligomer of formula (I) may be selected from the group consisting of

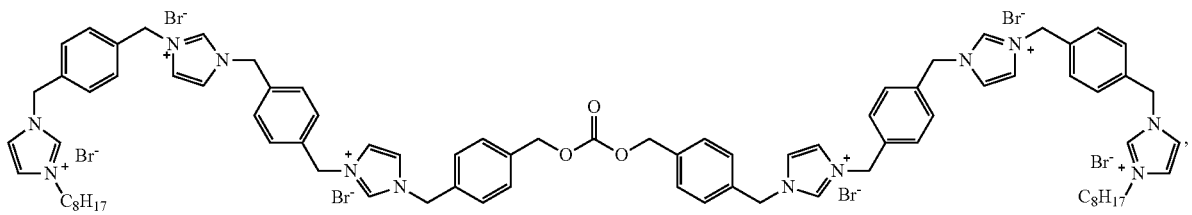

-continued

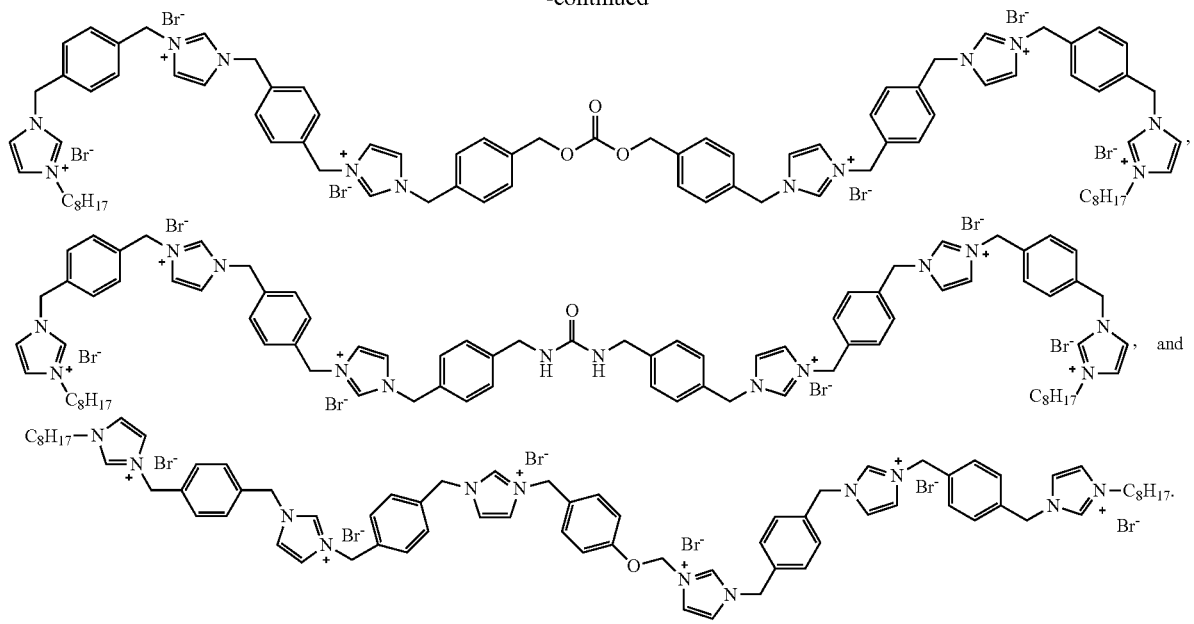

Exemplary, non-limiting embodiments of an oligomer or a polymer of formula (II) will now be disclosed.

The oligomer or a polymer may be of formula (II)

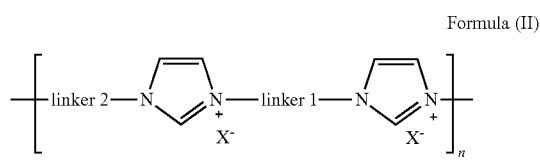

Formula (II)

wherein linker 1 is an alkyl-aryl-alkyl group or ($C_2$-$C_8$) alkene;

n is an integer from 3 to 30 that is 3, 4, 5, 6, 7, 8, 9, 10, 11, 12, 13, 14, 15, 16, 17, 18, 19, 20, 21, 22, 23, 24, 25, 26, 27, 28, 29 or 30;

linker 2 is

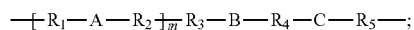

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is a halide selected from fluoride, chloride and bromide.

In the oligomer or a polymer of formula (II), linker 1 may be an alkyl-aryl-alkyl group. The alkyl-aryl-alkyl group may be $C_{1-6}$alkyl-phenyl-$C_{1-6}$alkyl. The $C_{1-6}$alkyl group may be methyl, ethyl, propyl, butyl, pentyl or hexyl. The $C_{1-6}$alkyl-phenyl-$C_{1-6}$alkyl may preferably be selected from the group consisting of o-xylene, m-xylene, p-xylene. In the oligomer or a polymer of formula (II), linker 1 may be an alkene group. Linker 1 may be ($C_2$-$C_8$)alkene group. Linker 1 may preferably be $C_4$alkene group. The aryl group may also be in general optionally substituted.

In the oligomer or a polymer of formula (II), n may be an integer from 3 to 30 that is 3, 4, 5, 6, 7, 8, 9, 10, 11, 12, 13, 14, 15, 16, 17, 18, 19, 20, 21, 22, 23, 24, 25, 26, 27, 28, 29 or 30.

In the oligomer or a polymer of formula (II), linker 2 may be

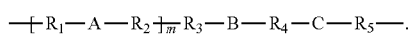

The m integer may be 0 or 1. A of linker 2 may be independently aryl or heteroaryl. The aryl may be selected from the group consisting of o-xylene, m-xylene, p-xylene. B of linker 2 may be independently O, N or S. C of linker 2 may be independently aryl or heteroaryl. The aryl may be selected from the group consisting of o-xylene, m-xylene, p-xylene. $R_1$ of linker 2 may be a bond or alkyl. $R_2$ of linker 2 may be a bond, alkoxy or amine. The amine may be an amino group when it is a terminal group. $R_3$ of linker 2 may be carbonyl, bond or alkyl. $R_4$ of linker 2 may be bond or alkyl; $R_5$ may be alkyl. Linker 2 may preferably be selected from the group consisting of

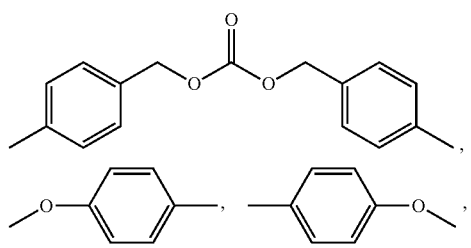

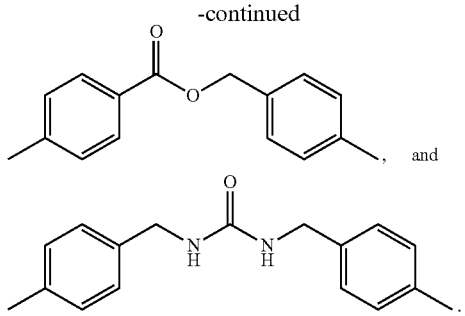
, and

The aryl group may also be in general optionally substituted.

In the oligomer or a polymer of formula (II), X may be a halogen from Group VII of the periodic table. X may be a halide selected from fluoride, chloride and bromide.

In the oligomer or a polymer of formula (II), the polymer may have a terminal group selected from the group consisting of linker 2, an imidazolium ring, an imidazole and a combination thereof. The terminal group(s) may be the same as each other, or may be different from each other. The terminal group may be an imidazolium ring at one end of the polymer and another terminal group may be a "linker 2 conjugated to an imidazolium ring" at the other end of the polymer.

The oligomer of formula (I) may be capable of being cleaved at linker 2. The oligomer or the polymer of formula (II) may be capable of being cleaved at linker 2. Where cleaving of linker 2 is achieved under neutral or basic conditions. The neutral conditions may be at a pH of 7. The basic conditions may be at a pH value of more than 7, that is pH 8, pH 9, pH 10, pH 11, pH 12, H 13 and pH 14. Where the oligomer of formula (I) or the oligomer or the polymer of formula (II) is being cleaved, the cleaved portion may be inactive against a microbe.

The polymer of Formula (II) may be selected from the group consisting of

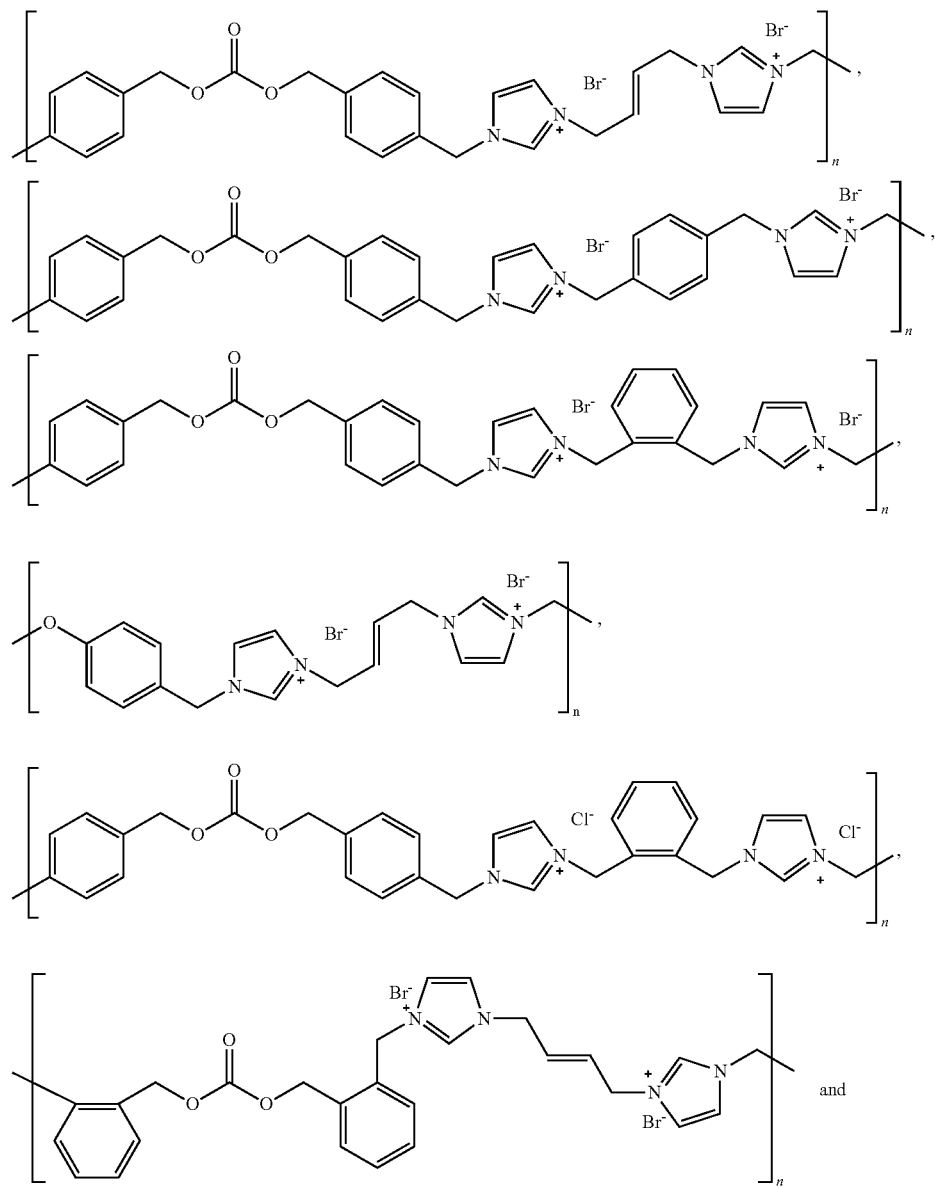

-continued

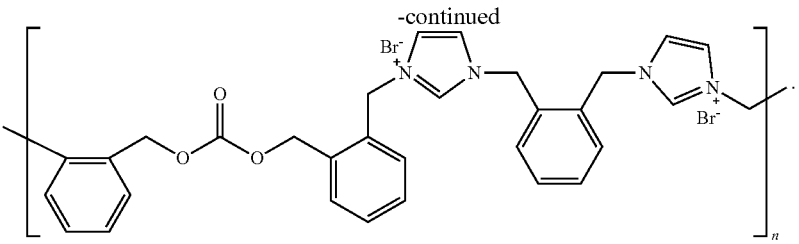

Exemplary, non-limiting embodiments of an antimicrobial composition will now be disclosed.

The antimicrobial composition may comprise of the oligomer of formula (I). The antimicrobial composition may comprise of the oligomer or a polymer of formula (II).

The antimicrobial composition as defined herein may be for use in inhibiting microbial activity. The antimicrobial composition as defined herein may be for use in treating a microbial infection or disease.

Advantageously, the antimicrobial composition as defined herein may display an excellent antimicrobial activity against a broad range of microbes. More advantageously, the oligomer may be degradable and may have non-resistance property. The oligomer described herein may have a degradation profile that can be tuned under different conditions.

The antimicrobial composition as defined herein may inhibit the activity or treats the infection or disease caused by a microbe that is selected from the group consisting of Staphylococcus aureus, Escherichia coli, Pseudomonas aeruginosa, Bacillus subtilius, Klebsiella pneumonia, Cryptococcus neoformans and Candida albicans. When the microbe is contacted with the antimicrobial composition at a defined concentration, the microbial activity of said microbe may be reduced to in the range of about 1% to about 0.1%, in the range of about 0.5% to about 0.1%, in the range of about 1% to about 0.5%, preferably to about 0.5%, more preferably to about 0.1%. The defined concentration of the antimicrobial composition may be in the range of about 1 μg/ml to about 100 μg/ml, about 1 μg/ml to about 10 μg/ml, about 1 μg/ml to about 20 μg/ml, about 1 μg/ml to about 50 μg/ml, about 5 μg/ml to about 10 μg/ml, about 5 μg/ml to about 20 μg/ml, about 5 μg/ml to about 50 μg/ml, about 5 μg/ml to about 100 μg/ml, about 10 μg/ml to about 20 μg/ml, about 10 μg/ml to about 50 μg/ml, about 10 μg/ml to about 100 μg/ml, about 50 μg/ml to about 100 μg/ml, about 50 μg/ml to about 60 μg/ml, about 50 μg/ml to about 70 μg/ml, about 50 μg/ml to about 80 μg/ml, about 50 μg/ml to about 90 μg/ml, about 60 μg/ml to about 100 μg/ml, about 70 μg/ml to about 100 μg/ml, about 80 μg/ml to about 100 μg/ml, about 90 μg/ml to about 100 μg/ml, or preferably about 60 μg/ml to about 65 μg/ml. The reduction of the microbial activity may be achieved within a duration of about 0.5 minutes to about 120 minutes, about 0.5 minutes to about 1 minute, about 1 minute to about 2 minutes, about 0.5 minutes to about 2 minutes, about 1 minute to about 10 minutes, about 1 minute to about 20 minutes, about 1 minute to about 30 minutes, about 1 minute to about 60 minutes, about 1 minute to about 120 minutes, about 2 minutes to about 10 minutes, about 2 minutes to about 30 minutes, about 2 minutes to about 60 minutes, about 2 minutes to about 120 minutes, about 5 minutes to about 10 minutes, about 5 minutes to about 30 minutes, about 5 minutes to about 60 minutes, about 5 minutes to about 120 minutes, about 10 minutes to about 60 minutes, about 30 minutes to about 60 minutes, or about 60 minutes to about 120 minutes or preferably about 0.5 minutes to about 2 minutes.

The microbe may not be resistant to said antimicrobial composition. Advantageously, this means that the antimicrobial composition may not suffer from antimicrobial resistance. More advantageously, it may not be necessary to increase the dosage or concentration of the oligomer or polymer when used against the same microbe on the same surface or subject for a long period of time. Hence, the antimicrobial composition may be used against microbes that have developed a resistance to conventional antimicrobial drugs.

Exemplary, non-limiting embodiments of a use of the antimicrobial composition as defined herein will now be disclosed.

There is provided use of the antimicrobial composition as defined herein in the manufacture of a medicament for treating a microbial infection or disease. The microbial infection or disease may be caused by a microbe that is selected from the group consisting of Staphylococcus aureus, Escherichia coli, Pseudomonas aeruginosa, Bacillus subtilius, Klebsiella pneumonia, Cryptococcus neoformans and Candida albicans.

Exemplary, non-limiting embodiments of a method of inhibiting a microbial activity or treating a microbial infection or disease will now be disclosed.

The method of inhibiting a microbial activity or treating a microbial infection or disease may comprise administering the antimicrobial composition as defined herein to a subject or applying the antimicrobial composition as defined herein on a surface. The antimicrobial composition may inhibit the activity or treats the infection or disease caused by a microbe that is selected from the group consisting of Staphylococcus aureus, Escherichia coli, Pseudomonas aeruginosa, Bacillus subtilius, Klebsiella pneumonia, Cryptococcus neoformans and Candida albicans.

The subject may be a cell. The subject may be a human or animal body. The cell may be present in a cell culture in vitro. The cell may be from a cell line. The cell line may be an immortalized cell line, a genetically modified cell line or a primary cell line. The cell may be from a tissue of a subject. The cell may be in a subject.

The surface may be a surface of a cell. The surface may be a surface on the human body or animal body.

The surface may be the surface of an inanimate object and hence, where the method of inhibiting a microbial activity involves applying the antimicrobial composition as defined herein on a surface, the method may not be regarded as a method of treatment. Here, the antimicrobial composition may be a disinfectant or an antimicrobial sanitizer that is applied to the surface of an inanimate object for general disinfection or sterilization.

The method of inhibiting or method of treating may preferably be an in vitro method. The method of inhibiting or method of treating may also be an in vivo method.

The method of inhibiting a microbial activity in a cell may comprise administering the antimicrobial composition as defined herein to a cell as defined herein. The method of treating a microbial infection or disease in a cell may comprise administering the antimicrobial composition as defined herein to a cell as defined herein.

The microbe may be contacted with the antimicrobial composition at a defined concentration, the microbial activity may be reduced to in the range of about 1% to about 0.1%, in the range of about 0.5% to about 0.1%, in the range of about 1% to about 0.5%, preferably to about 0.5%, more preferably to about 0.1%. The defined concentration of the antimicrobial composition may be in the range of about 1 μg/ml to about 100 μg/ml, about 1 μg/ml to about 10 μg/ml, about 1 μg/ml to about 20 μg/ml, about 1 μg/ml to about 50 μg/ml, about 5 μg/ml to about 10 μg/ml, about 5 μg/ml to about 20 μg/ml, about 5 μg/ml to about 50 μg/ml, about 5 μg/ml to about 100 μg/ml, about 10 μg/ml to about 20 μg/ml, about 10 μg/ml to about 50 μg/ml, about 10 μg/ml to about 100 μg/ml, about 50 μg/ml to about 100 μg/ml, about 50 μg/ml to about 60 μg/ml, about 50 μg/ml to about 70 μg/ml, about 50 μg/ml to about 80 μg/ml, about 50 μg/ml to about 90 μg/ml, about 60 μg/ml to about 100 μg/ml, about 70 μg/ml to about 100 μg/ml, about 80 μg/ml to about 100 μg/ml, about 90 μg/ml to about 100 μg/ml, or preferably about 60 μg/ml to about 65 μg/ml.

Exemplary, non-limiting embodiments of a method of producing an oligomer of formula (I) will now be disclosed.

The method of producing the oligomer of formula (I)

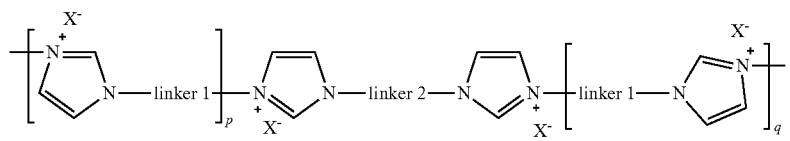

Formula (I)

wherein linker 1 is an alkyl-aryl-alkyl group or ($C_2$-$C_8$) alkene;

p and q are independently an integer from 2 to 6 that is 2, 3, 4, 5 or 6;

linker 2 is

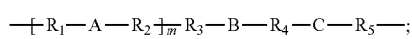

m is 0 or 1;

A is independently aryl or heteroaryl;

B is independently O, N or S;

C is independently aryl or heteroaryl;

$R_1$ is a bond or alkyl;

$R_2$ is a bond, alkoxy or amine;

$R_3$ is carbonyl, bond or alkyl;

$R_4$ is bond or alkyl;

$R_5$ is alkyl;

X is halide selected from fluoride, chloride and bromide, said method may comprise of the steps of:

a) providing a di-imidazole unit bearing linker 2 of Formula (III)

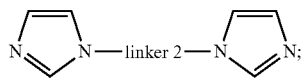

Formula (III)

b) mixing the di-imidazole of Formula (III) with an imidazolium salt that is dissolved in a suitable solvent to form a mixture; and c) stirring the mixture obtained in step (b) under conditions to obtain said oligomer.

Formula (III) in step (a) of the method as defined herein may be selected from the group consisting of

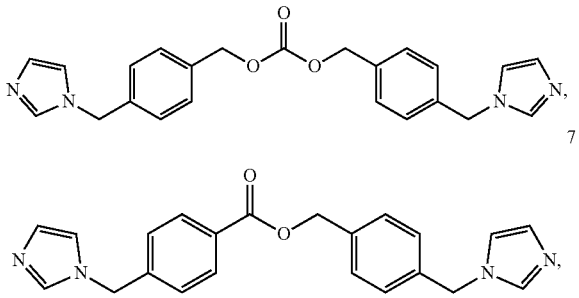

-continued

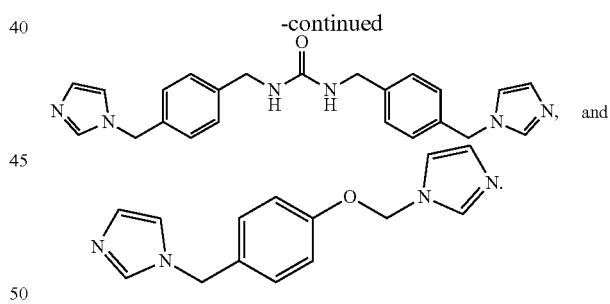

The imidazolium salt in step (b) of the method as defined herein may be selected from the group consisting of bisimidazolium salt, trisimidazolium salt, tetraimidazolium salt, pentaimidazolium salt and hexaimidazolium salt.

The solvent in step (b) of the method as defined herein may be an organic solvent. The organic solvent may be a polar aprotic solvent. The polar aprotic solvent may be selected from the group consisting of dimethylformamide (DMF), dimethyl sulfoxide (DMSO), acetone and acetonitrile.

The condition as mentioned in step (c) of the method as defined herein may comprise of a temperature in the range of about 20° C. to about 30° C., about 20° C. to about 22° C., about 20° C. to about 25° C., about 25° C. to about 30° C., about 28° C. to about 30° C. or preferably about 22° C. to about 28° C.

The condition as mentioned in step (c) of the method as defined herein may be undertaken for a time period in the range of about 18 hours to 60 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, about 50 hours, about 52 hours, about 54 hours, about 56 hours, about 58 hours, about 60 hours, preferably about 24 hours or more preferably about 48 hours.

Exemplary, non-limiting embodiments of a method of preparing the oligomer or the polymer of Formula (II) will now be disclosed.

The method of preparing the oligomer or the polymer of Formula (II)

Formula (II)

wherein linker 1 is an alkyl-aryl-alkyl group or ($C_2$-$C_8$) alkene;

n is an integer from 3 to 30 that is 3, 4, 5, 6, 7, 8, 9, 10, 11, 12, 13, 14, 15, 16, 17, 18, 19, 20, 21, 22, 23, 24, 25, 26, 27, 28, 29 or 30;

linker 2 is $$-\!\!\!\!+\!R_1-A-R_2\!\!\!+_{\overline{m}}\!R_3-B-R_4-C-R_5-\!\!;$$

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is halide selected from fluoride, chloride and bromide, said method may comprise of the steps of:

a) mixing a di-imidazole unit bearing linker 2 of Formula (III):

Formula III with a precursor bearing linker 1 of Formula (IV):

x—linker 1—x        Formula IV in a suitable solvent to form a mixture; and
b) stirring the mixture obtained in step (a) under conditions to obtain said polymer.

Formula (III) in step (a) of the method as defined herein may be selected from the group consisting of Formula (IV) in step (a) of the method as defined herein may be selected from the group consisting of The solvent in step (a) of the method as defined herein may be an organic solvent. The organic solvent may be a polar aprotic solvent. The polar aprotic solvent may be selected from the group consisting of dimethylformamide (DMF), dimethyl sulfoxide (DMSO), acetone and acetonitrile.

The condition as mentioned in step (b) of the method as defined herein may comprise of a temperature in the range of about 20° C. to about 30° C., about 20° C. to about 22° C., about 20° C. to about 25° C., about 25° C. to about 30° C., about 28° C. to about 30° C. or preferably about 22° C. to about 28° C.

The condition as mentioned in step (b) of the method as defined herein may be undertaken for a time period in the range of about 30 minutes to about 48 hours, about 30 minutes, about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, preferably about 1 hour, preferably about 12 hours or more preferably about 48 hours.

The condition as mentioned in step (b) of the method as defined herein may optionally further comprise of the step of heating said mixture. The heating temperature of said mixture may be in the range of about 40° C. to about 80° C., about 40° C. to about 45° C., about 40° C. to about 50° C., about 40° C. to about 55° C., about 40° C. to about 60° C., about 40° C. to about 65° C., about 40° C. to about 70° C., about 40° C. to about 75° C., about 40° C. to about 80° C., about 45° C. to about 80° C., about 50° C. to about 80° C., about 55° C. to about 80° C., about 60° C. to about 80° C., about 65° C. to about 80° C., about 70° C. to about 80° C., about 75° C. to about 80° C., preferably about 65° C. or more preferably about 70° C.

Exemplary, non-limiting embodiments of an antimicrobial gel will now be disclosed.

The antimicrobial gel may comprise of an oligomer of formula (I)

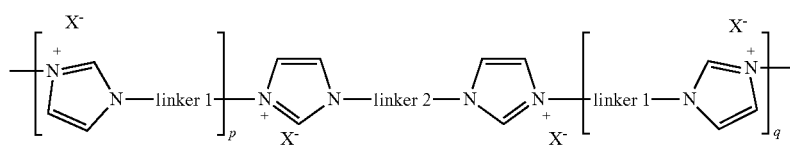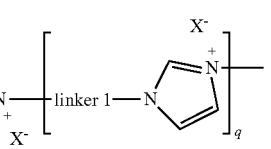

Formula (I)

wherein linker 1 is an alkyl-aryl-alkyl group or $(C_2-C_8)$ alkene;

p and q are independently an integer from 2 to 6 that is 2, 3, 4, 5, or 6;

linker 2 is

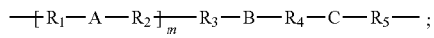

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, bond or alkyl;
$R_4$ is bond or alkyl;
$R_5$ is alkyl; and
X is halide selected from fluoride, chloride and bromide.

The gel as defined herein may be formed in alcohol. The alcohol may be selected from the group consisting of ethanol, methanol, n-propanol and n-butanol.

Other applications of the polymeric composition will be discussed further below.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the killing efficiency for IBN-C8, IBN-CC8 and IBN-EC8 against E. coli at 62 µg/ml after long time (FIG. 1A) and short time incubation (FIG. 1B). * indicates that no colony was observed. The data are expressed as mean±S.D. of triplicates.

FIG. 2 is a series of Scanning Electron Microscopy (SEM) images of E. coli and S. aureus treated with degradable oligomers (4MIC) for 2 minutes. Bacteria grew in MHB media were used as controls. Cell wall became disrupted and dissolved after exposure to degradable oligomers. Scale bars represent 1 µm.

FIG. 3 shows the degradation profiles of IBN-CC8 (4 mg/ml) in Sorenson's phosphate buffer (pH 6, 7, 8; 100 mM, FIG. 3A) and tris buffer solution (pH 8; 10 mM, 100 mM, FIG. 3B).

FIG. 4 shows the degradation profile of IBN-EC8 (4 mg/ml) in Sorenson's phosphate buffer (pH 6, 7, 8; 100 mM).

FIG. 5 shows a series of changes of MIC for IBN-CC8 in (FIG. 5A) tris buffer (pH 8) and (FIG. 5B) saline solution (0.85% NaCl) against E. coli and S. aureus; and in Sorenson's phosphate buffer (pH 6, 7 and 8) against E. coli (FIG. 5C) and S. aureus (FIG. 5D).

FIG. 6 shows a series of changes of MIC for IBN-CC8, IBN-EC8 and IBN-UC8 in saline solution (0.85% NaCl) against E. coli (FIG. 6A) and S. aureus (FIG. 6B).

FIG. 7 shows a series of changes of MIC for IBN-EC8 in phosphate buffer (pH 6, 7 and 8) against E. coli (FIG. 7A) and S. aureus (FIG. 7B) and changes of MIC for IBN-UC8 in in phosphate buffer (pH 6, 7 and 8) against E. coli (FIG. 7C) and S. aureus (FIG. 7D).

FIG. 8 demonstrates a resistance acquisition in the presence of sub-MIC levels of several degradable oligomers (IBN-CC8, IBN-EC8, IBN-HC8, IBN-UC8) and vancomycin against S. aureus.

FIG. 9 shows a series of images: FIG. 9A is an image of IBN-HC8 gels formed in EtOH (1.5%), n-PrOH (1.0 wt %), and n-BuOH (1.0 wt %); FIG. 9B is an Scanning Electron Microscopy (SEM) image of IBN-HC8 gel in ethanol (5 wt %).

FIG. 10 shows a storage and loss moduli of IBN-CC8 (4.0 wt %, FIG. 10A) and IBN-HC8 (2.0 wt %, FIG. 10B) in alcohols obtained from a strain-amplitude sweep performed at 10 rad/s.

FIG. 11 shows a storage and loss moduli of IBN-CC8 (4.0 wt %, FIG. 11A) and IBN-HC8 (2.0 wt %, FIG. 11B) in alcohols obtained from a temperature ramp performed at 2% strain and 5% strain, respectively. The heating rate was 2° C./min.

FIG. 12 shows a storage and loss moduli of IBN-CC8 (4.0 wt %, FIG. 12A) and IBN-HC8 (2.0 wt %, FIG. 12B) obtained from an angular frequency sweep performed at 2% strain and 5% strain, respectively.

FIG. 13 shows the viscosity as a function of the shear rate for gels of IBN-HC8 (2.0 wt %) in alcohols.

FIG. 14 shows the agar well diffusion assays of degradable imidazolium oligomers IBN-HC8, IBN-EC8 and IBN-CC8 at concentrations of 0.5% w/v in (FIG. 14A) ethanol compared to commercial ethanol-based Hygin-X Antiseptic Handrub, and (FIG. 14B) glycerol compared to vancomycin and chloroxylenol.

FIG. 15 shows the five polymers with a carbonate linkage that demonstrated high antimicrobial activity when tested against the four microbes while their respective degradation products were inactive. See Table 3 for the test results.

FIG. 16 shows the killing efficiency for IBN-CP3 and IBN-CP3-Cl against *E. coli* at 4 µg/ml. The data are expressed as mean±S.D. of triplicates.

FIG. 17 shows the degradation profiles of IBN-CP1 (FIG. 17A) and IBN-CP3 (4 mg/ml, FIG. 17B) in Sorenson's phosphate buffer (pH 6, 7, 8; 100 mM).

FIG. 18 shows the degradation profile of IBN-CP3-Cl (4 mg/ml) in Sorenson's phosphate buffer (pH 6, 7, 8; 100 mM).

FIG. 19 shows a series of changes in activity of IBN-CP1 in phosphate buffer (pH 6, 7 and 8) and seawater (pH 8) against *E. coli* (FIG. 19A) and *S. aureus* (FIG. 19B) and changes in activity of IBN-CP3 in phosphate buffer (pH 6, 7 and 8) and seawater (pH 8) against *E. coli* (FIG. 19C) and *S. aureus* (FIG. 19D).

FIG. 20 shows the resistance acquisition in the presence of sub-MIC levels of degradable carbonate polymers IBN-CP1 and IBN-CP3 and norfloxacin against *S. aureus*.

FIG. 21 shows the analysis of the $^1$H NMR spectrum of purified polymers, in terms of the number of imidazole and imidazolium units per chain, was calculated based on the ratio of imidazolium ($\delta$9.3-9.6 ppm) to imidazole ($\delta$6.9 or 7.2 ppm) integral values.

EXAMPLES

Non-limiting examples of the invention will be further described in greater detail by reference to specific Examples, which should not be construed as in any way limiting the scope of the invention.

LIST OF ABBREVIATIONS USED

ACN: acetonitrile
AcOEt: ethyl acetate
AcOH: acetic acid
NH$_4$Cl: Ammonium chloride
AUC: area under the curve
Brine: saturated aqueous solution of NaCl
bs: broad signal (broad peak) $^1$H NMR
cat.: catalyst
Cs$_2$CO$_3$: Cesium carbonate
CH$_2$Cl$_2$ or DCM: Methylene chloride or Dichloromethane
DBU: 1,8-Diazabicycloundec-7-ene
DCC: N,N'-Dicyclohexylcarbodiimide
DI water: deionized water
DMAP: 4-Dimethylaminopyridine
DMF: N,N-dimethylformamide
DMSO: dimethylsulfoxide
DMSO-d$_6$: per-deuterated dimethylsulfoxide
Ether: diethylether
EtOH: ethanol
HPLC: high pressure liquid chromatography
IPA: Iso-propanol (2-propanol)
KOH: Potassium hydroxide
L: litre(s)
LiAlH$_4$: Lithium aluminium hydride
LC-MS: Liquid chromatography-mass spectrometry
Me: methyl
MeOH: methanol
m.p.: melting point
MS: mass spectrometry
NBS: N-Bromosuccinimide
Et$_3$N: triethylamine
Na$_2$CO$_3$: Sodium carbonate
NaHCO$_3$: Sodium bicarbonate
NaH: Sodium hydride
NaOH: Sodium hydroxide
Na$_2$SO$_4$: Sodium sulphate
NIS: N-iodosuccinimide
NMM: N-methylmorpholine
NMR: Nuclear Magnetic Resonance
Pd(dppf)Cl$_2$: [1,1'-Bis(diphenylphosphino)ferrocene]dichloropalladium(II)
Rt: room temperature
TBAF: Tetra-butyl-ammonium iodide
TEA: triethylamine
THF: tetrahydrofuran
TLC: thin layer chromatography
TMS: trimethylsilyl
SOCl$_2$: Thionyl chloride

Materials and Methods

All anhydrous solvents were purchased from Sigma-Aldrich Corp. (St. Louis, Mo., U.S.A.) and used without further purification. All other reagents were used as received, except where otherwise noted in the text below.

Analytical thin layer chromatography (TLC) was performed using Merck 60 F-254 silica gel plates with visualization by ultraviolet light (254 nm) and/or heating the plate after staining with a solution of 20% KMnO4 w/v in H$_2$O. Flash column chromatography was carried out on Kieselgel 60 (0.040-0.063 mm) supplied by Merck (Burlington, Mass., U.S.A.) under positive pressure.

$^1$H and $^{13}$C nuclear magnetic resonance (NMR) spectra were recorded on Bruker AV-400 (400 MHz) spectrometer. Chemical shifts ($\delta$) are reported in parts per million (ppm) with the residual solvent peak of tetramethylsilane used as the internal standard at 0.00 ppm. $^1$H NMR data are reported in the following order: chemical shift, multiplicity (br=broad, s=singlet, d=doublet, t=triplet, q=quartet and m=multiplet), coupling constants (J, Hz), integration and assignment. High resolution mass spectra (HRMS) were recorded on a Bruker MicroTOF-Q system. The samples were directly injected into the chamber at 20 µL·minutes$^{-1}$. Typical instrument parameters: capillary voltage, 4 kV; nebulizer, 0.4 bars; dry gas, 2 L·minutes$^{-1}$ at 120° C.; m/z range, 40- 3000.

Example 1—Antimicrobial Studies

Minimum Inhibitory Concentration

*Staphylococcus aureus* (ATCC 6538, Gram-positive), *Escherichia coli* (ATCC 8739, Gram-negative), *Pseudomonas aeruginosa* (Gram-negative), and *Candida albicans* (ATCC 10231, fungus) were used as representative microorganisms to challenge the antimicrobial functions of the imidazolium salts. All bacteria and fungus were stored frozen at −80° C., and were grown overnight at 37° C. in Mueller Hinton Broth (MHB) prior to experiments. Fungus was grown overnight at 22° C. in Yeast Mold (YM) broth. Subsamples of these cultures were grown for a further 3 hours and diluted to give an optical density value of 0.07 at 600 nm, corresponding to $3\times10^8$ CFU mL$^{-1}$ for bacteria and $10^6$ CFU mL$^{-1}$ for fungus (McFarland's Standard 1; confirmed by plate counts).

The oligomers were dissolved in MHB or YM broth at a concentration of 4 mg mL$^{-1}$ and the minimal inhibitory concentrations (MICs) were determined by microdilution assay. Bacterial solutions (100 µL, $3\times10^8$ CFU mL$^{-1}$) were mixed with 100 µL of oligomer solutions (normally ranging from 4 mg mL$^{-1}$ to 2 µg mL$^{-1}$ in serial two-fold dilutions) in each well of the 96-well plate. The plates were incubated at 37° C. for 24 hours with constant shaking speed at 300 rpm. The MIC measurement against *Candida albicans* is similar to bacteria except that the fungus solution is $10^6$ CFU mL$^{-1}$ in YM and the plates were incubated at room temperature.

The minimum inhibitory concentrations were taken as the concentration of the antimicrobial oligomer at which no microbial growth was observed with the microplate reader. PBS solution containing microbial cells alone were used as negative controls. The assay was performed in four replicates and the experiments were repeated at least two times.

Resistance Studies

The method was adapted from that of Yang and co-authors with modification [K. Fukushima, S. Liu, H. Wu, A. C. Engler, D. J. Coady, H. Maune, J. Pitera, A. Nelson, N. Wiradharma, S. Venkataraman, Y. Huang, W. Fan, J. Y. Ying, Y. Y. Yang, J. L. Hedrick. Nature Comm, 2013, 4:2861]. Drug resistance was induced by treating *S. aureus* repeatedly with degradable oligomers. First MICs of the tested oligomers were determined against *S. aureus* using the broth microdilution method. Then serial passaging was initiated by transferring bacterial suspension grown at the sub-MIC of the oligomers (½ of MIC at that passage) and was subjected to another MIC assay. After 24 hours incubation period, cells grown at the sub-MIC of the test compounds/antibiotics were once again transferred and assayed for MIC. The MIC against *S. aureus* was tested for 16 passages.

Drug-resistant behaviour of *S. aureus* was evaluated by recording the changes in the MIC normalized to that of the first passage. Conventional antibiotics vancomycin was used as the control.

Time Kill Kinetics

The microbes were treated with oligomers at 4MIC concentration, and samples were taken out of each well at different intervals. 100 µL of cell suspension was removed, rescued by a series of 10- fold dilutions with growth medium. For plating, 100 µL of the diluted samples was spread on growth medium agar plates and colonies were counted after overnight incubation at 37° C.

Monitoring the Changes of Antimicrobial Activity during Degradation

The changes of antimicrobial activity during degradation were monitored by measuring MIC during the process. The degradable oligomers were dissolved in Sorenson's phosphate buffer (pH 6.0, 7.0, 8.0, 100 mM), tris buffer (pH 8.0, 100 mM), and saline solutions. Stock solutions were 4 mg/ml. The solution was stored at 25° C. and the MIC against *E.coli* and *S. aureus* were measured at different intervals.

Well Diffusion Assay

The degradable oligomers were dissolved in ethanol and glycerol at 0.5% w/v concentration. Agar plates were inoculated with bacteria and 6 mm wells were cut, into which 20 µL of solution was added. Plates were inoculated at 37° C. for 24 hours and zone of inhibitions measured using a pair of vernier calipers.

Haemolysis

Fresh rat red blood cells (RBCs) were diluted with PBS buffer to give an RBC stock suspension (4 vol % blood cells). A 100 µL aliquot of RBC suspension was added into a 96-well plate containing 100 µL oligomer solutions of various concentrations (ranging from 4 mg mL$^{-1}$ to 2 µg mL$^{-1}$ in serial two-fold dilutions in PBS). After 1 hour incubation at 37° C., the contents of each well were pipetted into a micro-centrifuge tube and centrifuged at 2000 rpm for 5 minutes. Aliquots (100 µL) of the supernatant were transferred to a new 96-well plate. Haemolytic activity was determined as a function of haemoglobin release by measuring OD576 of 100 µL of the supernatant using a microplate reader (TECAN). A control solution that contained only PBS was used as a reference for 0% haemolysis. Absorbance of red blood cells lysed with 0.5% Triton-X was taken as 100% haemolysis. The data were expressed as mean and S.D. of four replicates, and the tests were repeated two times.

$$\% \text{ Haemolysis} = \frac{OD576(\text{oligomer}) - OD576(PBS)}{OD576(\text{Triton-X}) - OD576(PBS)} \times 100$$

Example 2—Degradable Imidazolium Oligomers

Evaluation of Antimicrobial Properties

The antimicrobial activities of novel imidazolium oligomers, polymers and their degradation products were evaluated against four different and clinically relevant microbes: *S. aureus, E. coli, P. aeruginosa,* and *C. albicans*. The toxicities of these compounds were also evaluated by measuring the extent of hemolysis induced by the oligomers and their degradation products. The minimum inhibitory concentration (MIC) values of all four oligomers are presented in Table 1. All four compounds were generally active against these microbes. IBN-CC8 displayed the lowest MIC value among the four oligomers which was similar to or slightly higher than (depending on microbe strain) the original IBN-C8 oligomer. Interestingly, carbonate oligomer IBN-CC8 also showed low toxicity with $HC_{10}$ greater than 2000 µg/ml. In contrast, degradation product (F1-CH2OH) of IBN-CC8 was essentially inactive against these microbes and did not induce hemolysis at the highest concentration measured (2000 µg/ml). All these results indicate that IBN-CC8 with carbonate linkage is the most promising degradable antimicrobial compound.

TABLE

Minimum inhibitory concentrations (MIC) of the degradable oligomers and their degradation products.

| Entry | Compound | MIC (μg/ml) | | | | $HC_{10}$ (μg/ml) |
|---|---|---|---|---|---|---|
| | | E. coli | S. aureus | P. aeruginosa | C. albicans | |
| 1 | IBN-CC8 | 8 | 8 | 125 | 31 | >2000 |
| 2 | IBN-EC8 | 8 | 16 | 31 | 125 | 1000 |
| 3 | IBN-UC8 | 8 | 8 | 500 | 62 | 2000 |
| 4 | IBN-HC8 | 8 | 16 | 125 | 125 | >2000 |
| 5 | F1-CH$_2$OH | 2000 | >2000 | 2000 | 250 | >2000 |
| 6 | F1-COOH | 31 | 62 | >2000 | 500 | — |
| 7 | F1-CH$_2$NH$_2$ | 16 | 125 | 250 | 62 | 1000 |
| 8 | Vancomycin | — | 2 | — | — | >2000 |

Time kill studies of the imidazolium oligomers IBN-CC8, IBN-EC8 and IBN-C8 against *E. coli* are shown in FIG. 1A and FIG. 1B. Generally, the new carbonate and ester-linked imidazolium oligomers displayed fast killing properties comparable to the first generation compound IBN-C8. More than 99% killing was observed within two minutes at concentrations of 62 μg/ml for all three compounds. As shown in scanning electron microscopy (SEM) images, bacterial cell walls were disrupted and subsequently dissolved following exposure to IBN-CC8, IBN-EC8 or IBN-HC8 for just two minutes (FIG. 2).

Degradation Profile

Theoretically, carbonate, ester, urea and hemiaminal linkers have different degradation pathways, products and conditions, with potential degradation products listed in Scheme 1.

Scheme 1. Possible degradation products of various imidazolium oligomers.

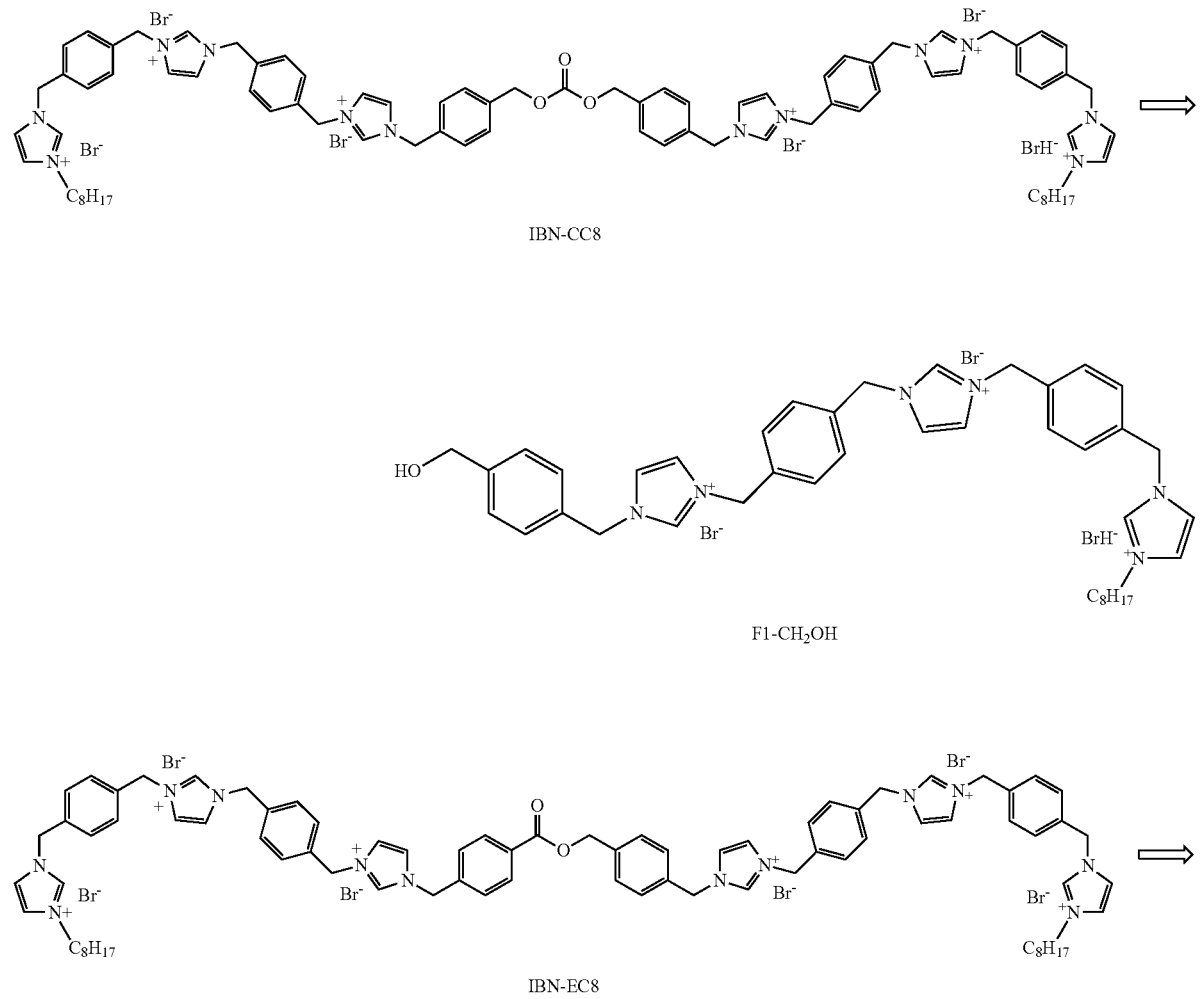

IBN-CC8

F1-CH$_2$OH

IBN-EC8

-continued
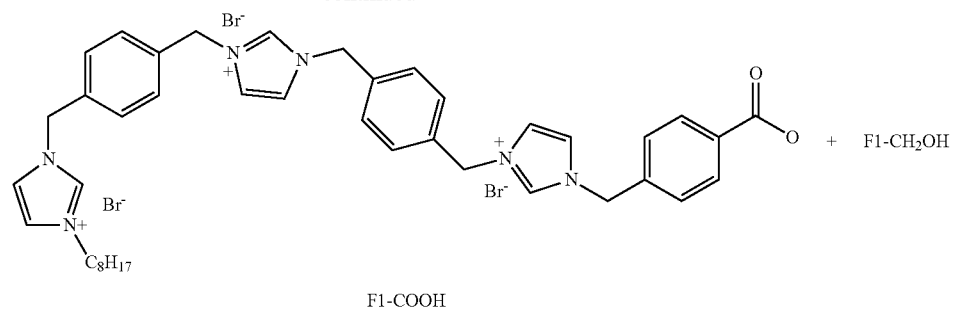
F1-COOH
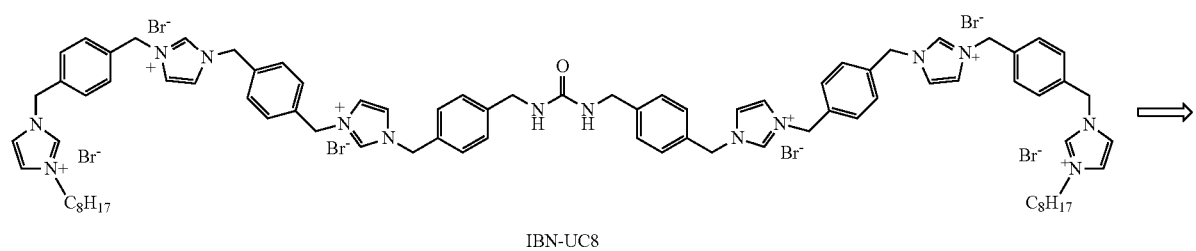
IBN-UC8
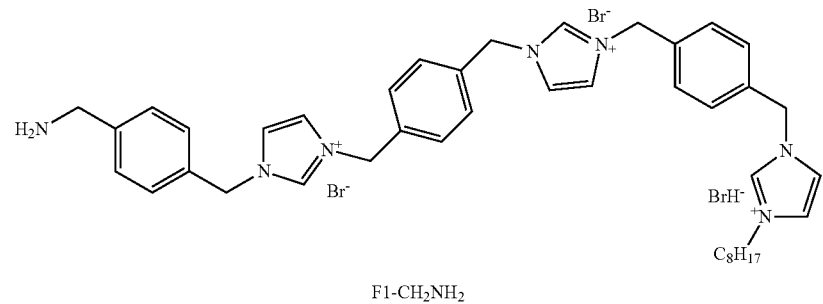
F1-CH2NH2
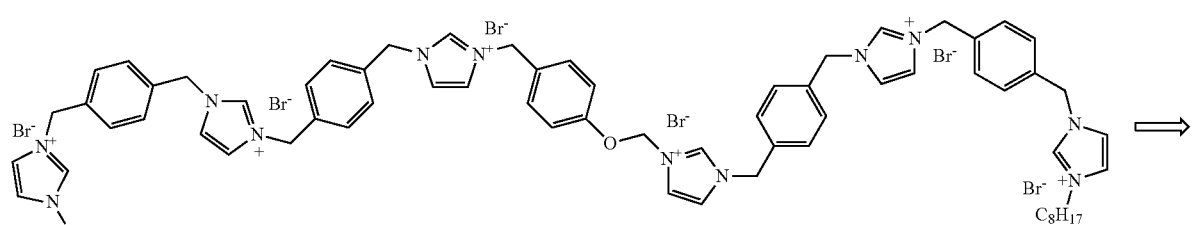
IBN-HC8

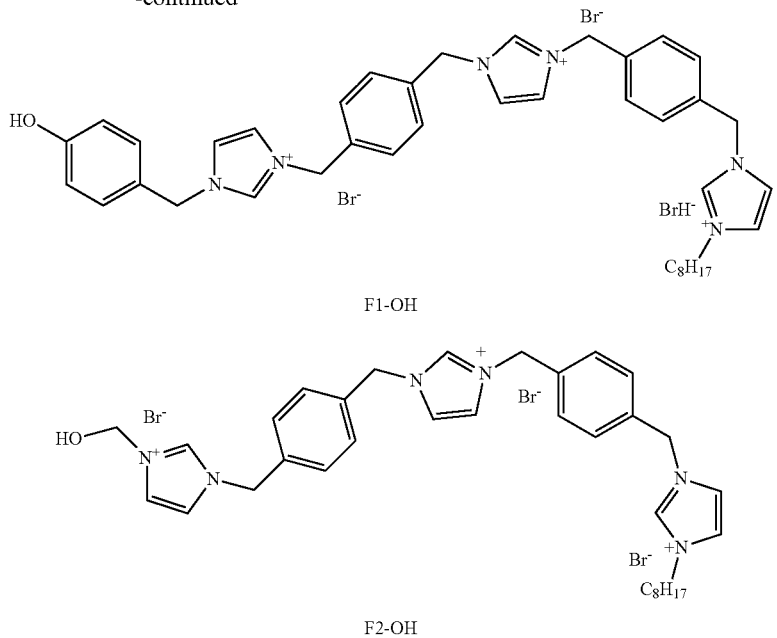

F1-OH

F2-OH

The degradation profiles of each linker were investigated under different conditions using NMR analysis. It was found that urea and hemiaminal oligomers, IBN-UC8 and IBN-HC8, were not significantly degraded in pH 6-8 buffered solutions under ambient conditions. Carbonate-linked oligomer (IBN-CC8) degraded under these conditions and the degradation rate was found to be sensitive to pH: the half-life of IBN-CC8 in Sorenson's phosphate buffer (100 mM) was about 18 days at pH 8, 90 days at pH 7, and >90 days at pH 6 (FIG. 3A). In addition, the degradation rate decreased when the buffer concentration was lowered (FIG. 3B). In essence, IBN-CC8 was stable under mildly acidic conditions and degraded at neutral and basic conditions. This property is desirable as bacterial infections generally cause the pH of the infection site to decrease to 6 and below. The carbonate-linked material would remain active in areas of bacterial infection, and only degrade gradually in the absence of bacterial infection. This material is particularly suitable for ocean agriculture as it would degrade in weeks (seawater pH value is around 8), ensuring no antimicrobial residues are retained in the ocean ecosystem after it has been employed for disinfection. Similarly, oligomer IBN-EC8 with an ester linkage degrades at pH 8 in Sorenson's phosphate buffer with a half-life of 17 days. However, this compound was more stable under neutral and acidic conditions (FIG. 4).

Over the course of degradation, conversion of the active oligomers to less active degradation product(s) is expected to be reflected in changes to the MIC values. To determine if this was indeed the case, IBN-CC8 was dissolved in buffer solution and its MIC values against *E. coli* and *S. aureus* were monitored at different time points (FIG. 5). The antimicrobial activity of a sample of IBN-CC8 in tris buffer (pH 8) against *E. coli* showed the most rapid decay, with MIC increasing from 8 µg/ml at day 0 to 32 µg/ml at day 3, eventually reaching 250 µg/ml at day 21. On the other hand, the MIC of IBN-CC8 in the same buffer against *S. aureus* quadrupled from 8 µg/ml to 32 µg/ml in 9 days, after which it remained constant for 35 more days (FIG. 5A). The antimicrobial activity of a sample of IBN-CC8 in saline solution (0.85% NaCl) against *E. coli* and *S. aureus* (FIG. 5B).

In Sorenson's phosphate buffer (pH 8), the MIC of IBN-CC8 against *E. coli* doubled from 32 µg/ml at day 0 to 64 µg/ml after 30 days (FIG. 5C). At pH 7, the MIC of IBN-CC8 against *E. coli* doubled after 32 days from 16 µg/ml to 32 µg/ml, and again at day 130 to 64 µg/ml. Further at pH 6, the MIC of IBN-CC8 against *E. coli* remained at 16 µg/ml for 110 days, after which it doubled to 32 µg/ml. Similar trends were observed for the MIC values of IBN-CC8 in phosphate buffer (pH 6, 7, 8) when tested against *S. aureus* (FIG. 5D). On the whole, these MIC changes are in good agreement with the degradation profile of IBN-CC8 in different pH buffer solutions (FIG. 5).

Drug Resistance Development Study

The potential for bacterial cells to develop resistance following multiple exposure to oligomers IBN-CC8, IBN-EC8, IBN-HC8 and IBN-UC8 and vancomycin was investigated by the serial passage of *S. aureus* under sub-MIC levels of each oligomer. MIC values were measured after each passage. As shown in FIG. 8, the MIC value of vancomycin increases at the 5th passage, and by the 16th passage the MIC value of vancomycin had quadrupled. In contrast, the MIC values of IBN-CC8, IBN-EC8 and IBN-UC8 remained unchanged over the entire 16 passages.

However, MIC increase was observed for IBN-HC8 at the 8$^{th}$ passage. These results indicated the lower propensity of bacteria to develop resistance toward the carbonate, ester and urea-linked antimicrobial imidazolium oligomers compared with vancomycin.

Gel Formation

In accordance to the previously reported main-chain imidazolium oligomers, these new imidazolium oligomers as defined herein also formed gels in alcohols (FIG. 9 to FIG. 13, Table 2).

TABLE 2

Critical gelation concentrations (wt %) of the degradable oligomers in alcohols.

| | ethanol | n-propanol | n-butanol |
|---|---|---|---|
| IBN-CC8 | 2.0 | 2.0 | x |
| IBN-EC8 | 2.0 | 1.5 | 1.5 |
| IBN-HC8 | 1.5 | 0.5 | 1.0 |

Antimicrobial Activity in Alcohol Solvents

The compatibility of degradable imidazolium oligomers IBN-HC8, IBN-EC8 and IBN-CC8 in alcohol solvents commonly employed for skin disinfection was evaluated by well diffusion assay. At concentrations of 0.5% w/v in ethanol, IBN-HC8 and IBN-EC8 elicited larger zones of inhibition than ethanol on its own against *E. coli* and *S. aureus*, and comparable zones of inhibition compared to ethanol against *P. aeruginosa* (FIG. 14A). The antibacterial activity of IBN-CC8 in ethanol against all three strains of bacteria that were tested exceeded that of commercial ethanol-based Hygin-X Antiseptic Handrub, which employs chlorhexidine gluconate (0.5% w/v) as an active ingredient.

Glycerol is included in some skin disinfectant products to prevent drying of skin, but has been reported to decrease the efficacy of alcohol-based hand disinfectants. When employed as a 0.5% w/v solution in glycerol, IBN-HC8 and IBN-EC8 displayed comparable efficacy against *E. coli, S. aureus* and *P. aeruginosa* as their solutions in ethanol (FIG. 14B), despite the lower antibacterial activity of glycerol on its own compared to ethanol. IBN-CC8 showed slightly diminished antibacterial activity when dissolved in glycerol compared to when it was dissolved in ethanol.

Example 3—Degradable Imidazolium Polymers

Evaluation of Antimicrobial Properties

All five polymers with a carbonate linkage demonstrated high antimicrobial activity when tested against the four microbes while their degradation products were inactive (Table 3 and FIG. 15). Among the five polymers, IBN-CP1-5, IBN-CP3 exhibited the best performance. IBN-CP3 had low MIC values against *E. coli, S. aureus* and *P. aeruginosa*, but higher MIC value against *C. Albicans* compared with non-degradable imidazolium polymer PIM-45. IBN-CP3 also demonstrated low toxicity with very minor hemolysis even at high concentration of 2000 µg/ml and its degradation product (F-diol3) did not show any activity against those microbes. IBN-CP3-Cl, with chloride replacing bromide as the counter anion, was prepared from carbonate linker and o-xylene dichloride. Compared to IBN-CP3, IBN-CP3-Cl displayed improved activity against Gram-negative bacteria *E. coli* and *P. aeruginosa* and fungus *C. Albicans*. Polymers of various sizes were prepared to study the effect of chain length on MIC values, the results of which are summarised in Tables 4 to 6.

TABLE 3

Minimum inhibitory concentrations (MIC) of imidazolium polymers and degradation products.

| | | MIC (µg/ml) | | | | HC$_{10}$ |
|---|---|---|---|---|---|---|
| Entry | Polymer | *E. coli* | *S. aureus* | *P. aeruginosa* | *C. albicans* | (µg/ml) |
| 1 | IBN-CP1 | 16 | 16 | 31 | 125 | 1000 |
| 2 | F-diol1 | >2000 | 125 | 2000 | >2000 | >2000 |
| 3 | IBN-CP2 | 31 | 31 | 62 | 125 | 500 |
| 4 | F-diol2 | >2000 | 2000 | >2000 | >2000 | >2000 |
| 5 | IBN-CP3 | 8 | 8 | 31 | 125 | 1000 |
| 6 | IBN-CP3-Cl | 4 | 8 | 16 | 31 | N.D. |
| 7 | F-diol3 | >2000 | 500 | >4000 | >2000 | >2000 |
| 8 | IBN-CP4 | 16 | 16 | 62 | 125 | >2000 |
| 9 | F-diol4 | 1000 | 250 | >2000 | >2000 | N.D. |
| 10 | IBN-CP5 | 16 | 16 | 125 | >125 | >2000 |
| 11 | F-diol5 | 250 | 125 | >2000 | >2000 | >2000 |
| 12 | IBN-HP | 31 | 62 | 31 | 31 | >2000 |
| 13 | PIM-45 | 8 | 8 | 31 | 31 | >2000 |

N.D. = not determined.

Time kill studies of the two most effective imidazolium polymers, IBN-CP3 and IBN-CP3-Cl were carried out against *E. coli*. Both polymers displayed fast killing properties even at low concentration of 4 µg/ml (FIG. 16). More than 99.9% killing was observed within 10 minutes and over 99.999% killing was observed after one hour.

TABLE 4

Minimum inhibitory concentrations (MIC) of IBN-CP1 with different chain lengths.

[Structure of IBN-CP1 polymer]

IBN-CP1

[Structure of F-diol1]

F-diol1

| Entry | Average Chain length /imid. units | MIC (ppm) EC | SA | PA | CA | $HC_{10}$ (ppm) | Solvent (temperature/ time)[a] |
|---|---|---|---|---|---|---|---|
| 1 | >200 | 62 | 62 | 62 | 125 | 125 | DMF (25° C., 48 h) |
| 2 | 36 | 31 | 31 | N.D. | N.D. | 500 | THF (120° C., 1 h) |
| 3 | 28 | 16 | 16 | 31 | 125 | N.D. | THF (65° C., 1 h) [b] |
| 4 | 27 | 16 | 16 | 31 | 125 | 1000 | THF (65° C., 1 h) [c] |
| 5 | 25 | 16 | 16 | N.D. | N.D. | N.D. | THF (65° C., 3 h) |
| 6 | 16 | 31 | 31 | N.D. | N.D. | 500 | THF (65° C., 1 h) |
| 7 | 15 | 31 | 31 | N.D. | N.D. | N.D. | THF (65° C., 3 h) |
| 8 | 14 | 31 | 31 | N.D. | N.D. | N.D. | THF (65° C., 0.5 h) |
| 9 | 12 | 125 | 125 | N.D. | N.D. | N.D. | THF (45° C., 1 h) |
| 10 | 6 | 125 | 62 | N.D. | N.D. | >2000 | THF (25° C., 3 h) |
| 11 | F-diol1 | >2000 | 125 | 2000 | >2000 | >2000 | — |

[a]Polymer was precipitated and washed with [b] acetone/ether (1:1) or [c] THF/ether (1:1); molar ratio of carbonate linker: trans-1,4,-dibromobutene = 5:4. N.D. = not determined.

TABLE 5

Minimum inhibitory concentrations (MIC) of IBN-CP3 with different chain lengths.

[Structure of IBN-CP3 polymer]

IBN-CP3

[Structure of F-diol3]

F-diol3

| Entry | Average Chain length/ imid. units | MIC (µg/ml) EC | SA | PA | CA | $HC_{10}$ (µg/ml) | Solvent (temperature/ time) |
|---|---|---|---|---|---|---|---|
| 1 | 43 | 8 | 8 | 31 | 125 | N.D. | MeCN (85° C., 1 h) |
| 2 | 18 | 8 | 8 | 31 | 125 | N.D. | THF (85° C., 1 h) |

TABLE 5-continued

Minimum inhibitory concentrations (MIC) of IBN-CP3 with different chain lengths.

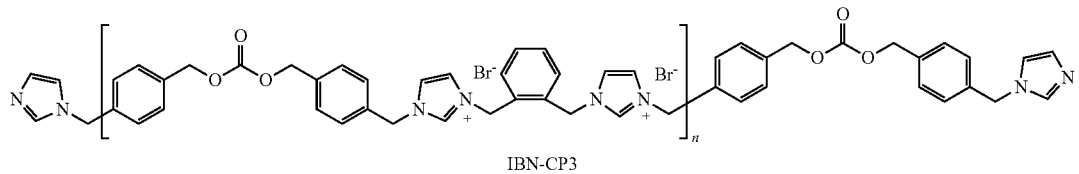

IBN-CP3

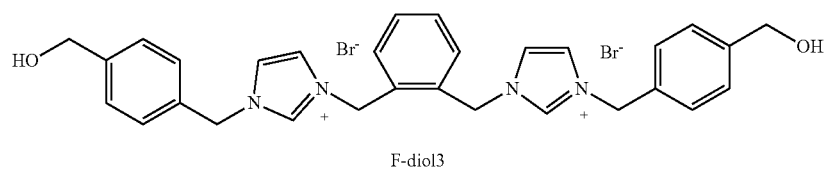

F-diol3

| Entry | Average Chain length/ imid. units | MIC (μg/ml) | | | | HC$_{10}$ (μg/ml) | Solvent (temperature/ time) |
|---|---|---|---|---|---|---|---|
| | | EC | SA | PA | CA | | |
| 3 | 11 | 8 | 8 | 31 | 125 | 1000 | THF (65° C., 1 h) |
| 4 | F-diol3 | >2000 | 500 | N.D. | >2000 | >2000 | — |

N.D. = not determined.

TABLE 6

Minimum inhibitory concentrations (MIC) of IBN-CP3-Cl with different chain lengths.

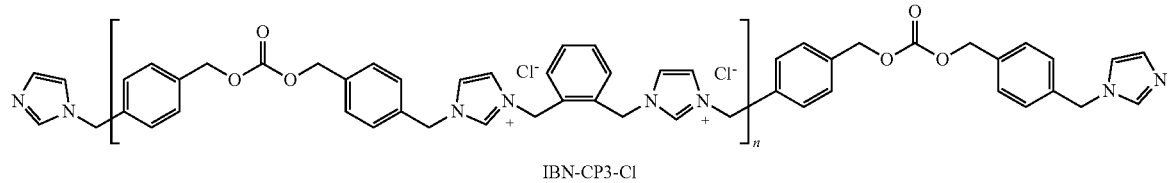

IBN-CP3-Cl

| Entry | N$_{im}$$^{a}$; carbonate degradation | MIC (μg/ml) | | | | Solvent (temperature/time) |
|---|---|---|---|---|---|---|
| | | EC | SA | PA | CA | |
| 1 | 31; 11% | 8 | 8 | 16 | 31 | MeCN (50° C., 12 h) |
| 2 | 70; 21% | 4 | 8 | 16 | 31 | MeCN (70° C., 12 h) |
| 3 | 12; 10% | 4 | 8 | 31 | 31 | MEK$^{b}$ (50° C., 12 h) |
| 4 | 16; 17% | 4 | 8 | 31 | 31 | THF (70° C., 12 h) |

N.D. = not determined; $^{a}$N$_{im}$ Average polymer chain length in imidazole(ium) units; $^{b}$MEK = methyl ethyl ketone.

Degradation Profile

Imidazolium polymers with carbonate linkages were also found to degrade at neutral and basic conditions. 50% of the carbonate linkages in IBN-CP1 degraded within 17 days at pH 8 (FIG. 17A). The degradation rate of IBN-CP3 was markedly slower compared to that of IBN-CP1 (FIG. 17B), which may be due to the more hydrophobic chain structure of the former. Poly-imidazolium with hemiaminal linker IBN-HP was stable under the conditions of this study.

Over the course of degradation, conversion of the active polymers to less active degradation products was expected to be reflected in changes to the MIC values. To determine if this was indeed the case, IBN-CP1 and IBN-CP3 were dissolved in buffer solution and their MIC values against E. coli and S. aureus were monitored at different time points (FIG. 19A to FIG. 19D). The relative activity of the polymer sample at a given point in time was expressed as a fraction of its MIC on Day 0 over its MIC at the point of measurement.

In Sorenson's phosphate buffer (pH 8), the activity of IBN-CP1 against S. aureus was halved after 14 days and was halved again at day 28 (FIG. 19B). By day 42, the activity of the degraded sample was just over 10% of the original polymer. When IBN-CP3 was subjected to similar conditions, its activity halved after 21 days, and again at day 48 (FIG. 19D). By day 90, the activity of the degraded sample was less than 10% of the original polymer. Similar trends in antimicrobial activity were observed for samples stored in seawater (pH 8). Both polymers showed higher stability under pH 6-7 conditions, retaining at least half their original activity by the end of the monitoring periods. On the whole, these MIC changes were in good agreement with the degradation profile of IBN-CP1 and IBN-CP3 in different pH buffer solutions (FIG. 17). FIG. 18 shows the degradation profile of IBN-CP3-Cl (4 mg/ml) in Sorenson's phosphate buffer (pH 6, 7, 8; 100 mM).

Drug Resistance Development Study

The potential for bacteria to develop resistance to carbonate polymers IBN-CP1 and IBN-CP3 were evaluated using the same procedure as for the oligomers. Fluoroquinolone antibiotic norfloxacin was adopted as a control. As shown in FIG. 20, the MIC value of norfloxacin increased at the 5th passage, and by the 15$^{th}$ passage the MIC value of norfloxacin against S. aureus was over 120 times its original value. In contrast, the MIC values of IBN-CP1 and IBN-CP3 remained unchanged over the entire 15 passages. Additionally, S. aureus grown in media containing degradation products F-diol1 or F-diol3 at concentrations of 2, 8, 16 and 100 μg/ml over the course of one month did not develop resistance to the polymers IBN-CP1 or IBN-CP3.

Example 4—Characterization of Gels

Preparation of the Gels

Gels were prepared by weighing the imidazolium oligomers directly into 4 mL glass vials and subsequently adding a known weight or volume of the solvent. The vials containing both the imidazolium and the solvent were either heated or sonicated to aid the dissolution process. The vials were left standing over night at ambient conditions. The gel state was evaluated by the stable-to-inversion-of-a-test-tube method. The critical gelation concentration (CGC) is defined as the lowest concentration of the gelator which leads to a stable gel.

Rheological Characterization of the Gels

Rheological measurements were performed with a control strain rheometer (ARES G2, U.S.A.) equipped with a plate-plate geometry of 8 mm diameter. Measurements were taken by equilibrating the gels at 25° C. between the plates at a gap of 1.0 mm. Strain-amplitude sweeps were performed at angular frequency of 10 rad/s. The shear storage modulus (G') and loss modulus (G") were measured at each point.

Frequency sweeps for IBN-CC8 (4.0 wt %) and IBN-HC8 (2.0 wt %) in alcohols were performed at strain amplitude of 2% and 5%, respectively, to ensure the linearity of viscoelasticity. The dynamic storage modulus (G') and loss modulus (G") were examined as a function of frequency from 0.1 to 100 rad/s. In addition, viscosity of the gel was also examined as a function of shear rate from 0.1 to 50/s.

To test the thermal stability of the gels, the storage and loss moduli of IBN-CC8 (4.0 wt %) and IBN-HC8 (2.0 wt %) in alcohols were measured from a temperature ramp performed at 2% strain and 5% strain, respectively. The heating rate was 2° C./min.

SEM Observation for Gels and Bacteria

The morphologies of the organogel microstructure were observed using a field emission SEM (JEOL JSM-7400F) operated at an accelerating voltage of 5 keV. The gels were dried via supercritical drying, and stored in under anhydrous conditions, either in a glovebox or a desiccator prior to imaging.

Bacterial cells (3×10$^8$ CFU/mL) grown in MHB without or with the oligomers at 4MIC for 2 minutes were collected and centrifuged at 5000 rpm for 5 minutes. The precipitates were washed twice with PBS buffer. Then the samples were fixed with glutaraldehyde (2.5%) for 2 hours followed by washing with DI water. Dehydration of the samples was performed using a series of ethanol/water solution (35%, 50%, 75%, 90%, 95% and 100%). The dehydrated samples were mounted on copper tape. After drying for 2 days, the samples were further coated with platinum for imaging with JEOL JSM-7400F (Japan) field emission scanning electron microscope operated at an accelerating voltage of 5 keV.

Statistical Analysis

Data are expressed as means ±standard deviation of the mean (S.D. is indicated by error bars). Student's t-test was used to determine significance among groups. A difference with P≤0.05 was considered statistically significant.

Example 5

Structural Design

The concept for the design of new imidazolium antimicrobial materials is to introduce degradable linkers in a manner that retains the excellent bactericidal properties of the imidazolium polymers and oligomers. To realize this target, key hydrophobic linkers were replaced with degradable functional groups while conserving the imidazolium main-chain. In the imidazolium oligomer series, the central o-xylene linker was replaced with a carbonate, hemiaminal, ester, or urea linker (Scheme 2a). In the imidazolium polymer series, either one of the butenyl- or xyl- linkers was replaced with a carbonate or hemiaminal linker (Scheme 2b). With these structural modifications, various novel imidazolium oligomers and polymers with degradable linkers were synthesized.

Scheme 2. Structural design of degradable imidazolium oligomers (a) and polymers (b).

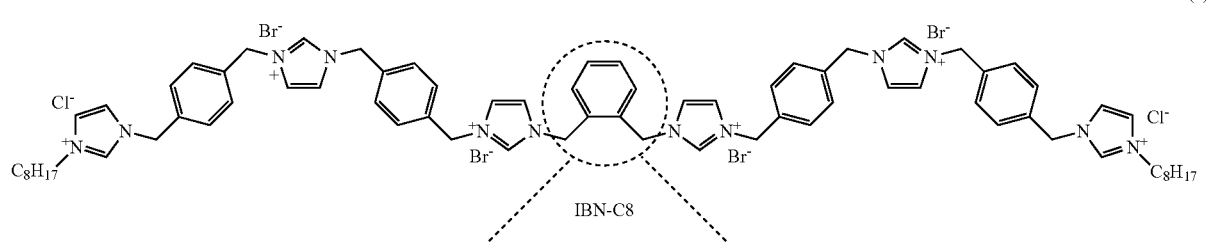

(a)

IBN-C8

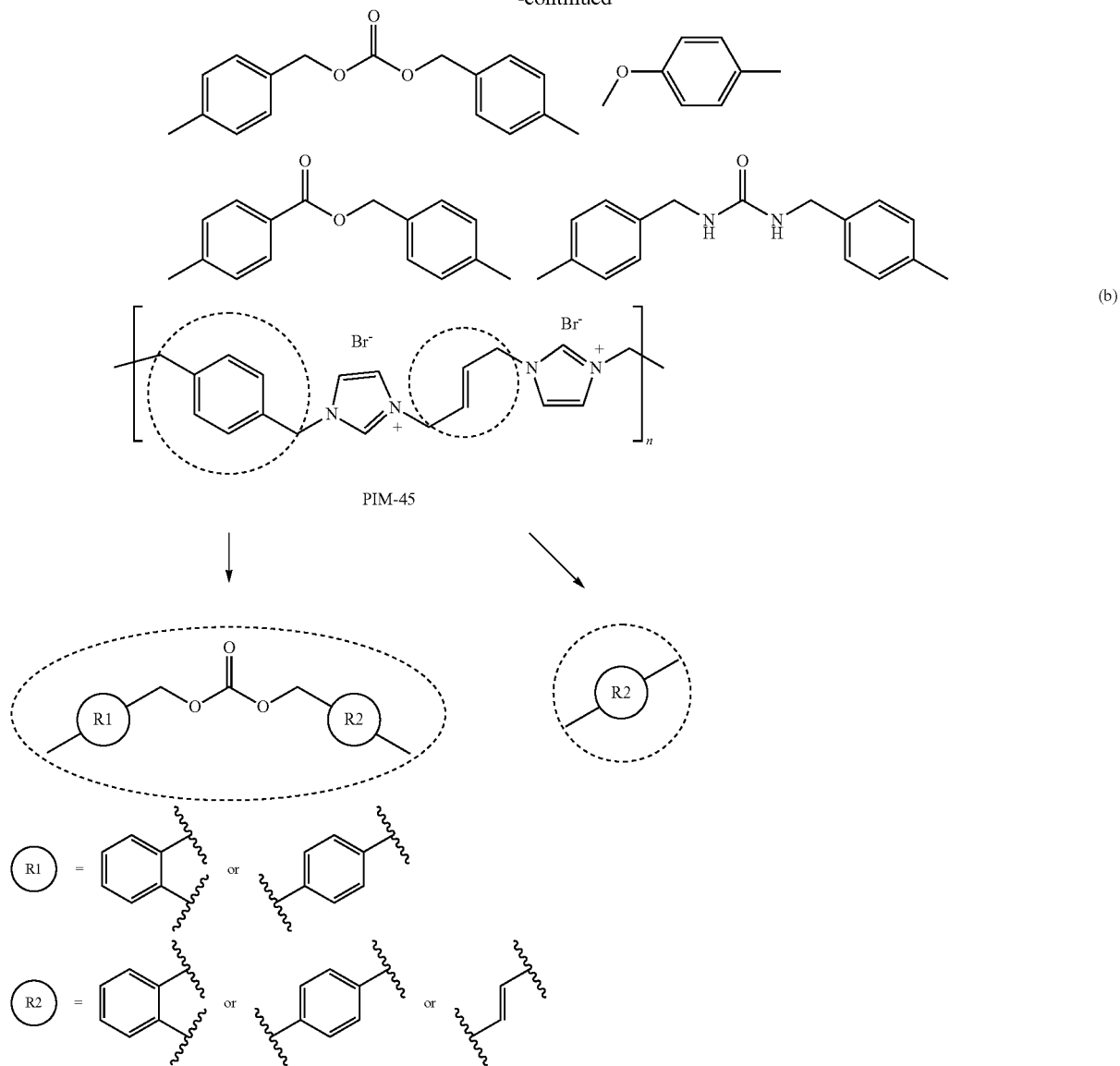
Materials Synthesis
The synthesis of new imidazolium oligomers started with the synthesis of di-imidazole units (Scheme 3, compounds 3, 7, 9 and 14) containing potential degradable linkers (Scheme 3).
Scheme 3.
Synthetic schemes of degradable di-imidazole linkers and fragments.
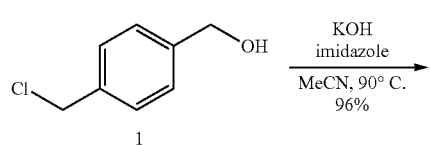
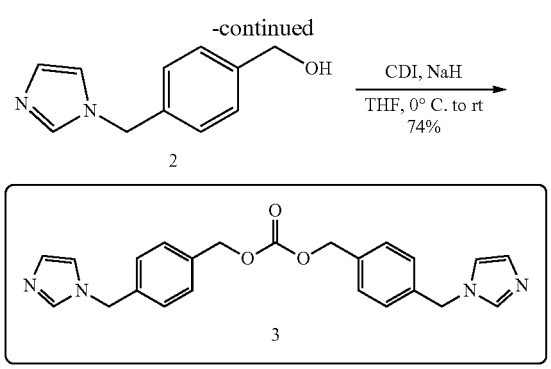
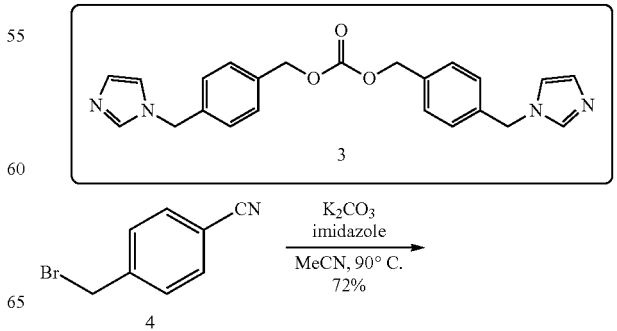

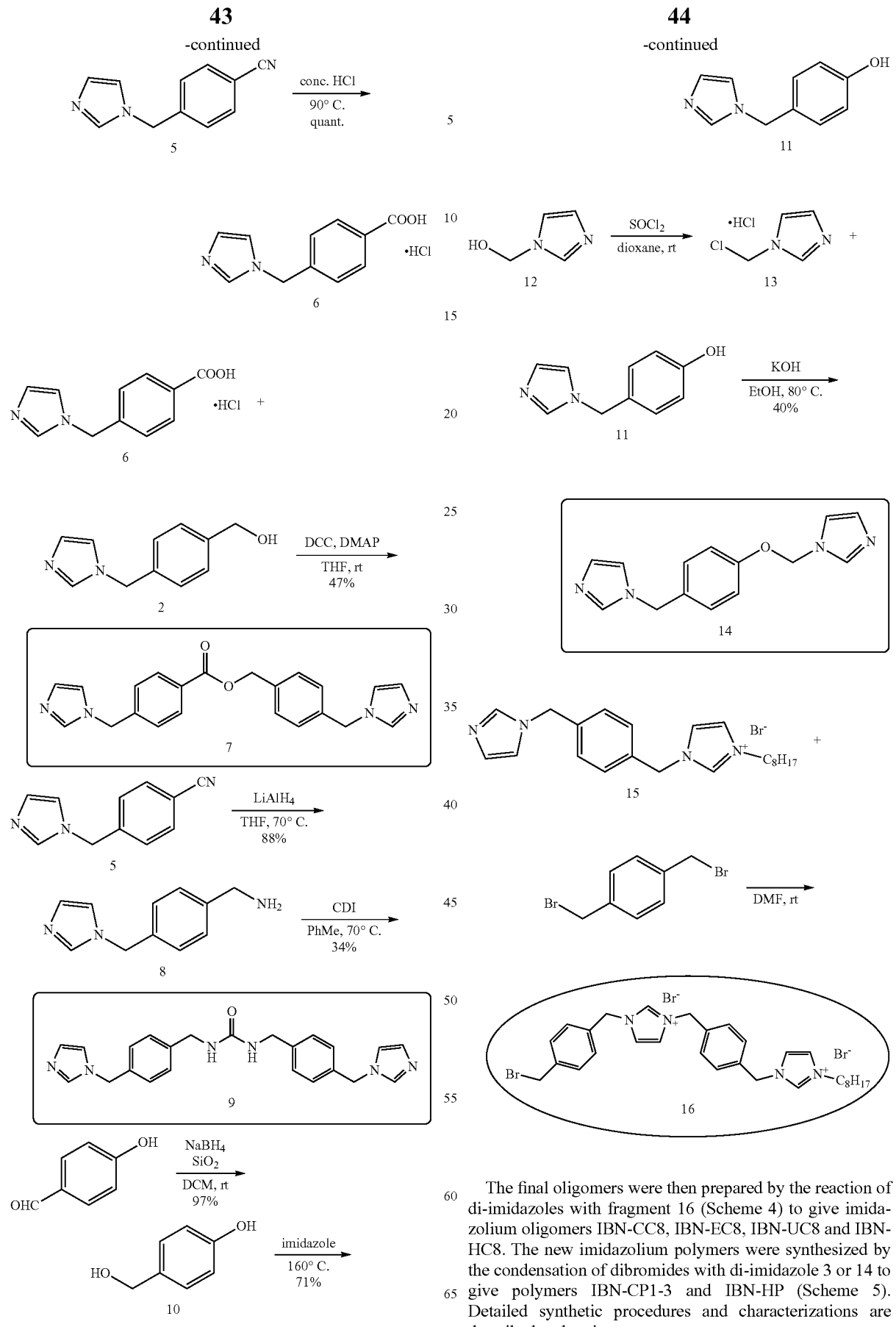

The final oligomers were then prepared by the reaction of di-imidazoles with fragment 16 (Scheme 4) to give imidazolium oligomers IBN-CC8, IBN-EC8, IBN-UC8 and IBN-HC8. The new imidazolium polymers were synthesized by the condensation of dibromides with di-imidazole 3 or 14 to give polymers IBN-CP1-3 and IBN-HP (Scheme 5). Detailed synthetic procedures and characterizations are described as herein.

Scheme 4. Synthetic schemes of degradable imidazolium oligomers.
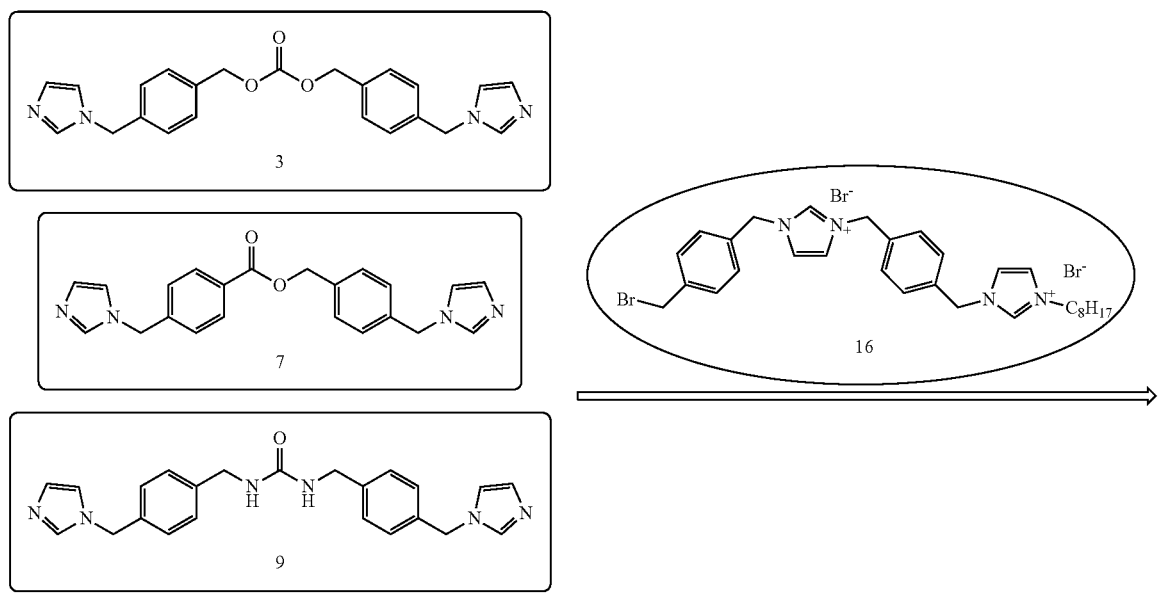
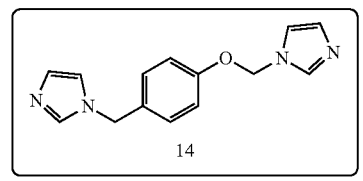
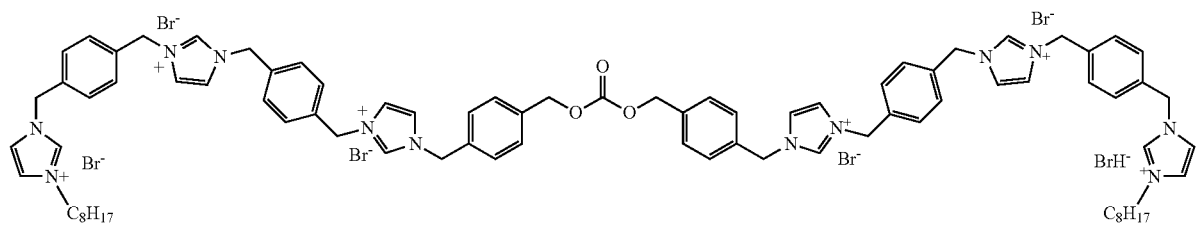
IBN-CC8
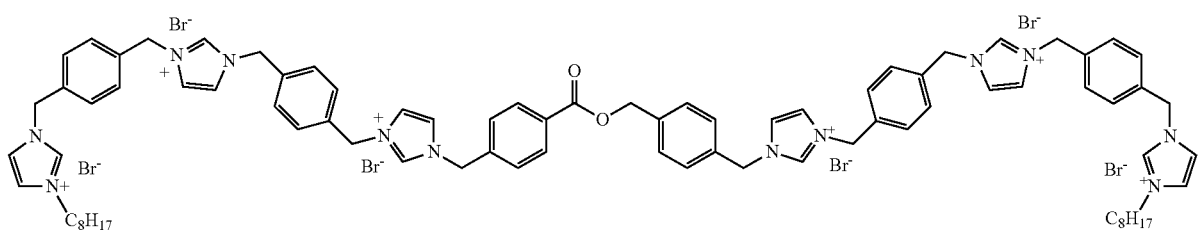
IBN-EC8

-continued
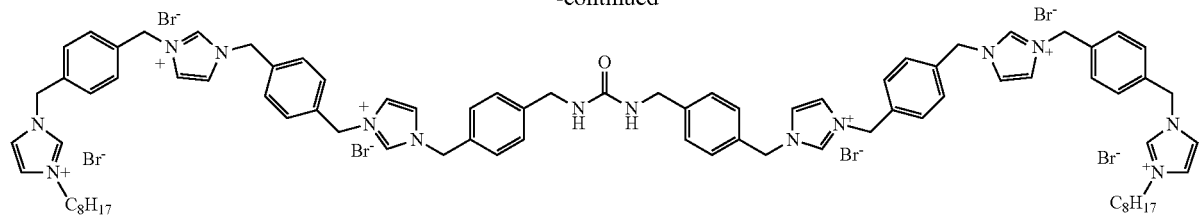
IBN-UC8
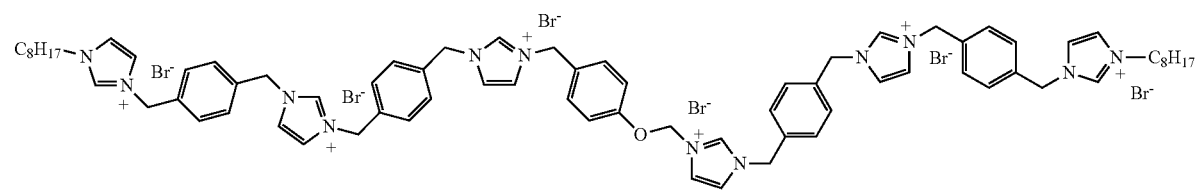
IBN-HC8
Scheme 5. Synthetic schemes of degradable imidazolium polymers with carbonate linker.
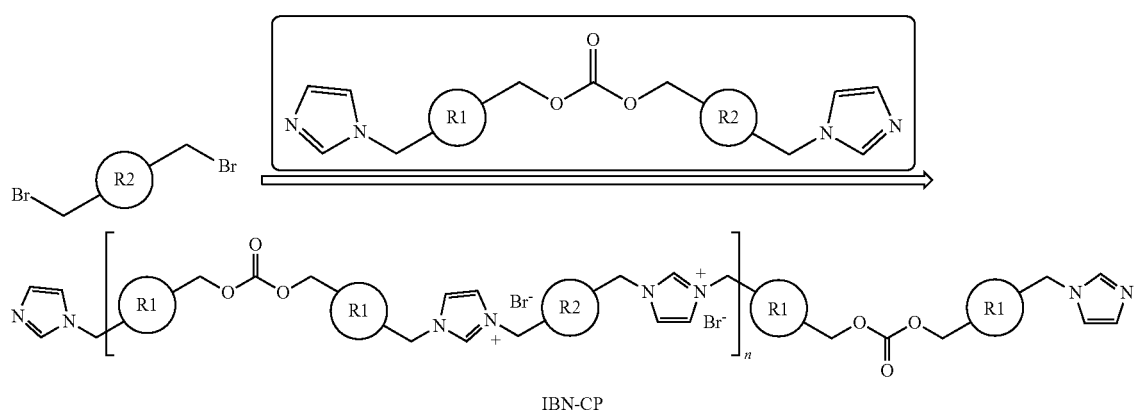
IBN-CP
IBN-CP1 R1 = p-phenylene, R2 = trans-ethylene
IBN-CP2 R1 = R2 = p-phenylene
IBN-CP3 R1 = p-phenylene, R2 = o-phenylene
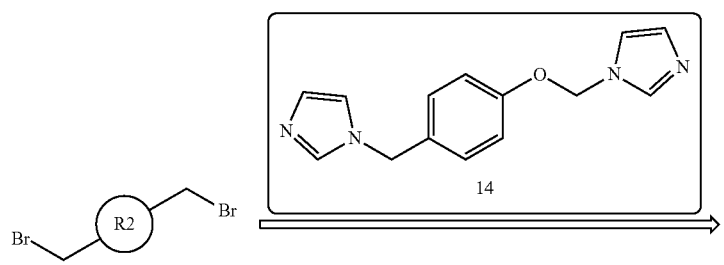
IBN-HP -continued

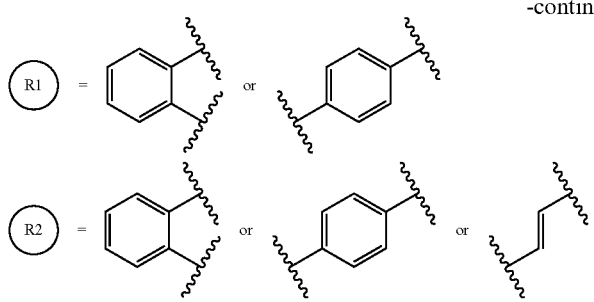

Synthesis of Degradable Linkers

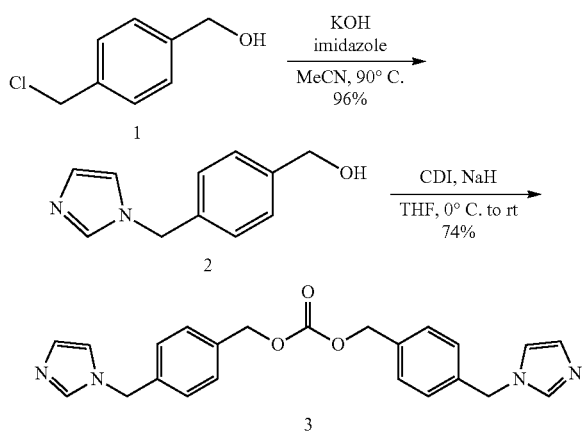

[4-(1H-Imidazol-1-yl)methylphenyl]methanol (2). A two-neck round-bottom flask fitted with a dropping funnel and reflux condenser was filled with imidazole (871 mg, 12.8 mmol) and powdered KOH (1.16 g, 16.6 mmol). Acetonitrile (70 mL) was added to the flask and the mixture was stirred at room temperature over 1 hour. The dropping funnel was then charged with a solution of benzyl chloride 1 (2.00 g, 12.8 mmol) in acetonitrile (57 mL) that was added dropwise to the stirring mixture. Upon complete addition, the reaction mixture was stirred at reflux over 16 hours, then cooled to room temperature and concentrated under reduced pressure. The resultant solids were dissolved in chloroform (20 mL) and washed with water (20 mL). The aqueous layer was then extracted with ethyl acetate (2×20 mL). The combined organic layers were dried over $Na_2SO_4$, filtered and concentrated under reduced pressure to obtain benzyl alcohol 2 as a yellow oil (2.31 g, 12.3 mmol, 96%). $^1$H NMR (400 MHz, $CDCl_3$) δ 7.42 (s, 1H, ImH), 7.33 (d, J=8.0 Hz, 2H, PhH), 7.08 (d, J=8.0 Hz, 2H, PhH), 6.97 (t, J=1.0 Hz, 1H, ImH), 6.85 (d, J=1.0 Hz, 1H, ImH), 5.04 (s, 1H, $NCH_2$), 4.66 (s, 1H, $OCH_2$); $^{13}$C NMR (101 MHz, $CDCl_3$) δ 141.4, 137.4, 135.3, 129.7, 127.5, 119.3, 64.6, 50.6.

Bis[4-(1H-Imidazol-1-yl)methylbenzyl] carbonate (3). To a solution of benzyl alcohol 2 (1.20 g, 6.35 mmol) in anhydrous THF (20 mL) at 0° C. was added 1,1'-carbonyldiimidazole (CDI, 1.03 g, 6.35 mmol) in one portion. The solution was stirred and warmed to room temperature over 2 hour. In the meantime, a second solution of benzyl alcohol 2 (1.20 g, 6.35 mmol) in anhydrous THF (20 mL) was cooled to 0° C. NaH (60% dispersion in mineral oil, 254 mg, 6.35 mmol) was added to the second solution and the mixture was stirred at 0° C. for 30 minutes. The solution of benzyl carbamate was then added slowly to the solution of deprotonated benzyl alcohol at 0° C. and the resulting mixture was warmed to room temperature over 1 hour. The reaction mixture was diluted with ethyl acetate (10 mL) and quenched with saturated aqueous $NH_4Cl$ (50 mL) The aqueous layer was extracted with ethyl acetate (2×30 mL) and the combined organic layers were dried over $Na_2SO_4$, filtered and concentrated under reduced pressure. The resulting crude material was purified by column chromatography (1% MeOH in $CHCl_3$) to obtain carbonate 3 as an off-white solid (1.90 g, 4.72 mmol, 74%). $^1$H NMR (400 MHz, $CDCl_3$) δ 7.54 (s, 2H, ImH), 7.36 (d, J=8.0 Hz, 4H, PhH), 7.14 (d, J=8.0 Hz, 4H, PhH), 7.09 (s, 2H, ImH), 6.89 (s, 2H, ImH), 5.15 (s, 4H, $OCH_2$), 5.12 (s, 4H, $NCH_2$); $^{13}$C NMR (101 MHz, $CDCl_3$) δ 154.9, 137.4, 136.6, 135.2, 129.9, 128.9, 127.5, 119.3, 69.2, 50.4.

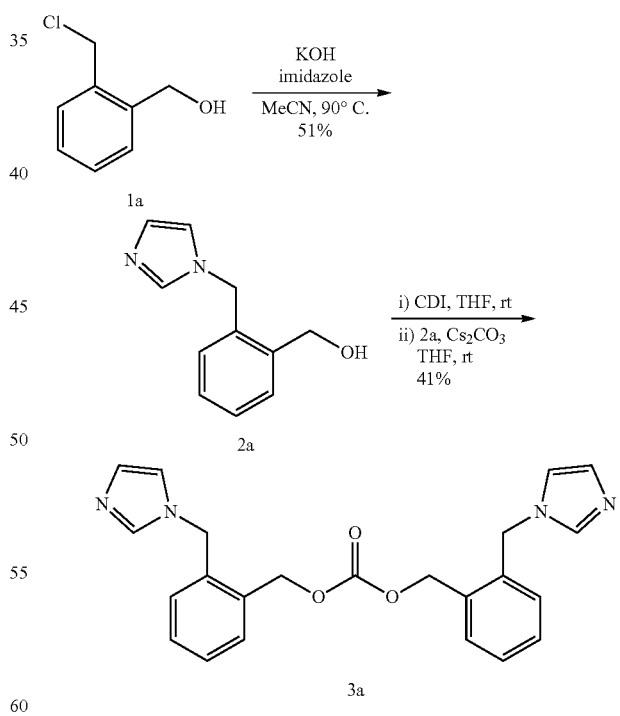

[2-(1H-Imidazol-1-yl)methylphenyl]methanol (2a). A two-neck round-bottom flask fitted with a dropping funnel and reflux condenser was filled with imidazole (722 mg, 10.6 mmol) and powdered KOH (774 mg, 13.8 mmol). Acetonitrile (46 mL) was added to the flask and the mixture was stirred at room temperature over 1 hour. The dropping funnel was then charged with a solution of benzyl chloride 1a (1.75 g, 10.6 mmol) in acetonitrile (23 mL) that was added dropwise to the stirring mixture. Upon complete addition, the reaction mixture was stirred at reflux over 48 hours, then cooled to room temperature and concentrated under reduced pressure. The resultant solids were dissolved in chloroform (50 mL) and washed with water (50 mL). The aqueous layer was then extracted with ethyl acetate (2×50 mL). The combined organic layers were dried over $Na_2SO_4$, filtered and concentrated under reduced pressure. The resulting crude material was purified by column chromatography (5% MeOH in $CH_2C_{12}$) to obtain benzyl alcohol 2a as a colourless oil (1.01 g, 5.37 mmol, 51%). $^1$H NMR (400 MHz, $CDCl_3$) δ 7.40 (d, J=7.5 Hz, 1H, PhH), 7.38 (s, 1H, ImH), 7.35-7.26 (m, 3H, PhH), 7.01 (d, J=7.5 Hz, 1 H, PhH), 6.98 (s, 1 H, ImH), 6.87 (s, 1 H, ImH), 5.25 (s, 1H, $NCH_2$), 4.63 (s, 1 H, $OCH_2$); $^{13}$C NMR (101 MHz, $CDCl_3$) δ 138.8, 137.4, 134.3, 129.1, 128.9, 128.7, 128.6, 128.4, 119.5, 62.7, 48.1

Bis[2-(1H-Imidazol-1-yl)methylbenzyl] carbonate (3a). To a solution of 1,1'-carbonyldiimidazole (CDI, 539 mg, 3.33 mmol) in anhydrous THF (2 mL) was added a solution of benzyl alcohol 2a (250 mg, 1.33 mmol) in anhydrous THF (4 mL). The solution was stirred at room temperature over 3 hours. The reaction mixture was diluted with ethyl acetate (10 mL) and washed with saturated aqueous $NaHCO_3$ (2×10 mL). The organic layer was dried over $Na_2SO_4$, filtered and concentrated under reduced pressure. The residue obtained was dissolved in THF (13 mL). To this solution was added benzyl alcohol 2a (250 mg, 1.33 mmol) and $Cs_2CO_3$ (867 mg, 2.66 mmol). The reaction mixture was stirred at room temperature over 20 hours. The reaction mixture quenched with saturated aqueous $NH_4Cl$ (30 mL), and the aqueous layer was extracted with ethyl acetate (3×20 mL). The combined organic layers were dried over $Na_2SO_4$, filtered and concentrated under reduced pressure. The resulting crude material was purified by column chromatography (5% MeOH in $CH_2C_{12}$) to obtain carbonate 3a as an viscous yellow oil (220 mg, 0.547 mmol, 41%). $^1$H NMR (400 MHz, $CDCl_3$) δ 7.51 (s, 2H, ImH), 7.44-7.41 (m, 2H, PhH), 7.39-7.34 (m, 4H, PhH), 7.07 (s, 2H, ImH), 7.04-7.01 (m, 2H, PhH), 6.87 (s, 2H, ImH), 5.23 (s, 4H, $OCH_2$), 5.14 (s, 4H, $NCH_2$); $^{13}$C NMR (101 MHz, $CDCl_3$) δ 154.5, 137.5, 135.1, 132.5, 130.8, 129.9, 129.8, 128.72, 128. 70, 119.3, 67.3, 48.0.

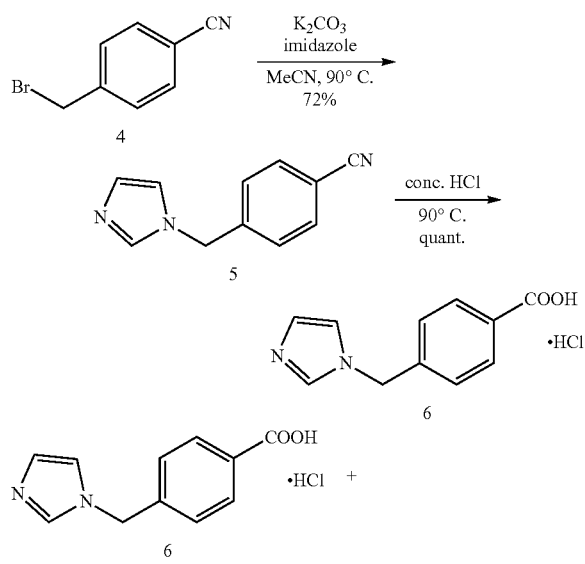

4-[(1H-Imidazol-1-yl)methyl]benzonitrile (5). To a solution of benzyl bromide 4 (3.00 g, 15.3 mmol) in acetonitrile (50 mL) in a two-neck round-bottom flask fitted with a reflux condenser was added imidazole (3.10 g, 45.9 mmol) followed by solid $K_2CO_3$ (10.6 g, 76.5 mmol). The reaction mixture was stirred at reflux over 16 hours, then cooled to room temperature and filtered through cotton wool. The filtrate was concentrated and the resultant solids were re-dissolved in dichloromethane (50 mL). The organic solution was washed with saturated aqueous sodium carbonate solution (2×30 mL), dried over $Na_2SO_4$, filtered and concentrated under reduced pressure to obtain benzonitrile 5 as a yellow powder (2.01 g, 11.0 mmol, 72%). $^1$H NMR (400 MHz, $CDCl_3$) δ 7.66 (d, J=8.5 Hz, 2H, PhH), 7.57 (s, 1 H, ImH), 7.22 (d, J=8.5 Hz, 2H, PhH), 7.14 (s, 1H, ImH), 6.91 (s, 1H, ImH), 5.21 (s, 2H, $NCH_2$); $^{13}$C NMR (101 MHz, $CDCl_3$) δ 141.6, 137.6, 132.9, 130.5, 127.6, 119.3, 118.3, 112.4, 50.2.

4-[(1H-Imidazol-1-yl)methyl]benzoic acid (6). Benzonitrile 5 (100 mg, 0.546 mmol) was dissolved in 37% concentrated hydrochloric acid (1.5 mL) and stirred at reflux for 3 hours. The solution was cooled to room temperature then concentrated under reduced pressure to obtain carboxylic acid 6 as a white solid (130 mg, 0.546 mmol, quant.). $^1$H NMR (400 MHz, $d_4$-MeOD) δ 7.86 (d, J=8.5 Hz, 2H, PhH), 7.78 (s, 1H, ImH), 7.32 (d, J=8.5 Hz, 2H, PhH), 7.14 (s, 1H, ImH), 7.01 (s, 1H, ImH), 5.31 (s, 2H, $NCH_2$); $^{13}$C NMR (101 MHz, $d_4$-MeOD) δ 171.8, 142.3, 138.8, 134.7, 129.5, 129.3, 128.5, 121.0, 51.1.

4-[(1H-Imidazol-1-yl)methyl]benzyl 4-[(1H-imidazol-1-yl)methyl]benzoate (7). To a solution of carboxylic acid 6 (193 mg, 0.808 mmol) and DMAP (85 mg, 0.699 mmol) in anhydrous THF (35 mL) was added a solution of benzyl alcohol 2 (101 mg, 0.538 mmol) and DCC (111 mg, 0.538 mmol) in anhydrous THF (35 mL). The resulting mixture was stirred at room temperature over 12 hours then filtered through cotton wool. The filtrate was concentrated and the resultant solids were dissolved in ethyl acetate (10 mL) and washed with saturated aqueous $NaHCO_3$ (2×10 mL). The organic layer was dried over $Na_2SO_4$, filtered and concentrated under reduced pressure. The resulting crude material was purified by column chromatography (0→5% MeOH in $CHCl_3$) to obtain ester 7 as a white solid (94 mg, 0.252 mmol, 47%). $^1$H NMR (400 MHz, $CDCl_3$) δ 8.04 (d, J=8.0 Hz, 2H, PhH), 7.55 (s, 1 H, ImH), 7.54 (s, 1H, ImH), 7.42 (d, J=8.0 Hz, 2H, PhH), 7.20-7.16 (m, 4H, PhH), 7.10 (s, 1H, ImH), 7.08 (s, 1H, ImH), 6.89 (s, 2H, ImH), 5.34 (s, 2H, $OCH_2$), 5.18 (s, 2H, $NCH_2$), 5.12 (s, 2H, $NCH_2$); $^{13}$C NMR (101 MHz, $CDCl_3$) δ 165.7, 141.5, 137.5, 137.4, 136.3, 136.0, 130.4, 130.0, 129.9, 129.8, 128.8, 127.5, 127.1, 119.3, 66.3, 50.4, 50.3.

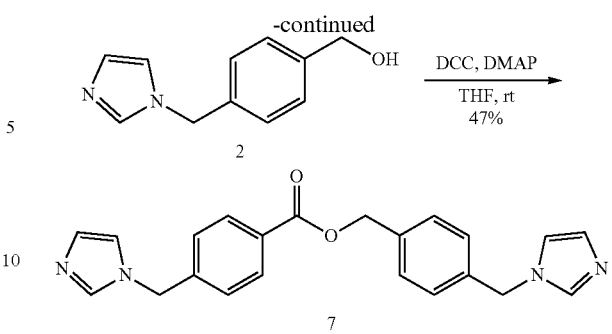

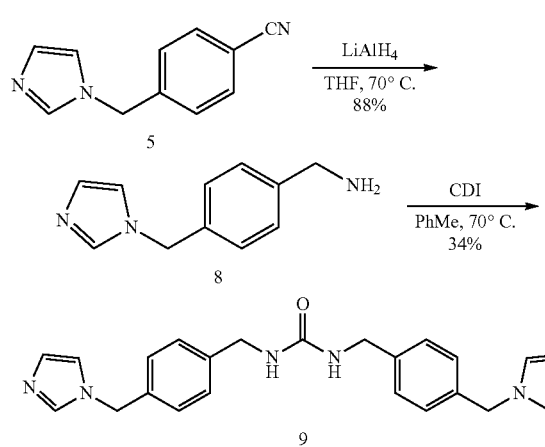

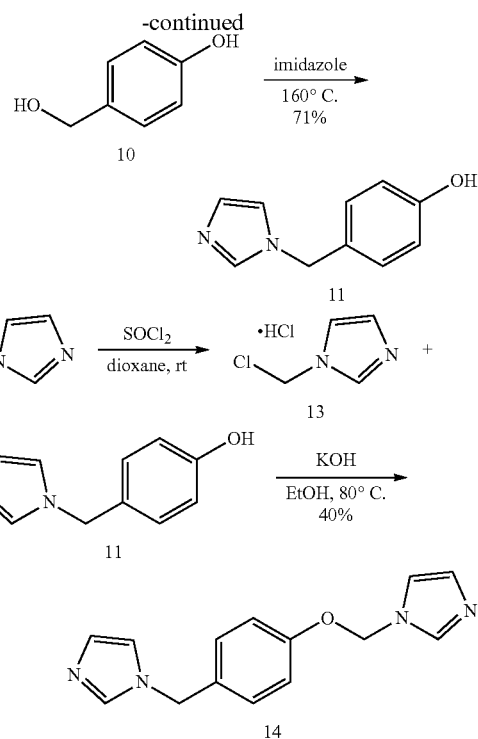

4-(1H-Imidazol-1-yl)methyl phenyl methanamine (8). To a three-neck round-bottom flask fitted with a dropping funnel and reflux condenser was added solid LiAlH$_4$ (1.70 g, 43.9 mmol) followed by anhydrous THF (12 mL). The suspension was heated at a gentle reflux. The dropping funnel was then charged with a solution of benzonitrile 5 (2.01 g, 11.0 mmol) in anhydrous THF (35 mL), which was added dropwise to the refluxing mixture over the course of 1 hour. The resulting thick brown slurry was stirred at reflux over 16 hours, then cooled to 0° C. and quenched carefully with water (10 mL) till it formed a thick white slurry. The pH of the slurry was adjusted to 12 with 3M aqueous NaOH, and the resulting mixture was filtered through Celite® that was rinsed with dichloromethane. The organic layer from the filtrate was collected, and the aqueous layer was extracted with dichloromethane (2×20 mL). The combined organic layers were dried over Na$_2$SO$_4$, filtered and concentrated under reduced pressure to obtain benzylamine 8 as a yellow oil (1.81 g, 9.67 mmol, 88%). $^1$H NMR (400 MHz, CDCl$_3$) δ 7.54 (s, 1H, lmH), 7.31 (d, J=8.0 Hz, 2H, PhH), 7.13 (d, J=8.0 Hz, 2H, PhH), 7.08 (s, 1H, lmH), 6.90 (s, 1H, lmH), 5.11 (s, 2H, NCH$_2$), 3.87 (s, 2H, CH$_2$NH$_2$); $^{13}$C NMR (101 MHz, CDCl$_3$) δ 143.4, 137.4, 134.6, 129.8, 127.7, 127.6, 119.2, 50.6, 46.0.

1,3-Bis[4-(1H-imidazol-1-yl)methylbenzyl]urea (9). A solution of benzyl amine 8 (1.80 g, 9.82 mmol) and 1,1-carbonyldiimidazole (CDI, 1.17 g, 5.93 mmol) in anhydrous toluene (21 mL) was stirred at 70° C. for over 16 hours. The resulting mixture was cooled to room temperature and concentrated. The resultant solids were dissolved in dichloromethane (50 mL) and washed with saturated aqueous Na$_2$CO$_3$ (20 mL). The aqueous layer was extracted with DCM (2 x 10 mL) and the combined organic layers were dried over Na$_2$SO$_4$, filtered and concentrated under reduced pressure. The resulting crude material was purified by column chromatography (6→10% MeOH in dichloromethane) to obtain urea 9 as a white solid (662 mg, 1.65 mmol, 34%). $^1$H NMR (400 MHz, CDCl$_3$) δ 7.42 (s, 2H, lmH), 7.17 (d, J=8.0 Hz, 4H, PhH), 7.00 (d, J=8.0 Hz, 4H, PhH), 6.98 (s, 2H, lmH), 6.84 (s, 2H, lmH), 6.01 (t, J=5.5 Hz, 2H, NH), 5.01 (s, 4H, NCH$_2$), 4.27 (d, J=5.5 Hz, 4H, CH$_2$NH); $^{13}$C NMR (101 MHz, CDCl$_3$) δ 158.7, 140.1, 137.2, 134.8, 129.4, 127.8, 127.5, 119.4, 50.5, 43.6.

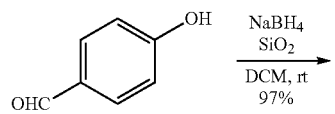

4-(1H-Imidazol-1-yl)methylphenol (11). Benzyl alcohol 10 [J. McNulty, D. McLeod; Tetrahedron Lett. 2013, 54, 6303-6306.] (1.92 g, 15.5 mmol) and imidazole (3.17 g, 46.5 mmol) were combined in vial vented by a needle and heated at 160° C. for over 30 minutes. The hot mixture was poured into boiling water (100 mL), and the hot suspension was filtered through a Büchner funnel. The residue was rinsed with hot water (2×10 mL) and dried in vacuo (50° C., 10 mbar) to obtain phenol 11 as a white powder (1.92 g, 11.0 mmol, 71%). $^1$H NMR (400 MHz, d$_6$-DMSO) δ 9.50 (br s, 1H, OH), 7.69 (s, 1H, lmH), 7.13 (t, J=1.0 Hz, 1H, lmH), 7.10 (d, J=8.5 Hz, 2H, PhH), 6.87 (t, J=1.0 Hz, 1h, lmH), 6.72 (d, J=8.5 Hz, 2H, PhH), 5.03 (s, 2H, NCH$_2$); $^{13}$C NMR (101 MHz, d$_6$-DMSO) δ 157.0, 137.1, 129.1, 128.6, 128.0, 119.3, 115.3, 49.1.

The spectroscopic data was found to be in agreement with that reported by McNulty and co-workers [J. McNulty, D. McLeod; Tetrahedron Lett. 2013, 54, 6303-6306.].

1-(Chloromethyl)-1H-imidazole (13). To a solution of 1H-imidazole-1-methanol 12 [A. M. Deberardinis, M. Turlington, J. Ko, L. Sole, L Pu; J. Org. Chem. 2010, 75, 2836-2850.] (80% w/w, 1.00 g, 8.15 mmol) in anhydrous dioxane (16 mL) was added SOCl2 (1.8 mL, 24.5 mmol). The reaction mixture was stirred at room temperature over 2 hours then concentrated under reduced pressure to obtain chloride 13 as an off-white syrup (1.79 g). Analysis of the crude material by $^1$H NMR spectroscopy (d$_6$-DMSO) revealed chloride 13 present as its HCl salt along with imidazole hydrochloride in a 3:2 ratio (69% w/w).

1-[4-(1H-Imidazol-1-yl)methoxybenzyl]-1H-imidazole (14). To a solution of chloride 13 (69% w/w, 1.35 g, 6.09 mmol) in EtOH (12 mL) were added phenol 11 (1.06 g, 6.09 mmol) and KOH pellets (1.03 g, 18.3 mmol). The solution was stirred under reflux for 16 hours then cooled to room temperature and filtered through cotton wool. The filtrate was concentrated and the resultant solids were re-dissolved in dichloromethane (10 mL). The organic solution was washed with water (10 mL) followed by 1 M aqueous NaOH (3×10 mL), dried over Na$_2$SO$_4$, filtered and concentrated under reduced pressure to obtain hemiaminal 14 as a yellow oil (616 mg, 2.42 mmol, 40%). $^1$H NMR (400 MHz, d$_6$-DMSO) δ 7.87 (s, 1H, ImH), 7.73 (s, 1 H, ImH), 7.34 (t, J=1.5 Hz, 1H, ImH), 7.23 (d, J=8.5 Hz, 2H, PhH), 7.16 (t, J=1.5 Hz, 1H, ImH), 7.04 (d, J=8.5 Hz, 2H, PhH), 6.92 (t, J=1.0 Hz, 1H, ImH), 6.88 (t, J=1.0 Hz, 1H, ImH), 5.98 (s, 2H, OCH$_2$), 5.11 (s, 2H, NCH$_2$); $^{13}$C NMR (101 MHz, d$_6$-DMSO) δ 155.4, 138.3, 137.3, 131.6, 129.2, 129.0, 128.7, 119.9, 119.5, 116.1, 72.9, 48.9.

Example 6

General Procedure For The Synthesis of Imidazolium Oligomers

Linker (1.0 eq) and bisimidazolium salt (2.4 eq) were dissolved in anhydrous DMF (0.02 M) and stirred at room temperature over 24 to 48 hours. The reaction mixture was concentrated in vacuo to approx. 5-10 mL, and the product was precipitated with acetone. The solids were spun down in a Falcon® tube in a centrifuge (5000 rpm), and the supernatant was decanted. The solids were washed twice more by first being dissolved in the minimum amount of methanol, and then precipitated with acetone (total volume of 40-50 mL). The resulting solids were dried in a vacuum oven (50° C., 10 mbar) over 16 hours to obtain the imidazolium oligomers as white powders.

Where DMF was detected in NMR spectroscopic analysis of the compounds, it could be azeotropically removed with toluene. This was achieved by first dissolving the powder in the minimum amount of methanol, adding 3-4 times the volume of toluene and removing the solvents in vacuo. Repeating this step twice was usually sufficient to remove traces of DMF from the samples for biological testing.

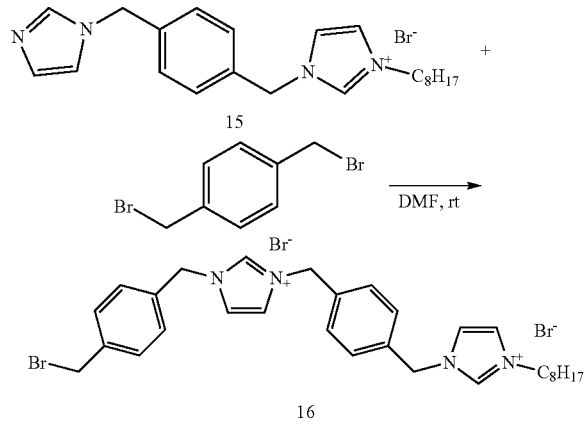

A solution of 15 [S. N. Riduan, Y. Yuan, F. Zhou, J. Leong, H. Su, Y. Zhang; Small, 2016, 12, 1928-1934] (2.63 g, 6.23 mmol) in DMF (62 mL) was added dropwise to a solution of 1,4-dibromo-p-xylene(16.4 g, 62.3 mmol) and the resulting mixture stirred at room temperature over 48 hours. The reaction mixture was concentrated in vacuo, and the product was precipitated with ether. The solids were spun down in a Falcon® tube in a centrifuge (5000 rpm), and the supernatant was decanted. The solids were washed with ether followed by acetone. The resulting solids were dried in a vacuum oven (50° C., 10 mbar) over 16 hours to obtain bisimidazolium salt 16 as white solids (2.88 g, 4.44 mmol, 71%). $^1$H NMR (400 MHz, d$_6$-DMSO) δ 9.49 (s, 1 H, ImH), 9.39 (s, 1 H, ImH), 7.86-7.82 (m, 4H, ImH),7.51-7.40 (m, 8H, PhH), 5.45 (s, 6H, PhH), 4.71 (s, 2H, CH$_2$Br), 4.17 (t, J=7.4 Hz, 2H, CH$_2$N), 1.80-1.76 (m, 2H, NCH$_2$CH$_2$), 1.31-1.15 (m, 10H, C$_5$H$_{10}$), 0.85 (t, J=6.5 Hz, 6H, 2×CH$_3$); $^{13}$C NMR (101 MHz, d$_6$-DMSO) δ 138.7, 136.4, 136.2, 135.5, 1353, 134.9, 129.9, 129.1, 128.9, 128.7, 123.0, 122.9, 122.6, 51.6, 51.5, 5 1.4, 49.0, 31.2, 29.3, 28.5, 28.3, 25.5, 22.1, 14.0.

Unreacted 1,4-dibromo-p-xylene(ca 8 equivalents) was recovered by concentrating the combined ether washings.

IBN-Carbonate-C8 (IBN-CC8) was prepared by the general procedure from carbonate linker 3 and isolated as a white powder (438 mg, 0.244 mmol, 47%). $^1$H NMR (400 MHz, d$_6$-DMSO) δ 9.56-9.54 (m, 4H, ImH), 9.42 (s, 2H, ImH), 7.86-7.84 (m, 12H, ImH), 7.51-7.43 (m, 24H, PhH), 5.47 (s, 20H, 10×NCH$_2$), 5.16 (s, 4H, 2×OCH$_2$), 4.17 (t, J=7.0 Hz, 4H, 2×NCH$_2$CH$_2$), 1.80-1.77 (m, 4H, 2×NCH$_2$CH$_2$), 1.24-1.23 (m, 20H, 2×C$_5$H$_{10}$), 0.85 (t, J=6.5 Hz, 6H, 2×CH$_3$); $^{13}$C NMR (101 MHz, d$_6$-DMSO) δ 154.4, 136.4, 136.2, 136.1, 135.6, 135.4, 135.4, 135.3, 135.0, 129.1, 129.0, 128.8, 128.7, 123.0, 122.9, 122.6, 68.7, 51.7, 51.6, 51.5, 49.0, 31.2, 29.3, 28.5, 28.4, 25.6, 22.1, 14.0; HRMS (ESI$^+$) calc. for C$_{83}$H$_{100}$Br$_4$N$_{12}$O$_3$ [M-2Br]$^{2+}$ 816.2361; found 816.1995.

IBN-Ester-C8 (IBN-EC8) was prepared by the general procedure from ester linker 7 and isolated as a white powder (102 mg, 0.060 mmol, 34%). $^1$H NMR (400 MHz, d$_6$-DMSO) δ 9.56-9.42 (m, 6H, ImH), 8.05-8.02 (m, 2H, PhH), 7.90-7.80 (m, 12H, ImH), 7.61-7.37 (m, 20H, PhH), 5.58-5.36 (m, 22H, OCH$_2$+10×NCH$_2$), 4.18 (t, J=7.0 Hz, 4H, 2×NCH$_2$CH$_2$), 1.82-1.75 (m, 4H, 2×NCH$_2$CH$_2$), 1.31-1.17 (m, 20H, 2×C$_5$H$_{10}$), 0.85 (t, J=6.5 Hz, 6H, 2×CH$_3$); $^{13}$C NMR (101 MHz, d$_6$-DMSO) δ 165.2, 140.1, 136.7, 136.4, 136.2, 135.5, 135.4, 135.3, 129.9, 129.1, 129.0, 128.7, 128.5, 122.9, 122.6, 65.9, 51.6, 51.4, 49.0, 31.2, 29.3, 28.5, 28.3, 25.5, 22.1, 14.0; HRMS (ESI$^+$) calc. for C$_{82}$H$_{98}$Br$_4$N$_{12}$O$_2$ [M-2Br]$^{2+}$ 801.2309; found 801.1903.

IBN-Urea-C8 (IBN-UC8) was prepared by the general procedure from urea linker 9 and isolated as white powder (745 mg, 0.416 mmol, 75%). $^1$H NMR (400 MHz, d$_6$-DMSO) δ 9.57-9.38 (m, 6H, ImH), 7.86-7.82 (m, 12H, ImH), 7.51-7.21 (m, 24H, PhH), 6.65-6.57 (m, 2H, 2×NH), 5.49-5.26 (m, 20H, 10×NCH$_2$), 4.23-4.16 (m, 8H, 2×NHCH$_2$+2×NCH$_2$CH$_2$), 1.82-1.76 (m, 4H, 2×NCH$_2$CH$_2$), 1.31-1.78 (m, 20H, 2×C$_5$H$_{10}$), 0.85 (t, J=6.5 Hz, 6H, 2×CH$_3$); $^{13}$C NMR (101 MHz, d$_6$-DMSO) δ 158.1, 141.8, 136.4, 136.3, 135.5, 135.3, 133.0, 129.1, 129.0, 128.5, 128.5, 127.6, 127.6, 127.5, 127.4, 122.9, 122.9, 122.6, 51.9, 51.6, 51.4, 49.0, 42.3, 31.2, 29.3, 28.5, 28.3, 25.5, 22.1, 14.0; HRMS (ESI$^+$) calc. for C$_{83}$H$_{102}$Br$_4$N$_{14}$O [M-2Br]$^{2+}$ 815.2521; found 815.2153.

IBN-Hemiaminal-C8 (IBN-HC8) was prepared by the general procedure from hemiaminal linker 14 and isolated as a white powder (625 mg, 0.427 mmol, 50%). $^1$H NMR (400 MHz, d$_6$-DMSO) δ 9.74-9.35 (m, 6H, ImH), 8.00-7.77 (m, 12H, ImH), 7.52-7.45 (m, 18H, PhH), 7.19-7.12 (m, 2H, PhH), 6.26 (s, 2H, OCH$_2$N), 5.51-5.36 (m, 18H, NCH$_2$), 4.16 (t, J=7.0 Hz, 4H, 2×NCH$_2$CH$_2$), 1.81-1.74 (m, 4H, 2×NCH$_2$CH$_2$), 1.31-1.16 (m, 20H, 2×C$_5$H$_{10}$), 0.84 (t, J=6.5 Hz, 6H, 2×CH$_3$); $^{13}$C NMR (101 MHz, d$_6$-DMSO) δ 155.6, 136.5, 136.3, 135.6, 135.5, 135.5, 135.4, 135.4, 130.7, 130.4, 129.2, 129.2, 129.1, 123.0, 122.6, 116.5, 116.4, 75.2, 51.8, 51.7, 51.5, 51.4, 49.1, 31.2, 29.4, 28.6, 28.4, 25.6, 22.2, 14.1.

Example 7

Synthesis of Imidazolium Polymers

General Procedure For The Synthesis of Imidazolium Polymers

Linker (1.0 eq) and butenyl or xylyl dibromide (1.0 eq) were dissolved in solvent (0.2 M) in a 20-mL vial sealed with a PTFE crimp-on cap. The solution was stirred for 30 minutes to 48 hours at room temperature or with heating in a pre-heated DrySyn® heating block. The reaction mixture was transferred to a 15-mL Falcon® tube, dissolved in the minimum volume of methanol then precipitated with ether to form a milky white suspension. The solids were spun down in a centrifuge (7000 rpm, 3 minutes), and the supernatant decanted. The solids were washed once more and the resulting solids were dried in a vacuum oven (50° C., 10 mbar) over 16 hours to obtain the imidazolium polymers as white solids. The n integer value which is the average number is provided in each of the polymers below.

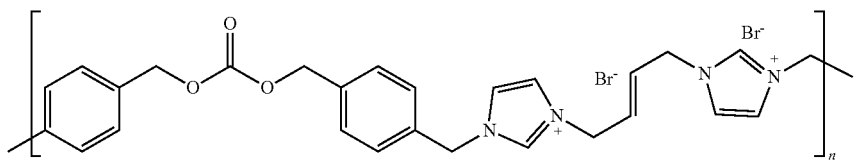

IBN-Carbonate-Polymerl (IBN-CP1) was prepared by the general procedure from carbonate linker 3 (200 mg, 0.50 mmol) and trans-1,4-dibromobutene (106 mg, 0.50 mmol) in DMF (2.5 mL) at room temperature over 48 hours and isolated as a white crushable foam (144 mg, 47%). $^1$H NMR (400 MHz, $d_6$-DMSO) δ 9.48 (br s, 2H, lmH), 7.88-7.82 (m, 4H, lmH), 7.50-7.43 (m, 8H, 2×PhH), 6.06 (br s, 2H, 2×CH), 5.49 (br s, 4H, 2×NCH$_2$), 5.16 (br s, 4H, 2×OCH$_2$), 4.91 (br s, 4H, 2×CHCH$_2$); $^{13}$C NMR (101 MHz, $d_6$-DMSO) δ 154.4, 136.4, 136.0, 129.3, 128.8, 128.7, 123.0, 122.7, 68.7, 51.6, 49.8. n=11.

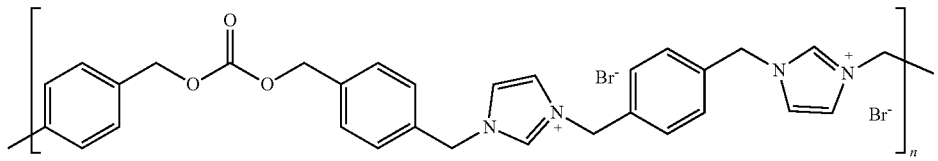

IBN-Carbonate-Polymer 2 (IBN-CP2) was prepared by the general procedure from carbonate linker 3 (100 mg, 0.25 mmol) and α,α'-dibromo-p-xylene(66 mg, 0.50 mmol) in THF (1.2 mL) at 65° C. for over 1 hour and isolated as white solids (93 mg, 56%). $^1$H NMR (400 MHz, $d_6$-DMSO) δ 9.55 (br s, 2H, lmH), 7.88-7.83 (m, 4H, lmH), 7.54-7.36 (m, 12H, 3×p-PhH), 5.51-5.42 (m, 8H, 4×NCH$_2$), 5.20-5.13 (m, 4H, 2×OCH$_2$); $^{13}$C NMR (101 MHz, $d_6$-DMSO) δ 154.8, 136.9, 136.5, 135.8, 135.4, 129.5, 129.2, 129.1, 123.4, 123.3, 69.07, 52.1, 52.0. n=6.

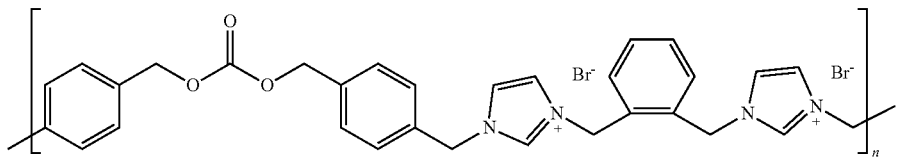

IBN-Carbonate-Polymer 3 (IBN-CP3) was prepared by the general procedure from carbonate linker 3 (100 mg, 0.25 mmol) and α,α'-dibromo-o-xylene(66 mg, 0.50 mmol) in THF (1.2 mL) at 65° C. for over 1 hour and isolated as white solids (131 mg, 79%). $^1$H NMR (400 MHz, d$_6$-DMSO) δ 9.50-9.38 (m, 2H, lmH), 7.87-7.78 (m, 4H, lmH), 7.52-7.42 (m, 8H, 2×p-PhH), 7.38-7.26 (m, 4H, o-PhH), 5.68-5.61 (m, 4H, 2×NCH$_2$), 5.49-5.44 (m, 4H, 2×NCH$_2$), 5.21-5.13 (m, 4H, 2×OCH$_2$); $^{13}$C NMR (101 MHz, d$_6$-DMSO) δ 154.4, 136.7, 136.1, 135.0, 133.0, 129.8, 128.8, 128.6, 127.7, 123.2, 122.9, 68.7, 51.7, 49.2. n=5.

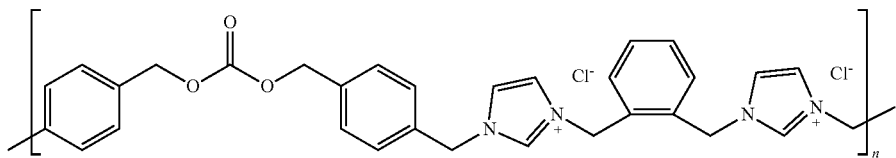

IBN-Carbonate-Polymer 3 CI (IBN-CP3-CI) was prepared by the general procedure from carbonate linker 3 (100 mg, 0.25 mmol) and α,α'-dichloro-o-xylene(44 mg, 0.25 mmol) in MeCN (1.2 mL) at 70° C. for over 12 hours and isolated as a pale yellow foam (146 mg, quant.). $^1$H NMR (400 MHz, d$_6$-DMSO) δ 9.82-9.46 (m, 2H, lmH), 7.94-7.69 (m, 4H, lmH), 7.55-7.27 (m, 12H, 2×p-PhH +o-PhH), 5.81-5.64 (m, 4H, 2×NCH$_2$), 5.57-5.42 (m, 4H, 2×NCH$_2$), 5.23-5.14 (m, 3.2H, 2×OCH$_2$), 4.51 (s, 0.8H, HOCH$_2$). n=5.

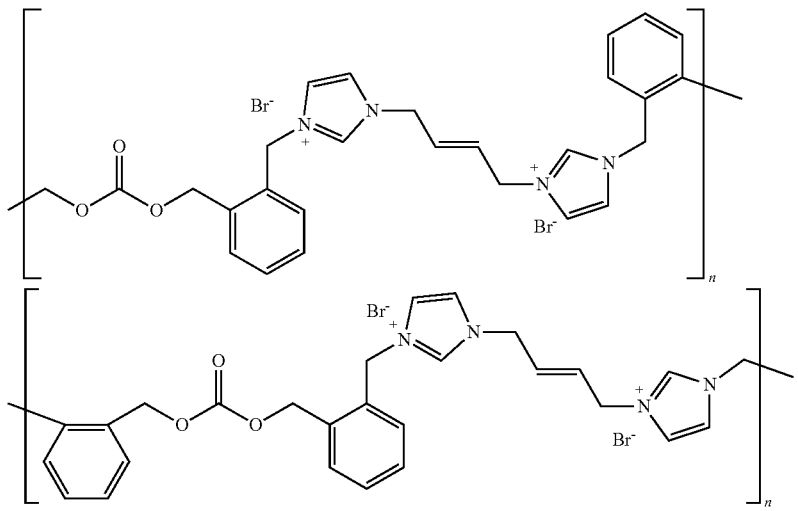

IBN-Carbonate-Polymer 4 (IBN-CP4) was prepared by the general procedure from carbonate linker 3a (90 mg, 0.22 mmol) and trans-1,4-dibromobutene (48 mg, 0.22 mmol) in THF (1.1 mL) at 65° C. for over 1 hour and isolated as a white crushable foam (105 mg, 76%). $^1$H NMR (400 MHz, d$_6$-DMSO) δ 9.43-9.27 (m, 2H, lmH), 7.86-7.76 (m, 4H, lmH), 7.52-7.41 (m, 6H, PhH), 7.29-7.23 (m, 2H, PhH), 6.04-6.03 (m, 2H, 2×CH), 5.63-5.54 (m, 4H, 2×NCH$_2$), 5.35-5.32 (m, 4H, 2×OCH$_2$), 4.88-4.80 (br s, 4H, 2×CHCH$_2$); $^{13}$C NMR (101 MHz, d$_6$-DMSO) δ 153.9, 136.8, 133.6, 130.6, 130.3, 130.0, 129.6, 129.3, 129.1, 129.0, 128.1, 122.9, 67.0, 49.7, 49.0. n=5.

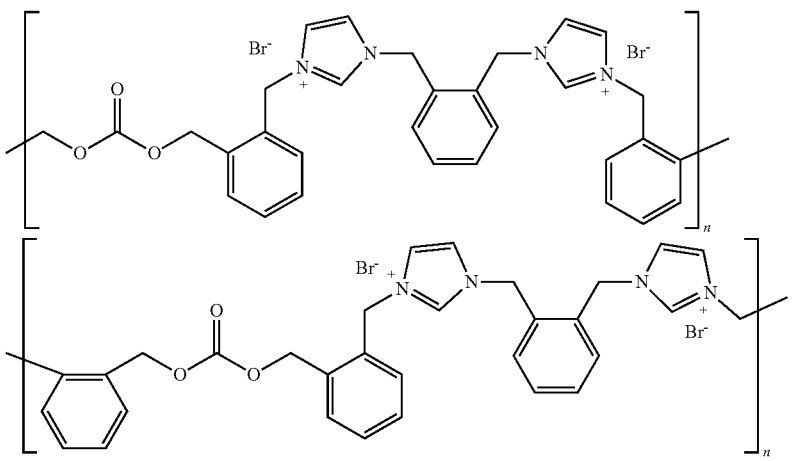

IBN-Carbonate-Polymer 5 (IBN-CP5) was prepared by the general procedure from carbonate linker 3a (90 mg, 0.22 mmol) and α,α'-dibromo-o-xylene(59 mg, 0.22 mmol) in THF (1.1 mL) at 65° C. for over 1 hour and isolated as white solids (110 mg, 74%). $^1$H NMR (400 MHz, d$_6$-DMSO) δ 9.49-9.33 (m, 2H, lmH), 7.87-7.81 (m, 4H, lmH), 7.54-7.41 (m, 8H, PhH), 7.28-7.22 (m, 4H, PhH), 5.69-5.57 (m, 8H, 4×NCH$_2$), 5.36-5.27 (m, 4H, 2×OCH$_2$); $^{13}$C NMR (101 MHz, d$_6$-DMSO) δ 154.0, 137.2, 133.5, 133.0, 130.6, 130.3, 130.0, 129.6, 129.4, 129.1, 128.8, 123.3, 123.1, 67.0, 49.3, 49.2. n=5.

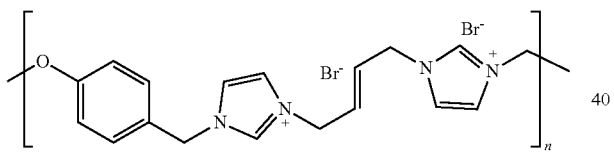

IBN-Hemiaminal-Polymer (IBN-HP) was prepared by the general procedure from hemiaminal linker 14 (220 mg, 0.87 mmol) and trans-1,4-dibromobutene (185 mg, 0.87 mmol) in DMF (4 mL) at room temperature over 48 hours and isolated as a white crushable foam (201 mg, 50%). $^1$H NMR (400 MHz, d$_6$-DMSO) δ 9.70 (br s, 1 H, lmH), 9.52 (br s, 1H, lmH), 8.07 (br s, 1H, lmH), 7.90-7.82 (m, 3H, lmH), 7.54-7.52 (m, 2H, PhH), 7.22-7.20 (m, 2H, PhH), 6.31 (s, 2H, OCH2), 6.07 (br s, 2H, 2×CH), 5.55 (br s, 2H, NCH$_2$), 4.98-4.93 (m, 4H, 2×CHCH$_2$); $^{13}$C NMR (101 MHz, d$_6$-DMSO) δ 155.5, 137.3, 136.2, 130.6, 129.5, 129.4, 129.3, 123.1, 122.9, 122.6, 122.5, 116.3, 74.9, 51.2, 49.9, 49.7. n=6.

Example 8

Calculating Polymer Length by H$^1$ NMR Spectroscopy

Compounds IBN-CP1, IBN-CP2 and IBN-CP3 were found to have imidazole terminal groups based on the analysis of the $^1$H NMR spectrum of purified polymers. The average polymer length, in terms of the number of imidazole and imidazolium units per chain, was calculated based on the ratio of imidazolium (δ 9.3-9.6 ppm) to imidazole (δ 6.9 or 7.2 ppm) integral values (see FIG. 21 and below for the mathematical formula). As illustrated above, IBN-CP3 is a sample prepared in THF at 65° C. (Table 5, Entry 3) for the analysis of the polymer length, where this polymer length is an average polymer chain length.

Average polymer chain length =

$$2\frac{\int imidazolium}{\int imidazole} + 2 = 2\frac{2.00}{0.45} + 2 = 11 \text{ imidazole and imidazolium units}$$

Measuring Oligomer and Polymer Degradation by $^1$H NMR Spectroscopy

Sorenson's phosphate buffer (pH, 6.0, 7.0, 8.0), tris buffer (pH 6.0, 7.0, 8.0) and sodium citrate-citric acid buffer (pH 3.0, 4.0, 5.0) were prepared in deionized water at concentrations of 100 mM, as well as 10 mM for tris buffer solution. Stock solutions of the buffers were divided into 1 mL portions which were freeze-dried and dissolved in 1 mL of D$_2$O. A 4 mg sample of imidazolium oligomer or polymer was dissolved in deuterated buffer solution with care taken to ensure complete solution of the compounds. The solution was stored at 25° C. in NMR tubes and $^1$H NMR spectra were obtained at specific time points. It was found that 128 scans were sufficient to obtain good signal-to-noise ratio.

Degradation of the carbonate and ester-linked compounds was observed by disappearance of the signal of the methylene protons adjacent to the carbonate or ester functional group, and/or appearance of the signal of the methylene protons adjacent to the hydroxyl group in the degradation product.

INDUSTRIAL APPLICABILITY

The oligomers or the polymers as defined above may be as antimicrobial composition. The oligomers or the polymers as defined above may find a multiple number of applications in which their ability to inhibit a microbial activity. The oligomers or the polymers may also be used in treating a microbial infection or disease. The oligomers or the polymers as defined above may find a multiple number of applications in which their ability to inhibit a microbial activity or treating a microbial infection or disease comprising administering the antimicrobial composition as defined above to a subject or applying the antimicrobial composition as defined above on a surface. The use of the oligomers or the polymers as defined above may be in the manufacture of a medicament for treating a microbial infection or disease. The microbial infection or disease is caused by a microbe that is selected from the group consisting of *Staphylococcus aureus, Escherichia coli, Pseudomonas aeruginosa, Bacillus subtilius, Klebsiella pneumonia, Cryptococcus neoformans* and *Candida albicans*. The microbe may be contacted with the antimicrobial composition at a defined concentration and the microbial activity may be reduced to 1% or less. The oligomer of formula (I) may also be used as an antimicrobial gel.

The new imidazolium compounds as defined above may retain the excellent antimicrobial activity of the previous generation of materials against a broad range of microbes, and may possess essential degradation and non-resistance properties. Imidazolium polymers and oligomers with a carbonate linkage may have also demonstrated the best performance. The new imidazolium compounds as defined above may have tuneable degradation profiles under different conditions which would have wide ranging applications in agricultural and environmental disinfection.

The antimicrobial composition may be added to household products, sanitizers or disinfectants that can be used in a variety of settings, from imparting an antimicrobial property to clothings, household products, floors, surfaces of objects, etc, or be used in general medical applications to sterilize or sanitise surfaces (such as hospital beds, operating theatres, etc).

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. An oligomer of formula (I)

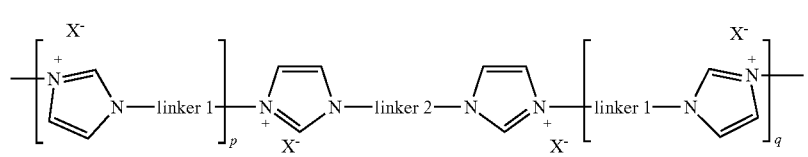

Formula (I)

wherein linker 1 is an alkyl-aryl-alkyl group or ($C_2$-$C_8$) alkene;

p and q are independently an integer from 2 to 6, that is, 2, 3, 4, 5, or 6;

linker 2 is

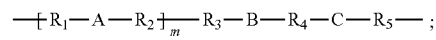

m is 0 or 1;

A is independently aryl or heteroaryl;

B is independently O, N or S;

C is independently aryl or heteroaryl;

$R_1$ is a bond, alkyl, or absent;

$R_2$ is a bond, alkoxy or amine;

$R_3$ is carbonyl, a bond or alkyl;

$R_4$ is a bond or alkyl; $R_5$ is alkyl; and

X is a halide selected from fluoride, chloride and bromide.

2. The oligomer of claim 1, wherein linker 2 is selected from the group consisting of

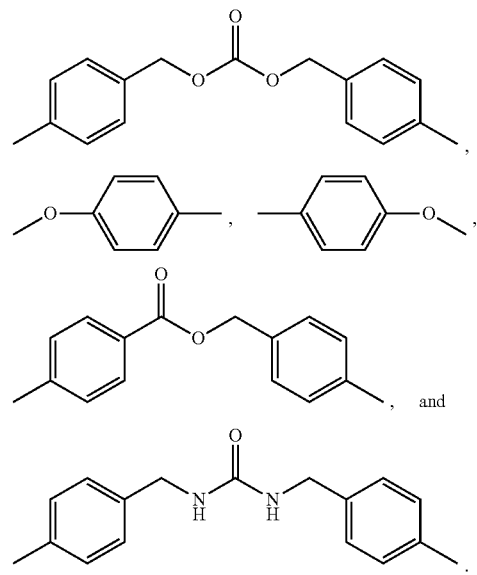

3. The oligomer of claim 1, wherein when linker 1 is alkyl-aryl-alkyl, said alkyl-aryl-alkyl is a $C_{1-6}$alkyl-phenyl-$C_{1-6}$alkyl.

4. The oligomer of claim 1, wherein the oligomer has a terminal group, or the oligomer is selected from

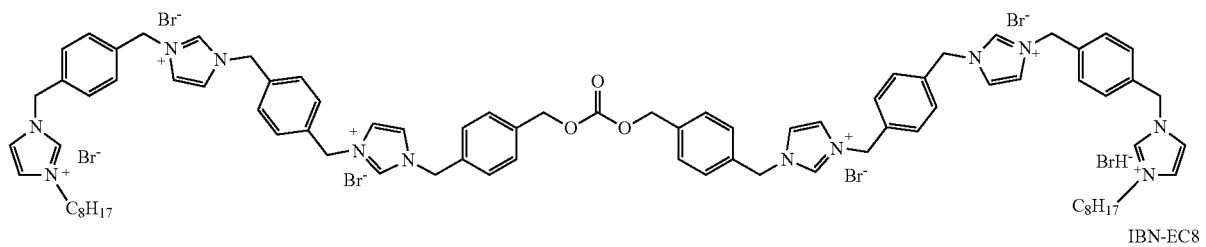
IBN-CC8

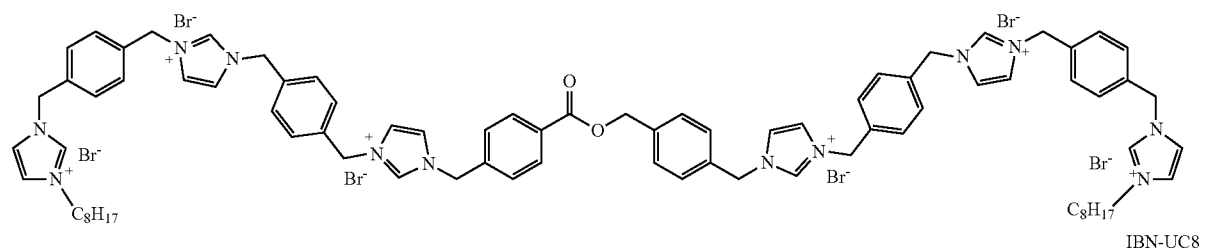
IBN-EC8

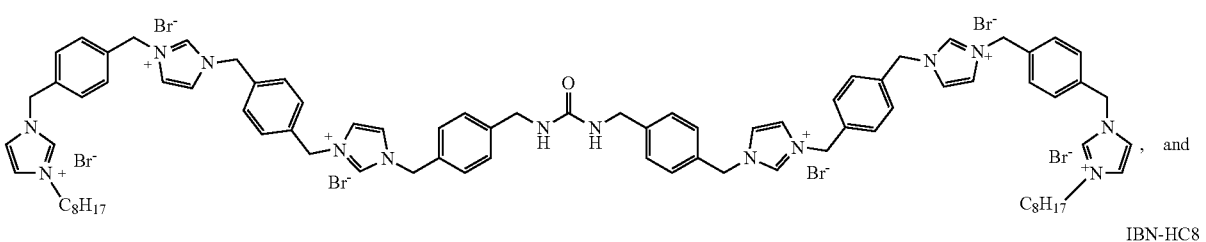
IBN-UC8
, and

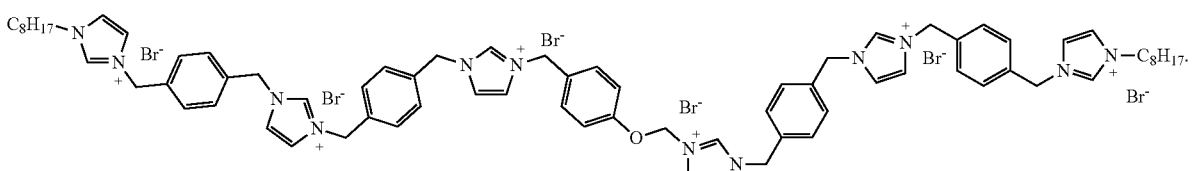
IBN-HC8

⊘ indicates text missing or illegible when filed

5. An oligomer or a polymer of formula (II)

Formula (II)

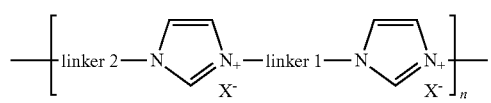

wherein linker 1 is an alkyl-aryl-alkyl group or ($C_2$-$C_8$) alkene;
n is an integer from 3 to 30, that is, 3, 4, 5, 6, 7, 8, 9, 10, 11, 12, 13, 14, 15, 16, 17, 18, 19, 20, 21, 22, 23, 24, 25, 26, 27, 28, 29 or 30;
linker 2 is

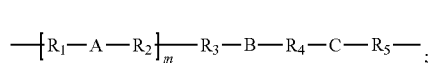

m is 0 or 1;
A is independently aryl or heteroaryl;
B is independently O, N or S;
C is independently aryl or heteroaryl;

$R_1$ is a bond or alkyl;
$R_2$ is a bond, alkoxy or amine;
$R_3$ is carbonyl, a bond or alkyl;
$R_4$ is a bond or alkyl;
$R_5$ is alkyl; and
X is a halide selected from fluoride, chloride and bromide.

6. The oligomer or the polymer of claim 5, wherein linker 2 is selected from the group consisting of

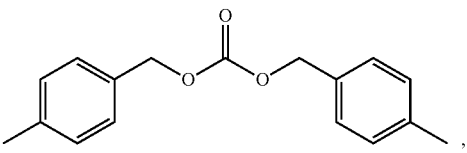

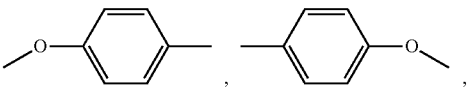

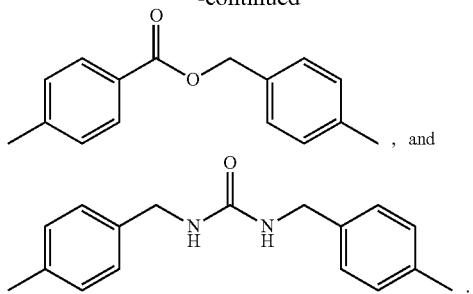

7. The oligomer or the polymer of claim 5, wherein when linker 1 is alkyl-aryl-alkyl, said alkyl-aryl-alkyl is a $C_{1-6}$alkyl-phenyl-$C_{1-6}$alkyl.

8. The oligomer or the polymer of claim 5, wherein the polymer has a terminal group selected from the group consisting of linker 2, an imidazolium ring and a combination thereof.

9. An antimicrobial composition comprising the oligomer as defined in claim 1.

10. The antimicrobial composition of claim 9, wherein said antimicrobial composition inhibits the activity or treats the infection or disease caused by a microbe that is selected from the group consisting of *Staphylococcus aureus, Escherichia coli, Pseudomonas aeruginosa, Bacillus subtilius, Klebsiella pneumonia, Cryptococcus neoformans* and *Candida albicans*, or wherein when said microbe is contacted with said antimicrobial composition at a defined concentration, microbial activity of said microbe is reduced to 1%, or to 0.5%, or to 0.1%, or wherein said defined concentration of said antimicrobial composition is in the range of about 1 µg/ml to about 100 µg/ml, or wherein the reduction of the microbial activity is achieved within a duration of about 0.5 minutes to about 120 minutes, or wherein the microbe is not resistant to said antimicrobial composition.

11. A method of treating a microbial infection or disease comprising administering the oligomer of claim 1 to a subject.

12. The method of claim 11, wherein said oligomer inhibits the activity or treats the infection or disease caused by a microbe that is selected from the group consisting of *Staphylococcus aureus, Escherichia coli, Pseudomonas aeruginosa, Bacillus subtilius, Klebsiella pneumonia, Cryptococcus neoformans*, and *Candida albicans*.

13. The method of claim 12, wherein when said microbe is contacted with said oligomer at a defined concentration, microbial activity of said microbe is reduced to 1% or wherein said defined concentration of said oligomer is in the range of about 1 µg/ml to about 100 µg/ml.

14. A method of preparing an oligomer of formula (I)

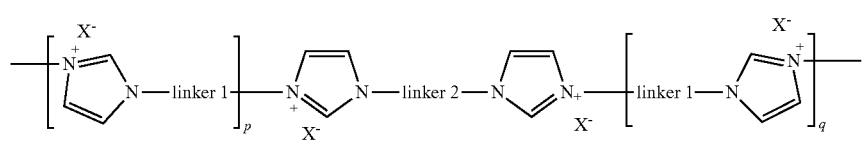

Formula (I)

wherein linker 1 is an alkyl-aryl-alkyl group or ($C_2$-$C_8$) alkene;

p and q are independently an integer from 2 to 6, that is 2, 3, 4, 5 or 6;

linker 2 is

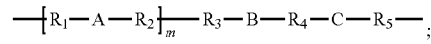

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, a bond or alkyl;
$R_4$ is a bond or alkyl;
$R_5$ is alkyl;
X is halide selected from fluoride, chloride and bromide,
said method comprising the steps of:

a) providing a di-imidazole unit bearing linker 2 of Formula (III)

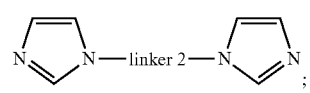

Formula (III)

b) mixing the di-imidazole of Formula (III) with an imidazolium salt that is dissolved in a suitable solvent to form a mixture; and c) stirring the mixture obtained in step (b) under conditions to obtain said oligomer.

15. The method of claim 14, wherein the di-imidazole unit bearing linker 2 of Formula (III) is selected from the group consisting of

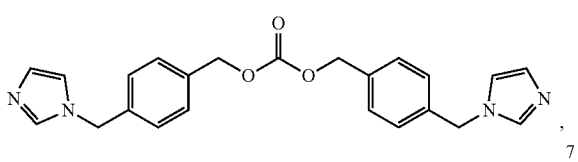

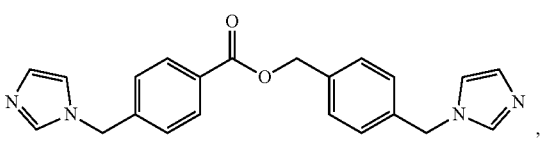

-continued

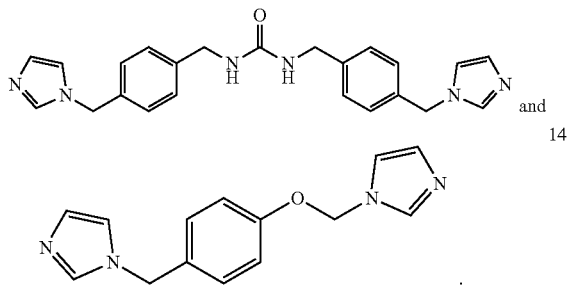

or wherein the imidazolium salt is selected from the group consisting of bisimidazolium salt, trisimidazolium salt, tetraimidazolium salt, pentaimidazolium salt and hexaimidazolium salt, or wherein the solvent is selected from the group consisting of dimethylformamide (DMF), dimethyl sulfoxide (DMSO), acetone and acetonitrile.

16. The method of claim 14, wherein said condition in step (c) comprises a temperature of about 20° C. to about 30° C., or wherein said step (c) is undertaken for a time period in the range of about 18 hours to 60 hours.

17. A method of preparing the oligomer or the polymer of Formula (II)

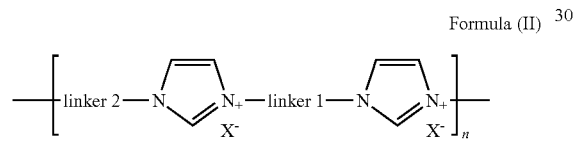
Formula (II)

wherein linker 1 is an alkyl-aryl-alkyl group or ($C_2$-$C_8$) alkene;
n is an integer from 3 to 30, that is 3, 4, 5, 6, 7, 8, 9, 10, 11, 12, 13, 14, 15, 16, 17, 18, 19, 20, 21, 22, 23, 24, 25, 26, 27, 28, 29 or 30;
linker 2 is

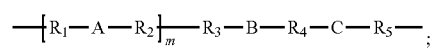

m is 0 or 1;
A is independently aryl or heteroaryl;
B is independently O, N or S;
C is independently aryl or heteroaryl;
$R_1$ is a bond or alkyl;
$R_2$ is a bond, alkoxy or amine;
$R_3$ is carbonyl, a bond or alkyl;
$R_4$ is a bond or alkyl;
$R_5$ is alkyl; and
X is halide selected from fluoride, chloride and bromide,
said method comprising the steps of:
a) mixing a di-imidazole unit bearing linker 2 of Formula (III):

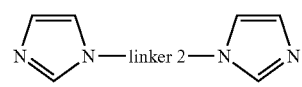
Formula III with a precursor bearing linker 1 of Formula (IV):

x—linker 1—x      Formula IV

Formula IV
in a suitable solvent to form a mixture; and
b) stirring the mixture obtained in step (a) under conditions to obtain said oligomer or said polymer.

18. The method of claim 17, wherein the di-imidazole unit bearing linker 2 of Formula (III) is selected from the group consisting of

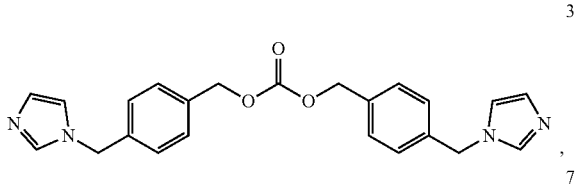
3

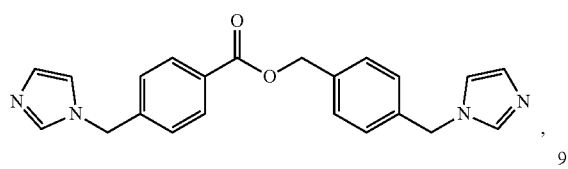
7

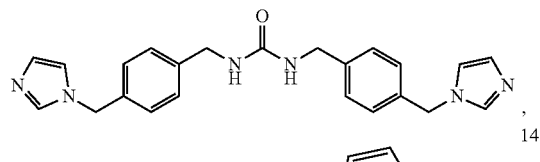
9

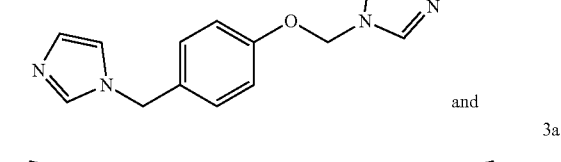
14

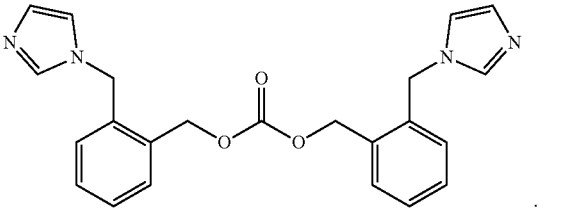
and

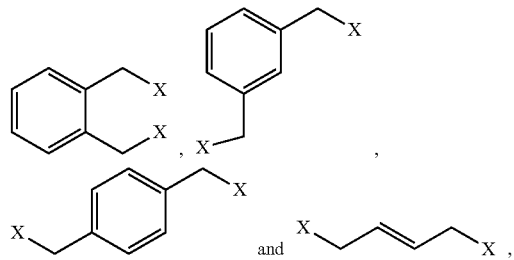
3a or wherein the precursor bearing linker 1 of Formula (IV) is selected from the group consisting of

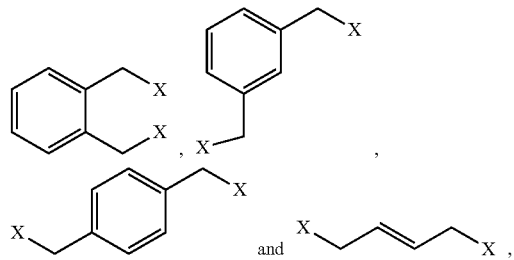

or wherein the polymer of Formula (II) is selected from the group consisting of

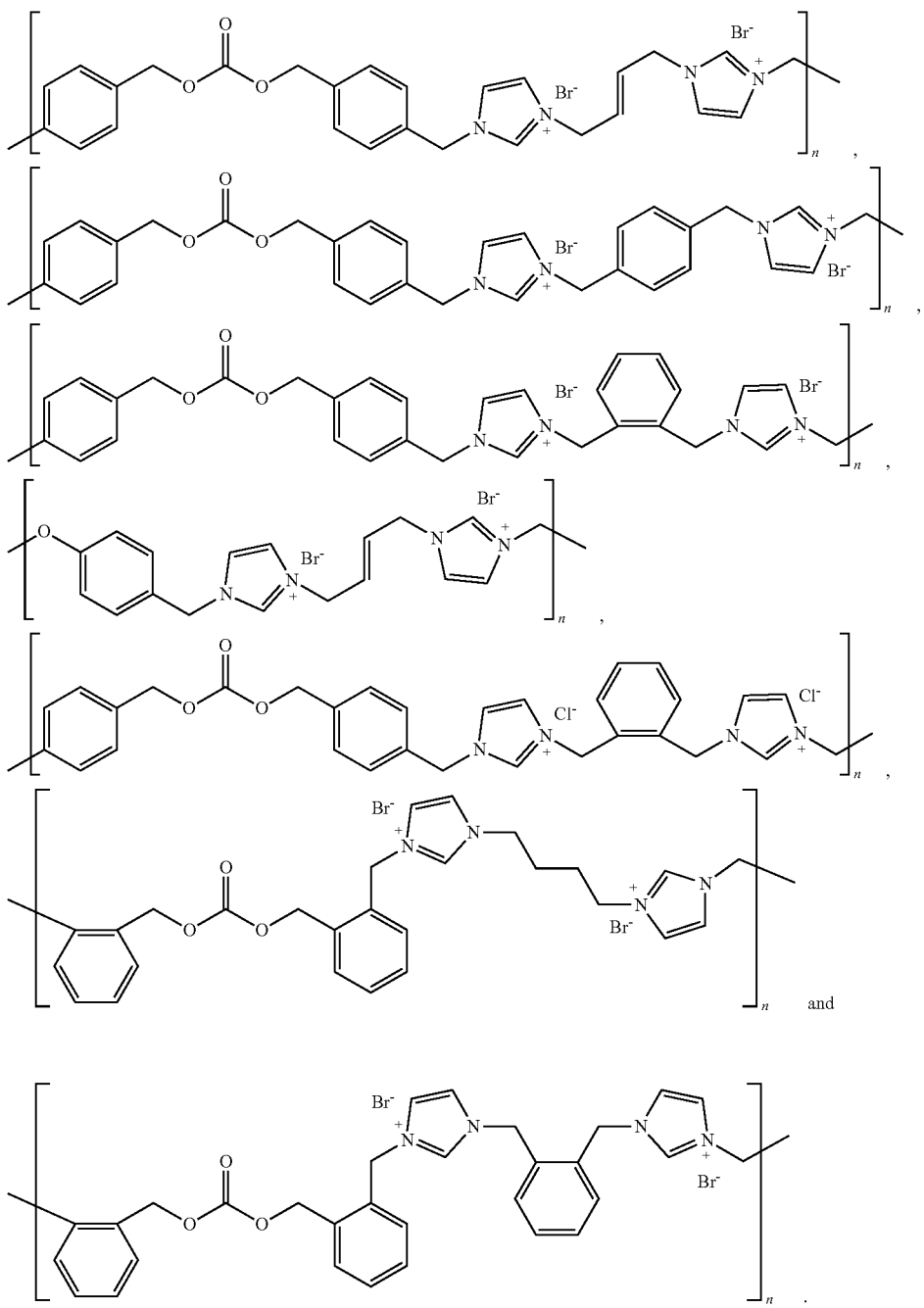
19. The method of claim 17, wherein said condition in step (b) comprises a temperature of about 20° C. to about 30° C., or wherein step (b) is undertaken for a period of time in the range of about 30 minutes to about 48 hours, or wherein the method optionally further comprises the step of heating said mixture.
20. An antimicrobial gel comprising an oligomer of formula (I)
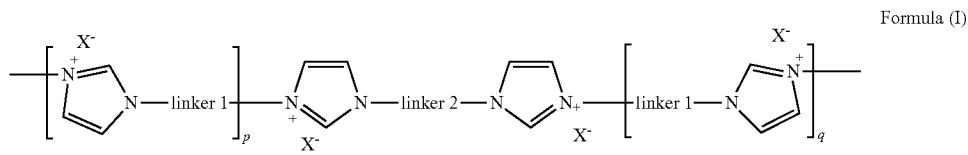
Formula (I)

wherein linker 1 is an alkyl-aryl-alkyl group or (C$_2$-C$_8$) alkene;

p and q are independently an integer from 2 to 6, that is 2, 3, 4, 5, or 6;

linker 2 is

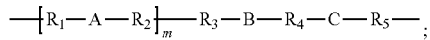

m is 0 or 1;
A is independently aryl or heteroaryl;
B is independently O, N or S;
C is independently aryl or heteroaryl;
R$_1$ is a bond or alkyl;
R$_2$ is a bond, alkoxy or amine;
R$_3$ is carbonyl, a bond or alkyl;
R$_4$ is a bond or alkyl;
R$_5$ is alkyl; and
X is halide selected from fluoride, chloride and bromide.

21. An antimicrobial composition comprising the oligomer or the polymer as defined in claim 5.

22. A method of treating a microbial infection or disease comprising administering the oligomer or polymer of claim 5 to a subject.

23. The method of claim 22, wherein said oligomer or polymer treats the infection or disease caused by a microbe that is selected from the group consisting of *Staphylococcus aureus, Escherichia coli, Pseudomonas aeruginosa, Bacillus subtilius, Klebsiella pneumonia, Cryptococcus neoformans* and *Candida albicans*.

24. The method of claim 23, wherein when said microbe is contacted with said oligomer or said polymer at a defined concentration, microbial activity of said microbe is reduced to 1% or wherein said defined concentration of said oligomer or said polymer is in the range of about 1 µg/ml to about 100 µg/ml.

25. A method of inhibiting a microbial activity comprising applying said oligomer or said polymer of claim 5 on a surface.

26. The method of claim 25, wherein said antimicrobial composition inhibits the activity caused by a microbe that is selected from the group consisting of *Staphylococcus aureus, Escherichia coli, Pseudomonas aeruginosa, Bacillus subtilius, Klebsiella pneumonia, Cryptococcus neoformans* and *Candida albicans*.

27. The method of claim 26, wherein when said microbe is contacted with said oligomer or said polymer at a defined concentration, microbial activity of said microbe is reduced to 1% or wherein said defined concentration of said antimicrobial composition is in the range of about 1 µg/ml to about 100 µg/ml.

* * * * *